US012121533B2

(12) United States Patent
Alcendor

(10) Patent No.: US 12,121,533 B2
(45) Date of Patent: Oct. 22, 2024

(54) ANTIVIRAL AGENTS FOR TREATMENT OF CORONAVIRUSES

(71) Applicant: Meharry Medical College, Nashville, TN (US)

(72) Inventor: Donald J. Alcendor, Hermitage, TN (US)

(73) Assignee: Meharry Medical College, Nashville, TN (US)

( * ) Notice: Subject to any disclaimer, the term of this patent is extended or adjusted under 35 U.S.C. 154(b) by 386 days.

(21) Appl. No.: 17/244,272

(22) Filed: Apr. 29, 2021

(65) Prior Publication Data

US 2022/0000904 A1 Jan. 6, 2022

Related U.S. Application Data

(60) Provisional application No. 63/017,603, filed on Apr. 29, 2020.

(51) Int. Cl.

*A61K 31/7125* (2006.01)
*A61K 47/64* (2017.01)
*A61P 31/14* (2006.01)

(52) U.S. Cl.

CPC ........ *A61K 31/7125* (2013.01); *A61K 47/641* (2017.08); *A61P 31/14* (2018.01)

(58) Field of Classification Search

CPC .... A61K 31/7125; A61K 47/641; A61P 31/14
See application file for complete search history.

(56) References Cited

U.S. PATENT DOCUMENTS

2005/0100885 A1* 5/2005 Crooke .............. C12N 15/1137 435/5

FOREIGN PATENT DOCUMENTS

WO WO-2021195025 A1 * 9/2021 ............. A61K 39/12
WO WO-2021207641 A1 * 10/2021 ........... A61K 31/713

OTHER PUBLICATIONS

Yokota T, Nakamura A, Nagata T, Saito T, Kobayashi M, Aoki Y, Echigoya Y, Partridge T, Hoffman EP, Takeda S. Extensive and prolonged restoration of dystrophin expression with vivo-morpholino-mediated multiple exon skipping in dystrophic dogs. Nucleic Acid Ther. Oct. 2012;22(5):306-15. (Year: 2012).*

Setten RL, Rossi JJ, Han SP. The current state and future directions of RNAi-based therapeutics. Nat Rev Drug Discov. Jun. 2019; 18(6):421-446. doi: 10.1038/s41573-019-0017-4. Erratum in: Nat Rev Drug Discov. Mar. 18, 2019;: Erratum in: Nat Rev Drug Discov. Apr. 24, 2019;: PMID: 30846871. (Year: 2019).*

Berber B, Aydin C, Kocabas F, Guney-Esken G, Yilancioglu K, Karadag-Alpaslan M, Caliseki M, Yuce M, Demir S, Tastan C. Gene editing and RNAi approaches for COVID-19 diagnostics and therapeutics. Gene Ther. Jun. 2021;28(6):290-305. doi: 10.1038/s41434-020-00209-7. Dec. 14, 2020. PMID: 33318646; PMCID: (Year: 2020).*

Stower, H., Virological Assessment of SARS-COV-2, Nature Medicine, 2020, vol. 26, No. 4, p. 465.

Pedersen, S. & Ho, Y., SARS-COV-2: a storm is raging, The Journal of Clinical Investigation, 2020, vol. 130, No. 5, pp. 2202-2205.

Zheng, J., SARS-COV-2: an Emerging Coronavirus that Causes a Global Threat, International Journal of Biological Sciences, 2020, vol. 16, No. 10, pp. 1678-1685.

Kickbusch et al.,Covid-19: how a virus is turning the world upside down, BMJ, 2020, vol. 368, No. 8241, pp. 68-69.

Andersen et al., The proximal origin of SARS-COV-2, Nature Medicine, 2020, vol. 26, No. 4, pp. 450-452.

Nicola et al., The socio-economic implications of the coronavirus pandemic (COVID-19): A review, International Journal of Surgery, 2020, vol. 78, pp. 185-193.

Ayittey et al., Economic impacts of Wuhan 2019-nCOV on China and the world, Journal of Medical Virology, 2020, vol. 92, No. 5, pp. 473-475.

Basile et al., Recommendations for the prevention, mitigation and containment of the emerging SARS-COV-2 (COVID-19) pandemic in haemodialysis centres, Nephrology Dialysis Transplantation, 2020, vol. 35, No. 5, pp. 737-741.

Koo et al., Interventions to mitigate early spread of SARS-COV-2 in Singapore: a modelling study, The Lancet Infectious Diseases, 2020, vol. 20, No. 6, pp. 678-688.

Rabby, M.I.I., Current Drugs with Potential for Treatment of COVID-19: A Literature Review, Journal of Pharmacy & Pharmaceutical Sciences, 2020, vol. 23, No. 1, pp. 58-64.

Lubick, N., Q&A: Keeping antivirals viable, Nature, 2019, vol. 573, No. 7774, p. S53.

Huang et al., Epidemiology and Clinical Characteristics of COVID-19, Archives of Iranian Medicine, 2020, vol. 23, No. 4, pp. 268-271.

Rothan, H. & Byrareddt S., The epidemiology and pathogenesis of coronavirus disease (COVID-19) outbreak, Journal of Autoimmunity, 2020, vol. 109, Article 102433.

Zu et al., Coronavirus Disease 2019 (COVID-19): A Perspective from China, Radiology, 2020, vol. 296, No. 2, pp. E15-E25.

Pneumonia of unknown cause: China, World Health Organization (Jan. 5, 2020), https://www.who.int/emergencies/disease-outbreak-news/item/2020-DON229.

Coronavirus disease (COVID-19) technical guidance: The Unity Studies: Early Investigation Protocols, World Health Organization, https://www.who.int/emergencies/diseases/novel-coronavirus-2019/technical-guidance/early-investigations (last visited Dec. 29, 2021).

(Continued)

*Primary Examiner* — Richard A Schnizer
(74) *Attorney, Agent, or Firm* — Bradley Arant Boult Cummings LLP; Phil Walker; Jessica L. Zurlo

(57) ABSTRACT

An antiviral agent is provided, having a phosphorodiamidate morpholino oligomer with an antisense sequence to a portion of a genome of a strain of a coronavirus. The coronavirus may be SARS-CoV-2 or another βCoV. The antiviral agent finds many uses, such as in a pharmaceutical composition, a method of treating coronavirus-mediated disease, a method of preventing coronavirus-mediated disease, a method of reducing or preventing the replication of coronavirus in a host cell, a method of controlling the spread of coronavirus in donated tissue, a treated tissue sample, and in the manufacture of a medicament for the treatment or prevention or coronavirus-mediated disease.

14 Claims, 2 Drawing Sheets

Specification includes a Sequence Listing.

(56) References Cited

OTHER PUBLICATIONS

COVID-19 Dashboard, Center for Systems Science and Engineering at John Hopkins University, https://gisanddata.maps.arcgis.com/apps/dashboards/bda7594740fd40299423467b48e9ecf6 (last visited Dec. 29, 2021).
Bassetti et al., The novel Chinese coronavirus (2019-nCOV) infections: Challenges for fighting the storm, European Journal of Clinical Investigation, 2020, vol. 50, No. 3, Article e13209.
Woo et al., Discovery of seven novel Mammalian and avian coronaviruses in the genus deltacoronavirus supports bat coronaviruses as the gene source of alphacoronavirus and betacoronavirus and avian coronaviruses as the gene source of gammacoronavirus and deltacoronavirus, Journal of Virology, 2012, vol. 86, No. 7, pp. 3995-4008.
Virus Taxonomy: 2017 Release, International Committee on Taxonomy of Viruses (Jul. 2017), https://talk.ictvonline.org/taxonomy/p/taxonomy_releases.
Du Toit, A., Outbreak of a novel coronavirus, Nature Reviews Microbiology, 2020, vol. 18, p. 123.
Hui et al., The continuing 2019-nCOV epidemic threat of novel coronaviruses to global health—the latest 2019 novel coronavirus outbreak in Wuhan, International Journal of Infectious Diseases, 2020, vol. 91, pp. 264-266.
Woo et al., Characterization and complete genome sequence of a novel coronavirus, coronavirus HKU1, from patients with pneumonia, Journal of Virology, 2005, vol. 79, No. 2, pp. 884-895.
Fehr, A. & Perlmans., Coronaviruses: an overview of their replication and pathogenesis, Coronaviruses, 2015, vol. 1282, pp. 1-23.
Chan et al., Interspecies transmission and emergence of novel viruses: lessons from bats and birds, Trends in Microbiology, 2013, vol. 21, No. 10, pp. 544-555.
Su et al., Epidemiology, genetic recombination, and pathogenesis of coronaviruses, Trends in Microbiology, 2016, vol. 24, No. 6, pp. 490-502.
Cheng et al., Severe Acute Respiratory Syndrome Coronavirus as an Agent of Emerging and Reemerging Infection, Clinical Microbiology Reviews, 2007, vol. 20, No. 4, pp. 660-694.
Chan et al., Middle East respiratory syndrome coronavirus: another zoonotic betacoronavirus causing SARS-like disease, Clinical Microbiology Reviews, 2015, vol. 28, No. 2, pp. 465-522.
Song et al., From SARS to MERS, Thrusting Coronaviruses into the Spotlight, VIRUSES, 2019, vol. 11, No. 1, Article 59.
Chafeker, A. & Fielding, B., MERS-CoV: Understanding the Latest Human Coronavirus Threat, Viruses, 2018, vol. 20, No. 2, Article 93.
Popik et al., Phosphorodiamidate morpholino targeting the 5' untranslated region of the ZIKV RNA inhibits virus replication, Virology, 2018, vol. 519, pp. 77-85.
Ye et al., The pathogenesis and treatment of the 'Cytokine Storm' in COVID-19, Journal of Infection, 2020, vol. 80, No. 6, pp. 607-613.
Keyaerts et al., Antiviral Activity of Chloroquine against Human Coronavirus OC43 Infection in Newborn Mice, 2009, vol. 53, No. 8, pp. 3416-3421.
Chan et al., A familial cluster of pneumonia associated with the 2019 novel coronavirus indicating person-to-person transmission: a study of a family cluster, 2020, The Lancet, vol. 395, No. 10223, p. 514-523.
Hu et al, Genomic characterization and infectivity of a novel SARS-like coronavirus in Chinese bats, Emerging Microbes & Inections, 2018, vol. 7, No. 1, Article 154.
Marra et al., The Genome sequence of the SARS-associated coronavirus, Science, 2003, vol. 300, No. 5624, pp. 1399-1404.
Arabi et al., Clinical course and outcomes of critically ill patients with Middle East respiratory syndrome coronavirus infection, Annals of Internal Medicine, 2014, vol. 160, No. 16, pp. 389-397.
Summerton, J. & Weller, D., Morpholino antisense oligomers: Design, preparation, and properties, Antisense Nucleic Acid Drug Development, 1997, vol. 7, No. 3, pp. 187-195.
Li, Y. & Morcos, P., Design and synthesis of dendritic molecular transporter that achieves efficient in vivo delivery of morpholino antisense oligo, Bioconjugate Chemistry, 2008, vol. 19, No. 7, pp. 1464-1470.
Maddox et al., Adapting cell based assays to the high throughput screening platform: Problems encountered and lessons learned, JALA, 2008, vol. 30, No. 3, pp. 168-173.
Severson et al., Development and validation of a high-throughput screen for inhibitors of SARS CoV and its application in screening of a 100,000-compound library, Journal of Biomolecular Screening, 2007, vol. 12, No. 1, pp. 33-40.
Li et al., Angiotensin-converting enzyme 2 is a functional receptor for the SARS coronavirus, Nature, 2003, vol. 426, No. 6965, pp. 450-454.

* cited by examiner

SEQUENCE LISTING

```
<160> NUMBER OF SEQ ID NOS: 7

<210> SEQ ID NO 1
<211> LENGTH: 25
<212> TYPE: DNA
<213> ORGANISM: Artificial Sequence
<220> FEATURE:
<223> OTHER INFORMATION: Synthetic Phosphorodiamidate Morpholino
      Oligomer

<400> SEQUENCE: 1

agggacaagg ctctccatct tacct                                            25


<210> SEQ ID NO 2
<211> LENGTH: 25
<212> TYPE: DNA
<213> ORGANISM: Severe acute respiratory syndrome coronavirus 2

<400> SEQUENCE: 2

aggtaagatg gagagccttg tccct                                            25


<210> SEQ ID NO 3
<211> LENGTH: 25
<212> TYPE: DNA
<213> ORGANISM: Artificial Sequence
<220> FEATURE:
<223> OTHER INFORMATION: Synthetic Phosphorodiamidate Morpholino
      Oligomer

<400> SEQUENCE: 3

aagaacaagg ctctccatct tacct                                            25


<210> SEQ ID NO 4
<211> LENGTH: 25
<212> TYPE: DNA
<213> ORGANISM: Severe acute respiratory syndrome coronavirus 2
```

-continued

<400> SEQUENCE: 4
gctgggaaag accagagact ccatg 25

<210> SEQ ID NO 5
<211> LENGTH: 29891
<212> TYPE: DNA
<213> ORGANISM: Severe acute respiratory syndrome coronavirus 2
<300> PUBLICATION INFORMATION:
<308> DATABASE ACCESSION NUMBER: GENBANK/MN975262
<309> DATABASE ENTRY DATE: 2020-02-11
<313> RELEVANT RESIDUES IN SEQ ID NO: (1)..(29891)

<400> SEQUENCE: 5
attaaaggtt tataccttcc caggtaacaa accaaccaac tttcgatctc ttgtagatct 60
gttctctaaa cgaactttaa aatctgtgtg gctgtcactc ggctgcatgc ttagtgcact 120
cacgcagtat aattaataac taattactgt cgttgacagg acacgagtaa ctcgtctatc 180
ttctgcaggc tgcttacggt ttcgtccgtg ttgcagccga tcatcagcac atctaggttt 240
cgtccgggtg tgaccgaaag gtaagatgga gagccttgtc cctggtttca acgagaaaac 300
acacgtccaa ctcagtttgc ctgttttaca ggttcgcgac gtgctcgtac gtggctttgg 360
agactccgtg gaggaggtct tatcagaggc acgtcaacat cttaaagatg gcacttgtgg 420
cttagtagaa gttgaaaaag gcgttttgcc tcaacttgaa cagccctatg tgttcatcaa 480
acgttcggat gctcgaactg cacctcatgg tcatgttatg gttgagctgg tagcagaact 540
cgaaggcatt cagtacggtc gtagtggtga gacacttggt gtccttgtcc ctcatgtggg 600
cgaaatacca gtggcttacc gcaaggttct tcttcgtaag aacggtaata aaggagctgg 660
tggccatagt tacggcgccg atctaaagtc atttgactta ggcgacgagc ttggcactga 720
tccttatgaa gattttcaag aaaactggaa cactaaacat agcagtggtg ttacccgtga 780
actcatgcgt gagcttaacg gaggggcata cactcgctat gtcgataaca acttctgtgg 840
ccctgatggc taccctcttg agtgcattaa agaccttcta gcacgtgctg gtaaagcttc 900
atgcactttg tccgaacaac tggactttat tgacactaag aggggtgtat actgctgccg 960
tgaacatgag catgaaattg cttggtacac ggaacgttct gaaaagagct atgaattgca 1020
gacacctttt gaaattaaat tggcaaagaa atttgacacc ttcaatgggg aatgtccaaa 1080
ttttgtattt cccttaaatt ccataatcaa gactattcaa ccaagggttg aaaagaaaaa 1140
gcttgatggc tttatgggta gaattcgatc tgtctatcca gttgcgtcac caaatgaatg 1200
caaccaaatg tgcctttcaa ctctcatgaa gtgtgatcat tgtggtgaaa cttcatggca 1260
gacgggcgat tttgttaaag ccacttgcga attttgtggc actgagaatt tgactaaaga 1320
aggtgccact acttgtggtt acttacccca aaatgctgtt gttaaaattt attgtccagc 1380
atgtcacaat tcagaagtag gacctgagca tagtcttgcc gaataccata atgaatctgg 1440
cttgaaaacc attcttcgta agggtggtcg cactattgcc tttggaggct gtgtgttctc 1500
ttatgttggt tgccataaca agtgtgccta ttgggttcca cgtgctagcg ctaacatagg 1560
ttgtaaccat acaggtgttg ttggagaagg ttccgaaggt cttaatgaca accttcttga 1620
aatactccaa aaagagaaag tcaacatcaa tattgttggt gactttaaac ttaatgaaga 1680
gatcgccatt attttggcat ctttttctgc ttccacaagt gcttttgtgg aaactgtgaa 1740
aggtttggat tataaagcat tcaaacaaat tgttgaatcc tgtggtaatt ttaaagttac 1800
aaaaggaaaa gctaaaaaag gtgcctggaa tattggtgaa cagaaatcaa tactgagtcc 1860
tctttatgca tttgcatcag aggctgctcg tgttgtacga tcaattttct cccgcactct 1920

-continued

```
tgaaactgct caaaattctg tgcgtgtttt acagaaggcc gctataacaa tactagatgg   1980
aatttcacag tattcactga gactcattga tgctatgatg ttcacatctg atttggctac   2040
taacaatcta gttgtaatgg cctacattac aggtggtgtt gttcagttga cttcgcagtg   2100
gctaactaac atctttggca ctgtttatga aaaactcaaa cccgtccttg attggcttga   2160
agagaagttt aaggaaggtg tagagtttct tagagacggt tgggaaattg ttaaatttat   2220
ctcaacctgt gcttgtgaaa ttgtcggtgg acaaattgtc acctgtgcaa aggaaattaa   2280
ggagagtgtt cagacattct ttaagcttgt aaataaattt ttggctttgt gtgctgactc   2340
tatcattatt ggtggagcta aacttaaagc cttgaattta ggtgaaacat ttgtcacgca   2400
ctcaaaggga ttgtacagaa agtgtgttaa atccagagaa gaaactggcc tactcatgcc   2460
tctaaaagcc ccaaaagaaa ttatcttctt agagggagaa acacttccca cagaagtgtt   2520
aacagaggaa gttgtcttga aaactggtga tttacaacca ttagaacaac ctactagtga   2580
agctgttgaa gctccattgg ttggtacacc agtttgtatt aacgggctta tgttgctcga   2640
aatcaaagac acagaaaagt actgtgccct tgcacctaat atgatggtaa caaacaatac   2700
cttcacactc aaaggcggtg caccaacaaa ggttactttt ggtgatgaca ctgtgataga   2760
agtgcaaggt tacaagagtg tgaatatcac ttttgaactt gatgaaagga ttgataaagt   2820
acttaatgag aagtgctctg cctatacagt tgaactcggt acagaagtaa atgagttcgc   2880
ctgtgttgtg gcagatgctg tcataaaaac tttgcaacca gtatctgaat tacttacacc   2940
actgggcatt gatttagatg agtggagtat ggctacatac tacttatttg atgagtctgg   3000
tgagtttaaa ttggcttcac atatgtattg ttctttctac cctccagatg aggatgaaga   3060
agaaggtgat tgtgaagaag aagagtttga gccatcaact caatatgagt atggtactga   3120
agatgattac caaggtaaac ctttggaatt tggtgccact tctgctgctc ttcaacctga   3180
agaagagcaa gaagaagatt ggttagatga tgatagtcaa caaactgttg gtcaacaaga   3240
cggcagtgag gacaatcaga caactactat tcaaacaatt gttgaggttc aacctcaatt   3300
agagatggaa cttacaccag ttgttcagac tattgaagtg aatagtttta gtggttattt   3360
aaaacttact gacaatgtat acattaaaaa tgcagacatt gtggaagaag ctaaaaaggt   3420
aaaaccaaca gtggttgtta atgcagccaa tgtttacctt aaacatggag gaggtgttgc   3480
aggagcctta aataaggcta ctaacaatgc catgcaagtt gaatctgatg attacatagc   3540
tactaatgga ccacttaaag tgggtggtag ttgtgtttta agcggacaca atcttgctaa   3600
acactgtctt catgttgtcg gcccaaatgt taacaaaggt gaagacattc aacttcttaa   3660
gagtgcttat gaaaatttta atcagcacga agttctactt gcaccattat tatcagctgg   3720
tatttttggt gctgacccta tacattcttt aagagtttgt gtagatactg ttcgcacaaa   3780
tgtctactta gctgtctttg ataaaaatct ctatgacaaa cttgtttcaa gctttttgga   3840
aatgaagagt gaaaagcaag ttgaacaaaa gatcgctgag attcctaaag aggaagttaa   3900
gccatttata actgaaagta aaccttcagt tgaacagaga aaacaagatg ataagaaaat   3960
caaagcttgt gttgaagaag ttacaacaac tctggaagaa actaagttcc tcacagaaaa   4020
cttgttactt tatattgaca ttaatggcaa tcttcatcca gattctgcca ctcttgttag   4080
tgacattgac atcactttct taaagaaaga tgctccatat atagtgggtg atgttgttca   4140
agagggtgtt ttaactgctg tggttatacc tactaaaaag gctggtggca ctactgaaat   4200
gctagcgaaa gctttgagaa aagtgccaac agacaattat ataaccactt acccgggtca   4260
```

```
gggtttaaat ggttacactg tagaggaggc aaagacagtg cttaaaaagt gtaaaagtgc   4320
cttttacatt ctaccatcta ttatctctaa tgagaagcaa gaaattcttg gaactgtttc   4380
ttggaatttg cgagaaatgc ttgcacatgc agaagaaaca cgcaaattaa tgcctgtctg   4440
tgtggaaact aaagccatag tttcaactat acagcgtaaa tataagggta ttaaaataca   4500
agagggtgtg gttgattatg gtgctagatt ttacttttac accagtaaaa caactgtagc   4560
gtcacttatc aacacactta acgatctaaa tgaaactctt gttacaatgc cacttggcta   4620
tgtaacacat ggcttaaatt tggaagaagc tgctcggtat atgagatctc tcaaagtgcc   4680
agctacagtt tctgtttctt cacctgatgc tgttacagcg tataatggtt atcttacttc   4740
ttcttctaaa acacctgaag aacattttat tgaaaccatc tcacttgctg gttcctataa   4800
agattggtcc tattctggac aatctacaca actaggtata gaatttctta agagaggtga   4860
taaaagtgta tattacacta gtaatcctac cacattccac ctagatggtg aagttatcac   4920
ctttgacaat cttaagacac ttctttcttt gagagaagtg aggactatta aggtgtttac   4980
aacagtagac aacattaacc tccacacgca agttgtggac atgtcaatga catatggaca   5040
acagtttggt ccaacttatt tggatggagc tgatgttact aaaataaaac ctcataattc   5100
acatgaaggt aaaacatttt atgttttacc taatgatgac actctacgtg ttgaggcttt   5160
tgagtactac cacacaactg atcctagttt tctgggtagg tacatgtcag cattaaatca   5220
cactaaaaag tggaaatacc cacaagttaa tggtttaact tctattaaat gggcagataa   5280
caactgttat cttgccactg cattgttaac actccaacaa atagagttga agtttaatcc   5340
acctgctcta caagatgctt attacagagc aagggctggt gaagctgcta acttttgtgc   5400
acttatctta gcctactgta ataagacagt aggtgagtta ggtgatgtta gagaaacaat   5460
gagttacttg tttcaacatg ccaatttaga ttcttgcaaa agagtcttga acgtggtgtg   5520
taaaacttgt ggacaacagc agacaaccct taagggtgta gaagctgtta tgtacatggg   5580
cacactttct tatgaacaat ttaagaaagg tgttcagata ccttgtacgt gtggtaaaca   5640
agctacaaaa tatctagtac aacaggagtc accttttgtt atgatgtcag caccacctgc   5700
tcagtatgaa cttaagcatg gtacatttac ttgtgctagt gagtacactg gtaattacca   5760
gtgtggtcac tataaacata taacttctaa agaaactttg tattgcatag acggtgcttt   5820
acttacaaag tcctcagaat acaaaggtcc tattacggat gttttctaca aagaaaacag   5880
ttacacaaca accataaaac cagttactta taaattggat ggtgttgttt gtacagaaat   5940
tgaccctaag ttggacaatt attataagaa agacaattct tatttcacag agcaaccaat   6000
tgatcttgta ccaaaccaac catatccaaa cgcaagcttc gataatttta agtttgtatg   6060
tgataatatc aaatttgctg atgatttaaa ccagttaact ggttataaga aacctgcttc   6120
aagagagctt aaagttacat ttttccctga cttaaatggt gatgtggtgg ctattgatta   6180
taaacactac acaccctctt ttaagaaagg agctaaattg ttacataaac ctattgtttg   6240
gcatgttaac aatgcaacta ataaagccac gtataaacca aatacctggt gtatacgttg   6300
tctttggagc acaaaaccag ttgaaacatc aaattcgttt gatgtactga agtcagagga   6360
cgcgcaggga atggataatc ttgcctgcga agatctaaaa ccagtctctg aagaagtagt   6420
ggaaaatcct accatacaga aagacgttct tgagtgtaat gtgaaaacta ccgaagttgt   6480
aggagacatt atacttaaac cagcaaataa tagtttaaaa attacagaag aggttggcca   6540
cacagatcta atggctgctt atgtagacaa ttctagtctt actattaaga aacctaatga   6600
attatctaga gtattaggtt tgaaaaccct tgctactcat ggtttagctg ctgttaatag   6660
```

-continued

```
tgtcccttgg gatactatag ctaattatgc taagcctttt cttaacaaag ttgttagtac   6720
aactactaac atagttacac ggtgtttaaa ccgtgtttgt actaattata tgccttattt   6780
ctttacttta ttgctacaat tgtgtacttt tactagaagt acaaattcta gaattaaagc   6840
atctatgccg actactatag caaagaatac tgttaagagt gtcggtaaat tttgtctaga   6900
ggcttcattt aattatttga agtcacctaa tttttctaaa ctgataaata ttataatttg   6960
gtttttacta ttaagtgttt gcctaggttc tttaatctac tcaaccgctg ctttaggtgt   7020
tttaatgtct aatttaggca tgccttctta ctgtactggt tacagagaag gctatttgaa   7080
ctctactaat gtcactattg caacctactg tactggttct ataccttgta gtgtttgtct   7140
tagtggttta gattctttag acacctatcc ttctttagaa actatacaaa ttaccatttc   7200
atcttttaaa tgggatttaa ctgcttttgg cttagttgca gagtggtttt tggcatatat   7260
tcttttcact aggtttttct atgtacttgg attggctgca atcatgcaat tgtttttcag   7320
ctattttgca gtacatttta ttagtaattc ttggcttatg tggttaataa ttaatcttgt   7380
acaaatggcc ccgatttcag ctatggttag aatgtacatc ttctttgcat catttatta   7440
tgtatggaaa agttatgtgc atgttgtaga cggttgtaat tcatcaactt gtatgatgtg   7500
ttacaaacgt aatagagcaa caagagtcga atgtacaact attgttaatg gtgttagaag   7560
gtccttttat gtctatgcta atggaggtaa aggcttttgc aaactacaca attggaattg   7620
tgttaattgt gatacattct gtgctggtag tacatttatt agtgatgaag ttgcgagaga   7680
cttgtcacta cagtttaaaa gaccaataaa tcctactgac cagtcttctt acatcgttga   7740
tagtgttaca gtgaagaatg gttccatcca tctttacttt gataaagctg gtcaaaagac   7800
ttatgaaaga cattctctct ctcattttgt taacttagac aacctgagag ctaataacac   7860
taaaggttca ttgcctatta atgttatagt ttttgatggt aaatcaaaat gtgaagaatc   7920
atctgcaaaa tcagcgtctg tttactacag tcagcttatg tgtcaaccta tactgttact   7980
agatcaggca ttagtgtctg atgttggtga tagtgcggaa gttgcagtta aaatgtttga   8040
tgcttacgtt aatacgtttt catcaacttt taacgtacca atggaaaaac tcaaaacact   8100
agttgcaact gcagaagctg aacttgcaaa gaatgtgtcc ttagacaatg tcttatctac   8160
ttttatttca gcagctcggc aagggtttgt tgattcagat gtagaaacta aagatgttgt   8220
tgaatgtctt aaattgtcac atcaatctga catagaagtt actggcgata gttgtaataa   8280
ctatatgctc acctataaca aagttgaaaa catgacaccc cgtgaccttg gtgcttgtat   8340
tgactgtagt gcgcgtcata ttaatgcgca ggtagcaaaa agtcacaaca ttgctttgat   8400
atggaacgtt aaagatttca tgtcattgtc tgaacaacta cgaaaacaaa tacgtagtgc   8460
tgctaaaaag aataacttac cttttaagtt gacatgtgca actactagac aagttgttaa   8520
tgttgtaaca acaaagatag cacttaaggg tggtaaaatt gttaataatt ggttgaagca   8580
gttaattaaa gttacacttg tgttcctttt tgttgctgct attttctatt taataacacc   8640
tgttcatgtc atgtctaaac atactgactt ttcaagtgaa atcataggat acaaggctat   8700
tgatggtggt gtcactcgtg acatagcatc tacagatact tgttttgcta acaaacatgc   8760
tgattttgac acatggttta gtcagcgtgg tggtagttat actaatgaca aagcttgccc   8820
attgattgct gcagtcataa caagagaagt gggttttgtc gtgcctggtt tgcctggcac   8880
gatattacgc acaactaatg gtgacttttt gcatttctta cctagagttt ttagtgcagt   8940
tggtaacatc tgttacacac catcaaaact tatagagtac actgactttg caacatcagc   9000
```

-continued

```
ttgtgttttg gctgctgaat gtacaatttt taaagatgct tctggtaagc cagtaccata   9060
ttgttatgat accaatgtac tagaaggttc tgttgcttat gaaagtttac gccctgacac   9120
acgttatgtg ctcatggatg gctctattat tcaatttcct aacacctacc ttgaaggttc   9180
tgttagagtg gtaacaactt ttgattctga gtactgtagg cacggcactt gtgaaagatc   9240
agaagctggt gtttgtgtat ctactagtgg tagatgggta cttaacaatg attattacag   9300
atctttacca ggagttttct gtggtgtaga tgctgtaaat ttacttacta atatgtttac   9360
accactaatt caacctattg gtgctttgga catatcagca tctatagtag ctggtggtat   9420
tgtagctatc gtagtaacat gccttgccta ctattttatg aggtttagaa gagcttttgg   9480
tgaatacagt catgtagttg cctttaatac tttactattc cttatgtcat tcactgtact   9540
ctgtttaaca ccagtttact tattcttacc tggtgtttat tctgttattt acttgtactt   9600
gacattttat cttactaatg atgtttcttt tttagcacat attcagtgga tggttatgtt   9660
cacaccttta gtacctttct ggataacaat tgcttatatc atttgtattt ccacaaagca   9720
tttctattgg ttctttagta attacctaaa gagacgtgta gtctttaatg gtgtttcctt   9780
tagtactttt gaagaagctg cgctgtgcac ctttttgtta aataaagaaa tgtatctaaa   9840
gttgcgtagt gatgtgctat tacctcttac gcaatataat agatacttag ctctttataa   9900
taagtacaag tattttagtg gagcaatgga tacaactagc tacagagaag ctgcttgttg   9960
tcatctcgca aaggctctca atgacttcag taactcaggt tctgatgttc tttaccaacc  10020
accacaaacc tctatcacct cagctgtttt gcagagtggt tttagaaaaa tggcattccc  10080
atctggtaaa gttgagggtt gtatggtaca agtaacttgt ggtacaacta cacttaacgg  10140
tctttggctt gatgacgtag tttactgtcc aagacatgtg atctgcacct ctgaagacat  10200
gcttaaccct aattatgaag atttactcat tcgtaagtct aatcataatt tcttggtaca  10260
ggctggtaat gttcaactca gggttattgg acattctatg caaaattgtg tacttaagct  10320
taaggttgat acagccaatc ctaagacacc taagtataag tttgttcgca ttcaaccagg  10380
acagactttt tcagtgttag cttgttacaa tggttcacca tctggtgttt accaatgtgc  10440
tatgaggccc aatttcacta ttaagggttc attccttaat ggttcatgtg gtagtgttgg  10500
ttttaacata gattatgact gtgtctcttt ttgttacatg caccatatgg aattaccaac  10560
tggagttcat gctggcacag acttagaagg taacttttat ggaccttttg ttgacaggca  10620
aacagcacaa gcagctggta cggacacaac tattacagtt aatgttttag cttggttgta  10680
cgctgctgtt ataaatggag acaggtggtt tctcaatcga tttaccacaa ctcttaatga  10740
ctttaacctt gtggctatga agtacaatta tgaacctcta acacaagacc atgttgacat  10800
actaggacct ctttctgctc aaactggaat tgccgtttta gatatgtgtg cttcattaaa  10860
agaattactg caaaatggta tgaatggacg taccatattg ggtagtgctt tattagaaga  10920
tgaatttaca ccttttgatg ttgttagaca atgctcaggt gttactttcc aaagtgcagt  10980
gaaaagaaca atcaagggta cacaccactg gttgttactc acaattttga cttcactttt  11040
agttttagtc cagagtactc aatggtcttt gttctttttt ttgtatgaaa atgccttttt  11100
accttttgct atgggtatta ttgctatgtc tgcttttgca atgatgtttg tcaaacataa  11160
gcatgcattt ctctgtttgt ttttgttacc ttctcttgcc actgtagctt attttaatat  11220
ggtctatatg cctgctagtt gggtgatgcg tattatgaca tggttggata tggttgatac  11280
tagtttgtct ggttttaagc taaaagactg tgttatgtat gcatcagctg tagtgttact  11340
aatccttatg acagcaagaa ctgtgtatga tgatggtgct aggagagtgt ggacacttat  11400
```

-continued

```
gaatgtcttg acactcgttt ataaagttta ttatggtaat gctttagatc aagccatttc  11460
catgtgggct cttataatct ctgttacttc taactactca ggtgtagtta caactgtcat  11520
gtttttggcc agaggtattg tttttatgtg tgttgagtat tgccctattt tcttcataac  11580
tggtaataca cttcagtgta taatgctagt ttattgtttc ttaggctatt tttgtacttg  11640
ttactttggc ctcttttgtt tactcaaccg ctactttaga ctgactcttg gtgtttatga  11700
ttacttagtt tctacacagg agtttagata tatgaattca cagggactac tcccacccaa  11760
gaatagcata gatgccttca aactcaacat taaattgttg ggtgttggtg gcaaaccttg  11820
tatcaaagta gccactgtac agtctaaaat gtcagatgta aagtgcacat cagtagtctt  11880
actctcagtt ttgcaacaac tcagagtaga atcatcatct aaattgtggg ctcaatgtgt  11940
ccagttacac aatgacattc tcttagctaa agatactact gaagcctttg aaaaaatggt  12000
ttcactactt tctgttttgc tttccatgca gggtgctgta gacataaaca agctttgtga  12060
agaaatgctg gacaacaggg caaccttaca agctatagcc tcagagttta gttcccttcc  12120
atcatatgca gcttttgcta ctgctcaaga agcttatgag caggctgttg ctaatggtga  12180
ttctgaagtt gttcttaaaa agttgaagaa gtctttgaat gtggctaaat ctgaatttga  12240
ccgtgatgca gccatgcaac gtaagttgga aaagatggct gatcaagcta tgacccaaat  12300
gtataaacag gctagatctg aggacaagag ggcaaaagtt actagtgcta tgcagacaat  12360
gcttttcact atgcttagaa agttggataa tgatgcactc aacaacatta tcaacaatgc  12420
aagagatggt tgtgttccct tgaacataat acctcttaca acagcagcca aactaatggt  12480
tgtcatacca gactataaca catataaaaa tacgtgtgat ggtacaacat ttacttatgc  12540
atcagcattg tgggaaatcc aacaggttgt agatgcagat agtaaaattg ttcaacttag  12600
tgaaattagt atggacaatt cacctaattt agcatggcct cttattgtaa cagctttaag  12660
ggccaattct gctgtcaaat tacagaataa tgagcttagt cctgttgcac tacgacagat  12720
gtcttgtgct gccggtacta cacaaactgc ttgcactgat gacaatgcgt tagcttacta  12780
caacacaaca aagggaggta ggtttgtact tgcactgtta tccgatttac aggatttgaa  12840
atgggctaga ttccctaaga gtgatggaac tggtactatc tatacagaac tggaaccacc  12900
ttgtaggttt gttacagaca cacctaaagg tcctaaagtg aagtatttat actttattaa  12960
aggattaaac aacctaaata gaggtatggt acttggtagt ttagctgcca cagtacgtct  13020
acaagctggt aatgcaacag aagtgcctgc caattcaact gtattatctt tctgtgcttt  13080
tgctgtagat gctgctaaag cttacaaaga ttatctagct agtgggggac aaccaatcac  13140
taattgtgtt aagatgttgt gtacacacac tggtactggt caggcaataa cagttacacc  13200
ggaagccaat atggatcaag aatcctttgg tggtgcatcg tgttgtctgt actgccgttg  13260
ccacatagat catccaaatc ctaaaggatt ttgtgactta aaaggtaagt atgtacaaat  13320
acctacaact tgtgctaatg accctgtggg ttttacactt aaaaacacag tctgtaccgt  13380
ctgcggtatg tggaaaggtt atggctgtag ttgtgatcaa ctccgcgaac ccatgcttca  13440
gtcagctgat gcacaatcgt ttttaaacgg gtttgcggtg taagtgcagc ccgtcttaca  13500
ccgtgcggca caggcactag tactgatgtc gtatacaggg cttttgacat ctacaatgat  13560
aaagtagctg gttttgctaa attcctaaaa actaattgtt gtcgcttcca agaaaaggac  13620
gaagatgaca atttaattga ttcttacttt gtagttaaga gacacacttt ctctaactac  13680
caacatgaag aaacaattta taatttactt aaggattgtc cagctgttgc taaacatgac  13740
```

-continued

```
ttctttaagt ttagaataga cggtgacatg gtaccacata tatcacgtca acgtcttact  13800
aaatacacaa tggcagacct cgtctatgct ttaaggcatt ttgatgaagg taattgtgac  13860
acattaaaag aaatacttgt cacatacaat tgttgtgatg atgattattt caataaaaag  13920
gactggtatg attttgtaga aaacccagat atattacgcg tatacgccaa cttaggtgaa  13980
cgtgtacgcc aagctttgtt aaaaacagta caattctgtg atgccatgcg aaatgctggt  14040
attgttggtg tactgacatt agataatcaa gatctcaatg gtaactggta tgatttcggt  14100
gatttcatac aaaccacgcc aggtagtgga gttcctgttg tagattctta ttattcattg  14160
ttaatgccta tattaacctt gaccagggct ttaactgcag agtcacatgt tgacactgac  14220
ttaacaaagc cttacattaa gtgggatttg ttaaaatatg acttcacgga agagaggtta  14280
aaactctttg accgttattt taaatattgg gatcagacat accacccaaa ttgtgttaac  14340
tgtttggatg acagatgcat tctgcattgt gcaaacttta atgttttatt ctctacagtg  14400
ttcccaccta caagttttgg accactagtg agaaaaatat ttgttgatgg tgttccattt  14460
gtagtttcaa ctggatacca cttcagagag ctaggtgttg tacataatca ggatgtaaac  14520
ttacatagct ctagacttag ttttaaggaa ttacttgtgt atgctgctga ccctgctatg  14580
cacgctgctt ctggtaatct attactagat aaacgcacta cgtgcttttc agtagctgca  14640
cttactaaca atgttgcttt tcaaactgtc aaacccggta attttaacaa agacttctat  14700
gactttgctg tgtctaaggg tttctttaag gaaggaagtt ctgttgaatt aaaacacttc  14760
ttctttgctc aggatggtaa tgctgctatc agcgattatg actactatcg ttataatcta  14820
ccaacaatgt gtgatatcag acaactacta tttgtagttg aagttgttga taagtacttt  14880
gattgttacg atggtggctg tattaatgct aaccaagtca tcgtcaacaa cctagacaaa  14940
tcagctggtt ttccatttaa taaatggggt aaggctagac tttattatga ttcaatgagt  15000
tatgaggatc aagatgcact tttcgcatat acaaaacgta atgtcatccc tactataact  15060
caaatgaatc ttaagtatgc cattagtgca aagaatagag ctcgcaccgt agctggtgtc  15120
tctatctgta gtactatgac caatagacag tttcatcaaa aattattgaa atcaatagcc  15180
gccactagag gagctactgt agtaattgga acaagcaaat tctatggtgg ttggcacaac  15240
atgttaaaaa ctgtttatag tgatgtagaa aaccctcacc ttatgggttg ggattatcct  15300
aaatgtgata gagccatgcc taacatgctt agaattatgg cctcacttgt tcttgctcgc  15360
aaacatacaa cgtgttgtag cttgtcacac cgtttctata gattagctaa tgagtgtgct  15420
caagtattga gtgaaatggt catgtgtggc ggttcactat atgttaaacc aggtggaacc  15480
tcatcaggag atgccacaac tgcttatgct aatagtgttt ttaacatttg tcaagctgtc  15540
acggccaatg ttaatgcact tttatctact gatggtaaca aaattgccga taagtatgtc  15600
cgcaatctac aacacagact ttatgagtgt ctctatagaa atagagatgt tgacacagac  15660
tttgtgaatg agttttacgc atatttgcgt aaacatttct caatgatgat actctctgac  15720
gatgctgttg tgtgtttcaa tagcacttat gcatctcaag gtctagtggc tagcataaag  15780
aactttaagt cagttcttta ttatcaaaac aatgttttta tgtctgaagc aaaatgttgg  15840
actgagactg accttactaa aggacctcat gaattttgct ctcaacatac aatgctagtt  15900
aaacagggtg atgattatgt gtaccttcct tacccagatc catcaagaat cctaggggcc  15960
ggctgttttg tagatgatat cgtaaaaaca gatggtacac ttatgattga acggttcgtg  16020
tctttagcta tagatgctta cccacttact aaacatccta atcaggagta tgctgatgtc  16080
tttcatttgt acttacaata cataagaaag ctacatgatg agttaacagg acacatgtta  16140
```

-continued gacatgtatt ctgttatgct tactaatgat aacacttcaa ggtattggga acctgagttt 16200
tatgaggcta tgtacacacc gcatacagtc ttacaggctg ttggggcttg tgttctttgc 16260
aattcacaga cttcattaag atgtggtgct tgcatacgta gaccattctt atgttgtaaa 16320
tgctgttacg accatgtcat atcaacatca cataaattag tcttgtctgt taatccgtat 16380
gtttgcaatg ctccaggttg tgatgtcaca gatgtgactc aactttactt aggaggtatg 16440
agctattatt gtaaatcaca taaaccaccc attagttttc cattgtgtgc taatggacaa 16500
gtttttggtt tatataaaaa tacatgtgtt ggtagcgata atgttactga ctttaatgca 16560
attgcaacat gtgactggac aaatgctggt gattacattt tagctaacac ctgtactgaa 16620
agactcaagc tttttgcagc agaaacgctc aaagctactg aggagacatt taaactgtct 16680
tatggtattg ctactgtacg tgaagtgctg tctgacagag aattacatct ttcatgggaa 16740
gttggtaaac ctagaccacc acttaaccga aattatgtct ttactggtta tcgtgtaact 16800
aaaaacagta aagtacaaat aggagagtac acctttgaaa aaggtgacta tggtgatgct 16860
gttgtttacc gaggtacaac aacttacaaa ttaaatgttg gtgattattt tgtgctgaca 16920
tcacatacag taatgccatt aagtgcacct acactagtgc cacaagagca ctatgttaga 16980
attactggct tatacccaac actcaatatc tcagatgagt tttctagcaa tgttgcaaat 17040
tatcaaaagg ttggtatgca aaagtattct acactccagg gaccacctgg tactggtaag 17100
agtcattttg ctattggcct agctctctac tacccttctg ctcgcatagt gtatacagct 17160
tgctctcatg ccgctgttga tgcactatgt gagaaggcat taaaatattt gcctatagat 17220
aaatgtagta gaattatacc tgcacgtgct cgtgtagagt gttttgataa attcaaagtg 17280
aattcaacat tagaacagta tgtcttttgt actgtaaatg cattgcctga gacgacagca 17340
gatatagttg tctttgatga aatttcaatg gccacaaatt atgatttgag tgttgtcaat 17400
gccagattac gtgctaagca ctatgtgtac attggcgacc ctgctcaatt acctgcacca 17460
cgcacattgc taactaaggg cacactagaa ccagaatatt tcaattcagt gtgtagactt 17520
atgaaaacta taggtccaga catgttcctc ggaacttgtc ggcgttgtcc tgctgaaatt 17580
gttgacactg tgagtgcttt ggtttatgat aataagctta aagcacataa agacaaatca 17640
gctcaatgct ttaaaatgtt ttataagggt gttatcacgc atgatgtttc atctgcaatt 17700
aacaggccac aaataggcgt ggtaagagaa ttccttacac gtaaccctgc ttggagaaaa 17760
gctgtcttta tttcacctta taattcacag aatgctgtag cctcaaagat tttgggacta 17820
ccaactcaaa ctgttgattc atcacagggc tcagaatatg actatgtcat attcactcaa 17880
accactgaaa cagctcactc ttgtaatgta aacagattta atgttgctat taccagagca 17940
aaagtaggca tactttgcat aatgtctgat agagaccttt atgacaagtt gcaatttaca 18000
agtcttgaaa ttccacgtag gaatgtggca actttacaag ctgaaaatgt aacaggactc 18060
tttaaagatt gtagtaaggt aatcactggg ttacatccta cacaggcacc tacacacctc 18120
agtgttgaca ctaaattcaa aactgaaggt ttatgtgttg acatacctgg catacctaag 18180
gacatgacct atagaagact catctctatg atgggtttta aaatgaatta tcaagttaat 18240
ggttacccta acatgtttat cacccgcgaa gaagctataa gacatgtacg tgcatggatt 18300
ggcttcgatg tcgaggggtg tcatgctact agagaagctg ttggtaccaa tttaccttta 18360
cagctaggtt tttctacagg tgttaaccta gttgctgtac ctacaggtta tgttgataca 18420
cctaataata cagatttttc cagagttagt gctaaaccac cgcctggaga tcaatttaaa 18480

-continued

```
caccctcatac cacttatgta caaaggactt ccttggaatg tagtgcgtat aaagattgta  18540
caaatgttaa gtgacacact taaaaatctc tctgacagag tcgtatttgt cttatgggca  18600
catggctttg agttgacatc tatgaagtat tttgtgaaaa taggacctga gcgcacctgt  18660
tgtctatgtg atagacgtgc cacatgcttt tccactgctt cagacactta tgcctgttgg  18720
catcattcta ttggatttga ttacgtctat aatccgttta tgattgatgt tcaacaatgg  18780
ggttttacag gtaacctaca aagcaaccat gatctgtatt gtcaagtcca tggtaatgca  18840
catgtagcta gttgtgatgc aatcatgact aggtgtctag ctgtccacga gtgctttgtt  18900
aagcgtgttg actggactat tgaatatcct ataattggtg atgaactgaa gattaatgcg  18960
gcttgtagaa aggttcaaca catggttgtt aaagctgcat tattagcaga caaattccca  19020
gttcttcacg acattggtaa ccctaaagct attaagtgtg tacctcaagc tgatgtagaa  19080
tggaagttct atgatgcaca gccttgtagt gacaaagctt ataaaataga agaattattc  19140
tattcttatg ccacacattc tgacaaattc acagatggtg tatgcctatt ttggaattgc  19200
aatgtcgata gatatcctgc taattccatt gtttgtagat ttgacactag agtgctatct  19260
aaccttaact tgcctggttg tgatggtggc agtttgtatg taaataaaca tgcattccac  19320
acaccagctt ttgataaaag tgcttttgtt aatttaaaac aattaccatt tttctattac  19380
tctgacagtc catgtgagtc tcatggaaaa caagtagtgt cagatataga ttatgtacca  19440
ctaaagtctg ctacgtgtat aacacgttgc aatttaggtg gtgctgtctg tagacatcat  19500
gctaatgagt acagattgta tctcgatgct tataacatga tgatctcagc tggctttagc  19560
ttgtgggttt acaaacaatt tgatacttat aacctctgga acacttttac aagacttcag  19620
agtttagaaa atgtggcttt taatgttgta aataagggac actttgatgg acaacagggt  19680
gaagtaccag tttctatcat taataacact gtttacacaa aagttgatgg tgttgatgta  19740
gaattgtttg aaaataaaac aacattacct gttaatgtag catttgagct ttgggctaag  19800
cgcaacatta aaccagtacc agaggtgaaa atactcaata atttgggtgt ggacattgct  19860
gctaatactg tgatctggga ctacaaaaga gatgctccag cacatatatc tactattggt  19920
gtttgttcta tgactgacat agccaagaaa ccaactgaaa cgatttgtgc accactcact  19980
gtcttttttg atggtagagt tgatggtcaa gtagacttat ttagaaatgc ccgtaatggt  20040
gttcttatta cagaaggtag tgttaaaggt ttacaaccat ctgtaggtcc caaacaagct  20100
agtcttaatg gagtcacatt aattggagaa gccgtaaaaa cacagttcaa ttattataag  20160
aaagttgatg gtgttgtcca acaattacct gaaacttact ttactcagag tagaaattta  20220
caagaattta aacccaggag tcaaatggaa attgatttct tagaattagc tatggatgaa  20280
ttcattgaac ggtataaatt agaaggctat gccttcgaac atatcgttta tggagatttt  20340
agtcatagtc agttaggtgg tttacatcta ctgattggac tagctaaacg ttttaaggaa  20400
tcacctttg aattagaaga ttttattcct atggacagta cagttaaaaa ctatttcata  20460
acagatgcgc aaacaggttc atctaagtgt gtgtgttctg ttattgattt attacttgat  20520
gattttgttg aaataataaa atcccaagat ttatctgtag tttctaaggt tgtcaaagtg  20580
actattgact atacagaaat ttcatttatg ctttggtgta aagatggcca tgtagaaaca  20640
ttttacccaa aattacaatc tagtcaagcg tggcaaccgg gtgttgctat gcctaatctt  20700
tacaaaatgc aaagaatgct attagaaaag tgtgaccttc aaaattatgg tgatagtgca  20760
acattaccta aaggcataat gatgaatgtc gcaaaatata ctcaactgtg tcaatattta  20820
aacacattaa cattagctgt accctataat atgagagtta tacattttgg tgctggttct  20880
```

```
gataaaggag ttgcaccagg tacagctgtt ttaagacagt ggttgcctac gggtacgctg  20940
cttgtcgatt cagatcttaa tgactttgtc tctgatgcag attcaacttt gattggtgat  21000
tgtgcaactg tacatacagc taataaatgg gatctcatta ttagtgatat gtacgaccct  21060
aagactaaaa atgttacaaa agaaaatgac tctaaagagg gtttttcac ttacatttgt  21120
gggtttatac aacaaaagct agctcttgga ggttccgtgg ctataaagat aacagaacat  21180
tcttggaatg ctgatcttta taagctcatg ggacacttcg catggtggac agcctttgtt  21240
actaatgtga atgcgtcatc atctgaagca tttttaattg gatgtaatta tcttggcaaa  21300
ccacgcgaac aaatagatgg ttatgtcatg catgcaaatt acatattttg gaggaataca  21360
aatccaattc agttgtcttc ctattcttta tttgacatga gtaaatttcc ccttaaatta  21420
aggggtactg ctgttatgtc tttaaaagaa ggtcaaatca atgatatgat tttatctctt  21480
cttagtaaag gtagacttat aattagagaa aacaacagag ttgttatttc tagtgatgtt  21540
cttgttaaca actaaacgaa caatgtttgt ttttcttgtt ttattgccac tagtctctag  21600
tcagtgtgtt aatcttacaa ccagaactca attacccct gcatacacta attctttcac  21660
acgtggtgtt tattaccctg acaaagtttt cagatcctca gttttacatt caactcagga  21720
cttgttctta cctttctttt ccaatgttac ttggttccat gctatacatg tctctgggac  21780
caatggtact aagaggtttg ataaccctgt cctaccattt aatgatggtg tttattttgc  21840
ttccactgag aagtctaaca taataagagg ctggattttt ggtactactt tagattcgaa  21900
gacccagtcc ctacttattg ttaataacgc tactaatgtt gttattaaag tctgtgaatt  21960
tcaattttgt aatgatccat ttttgggtgt ttattaccac aaaaacaaca aaagttggat  22020
ggaaagtgag ttcagagttt attctagtgc gaataattgc acttttgaat atgtctctca  22080
gccttttctt atggaccttg aaggaaaaca gggtaatttc aaaaatctta gggaatttgt  22140
gtttaagaat attgatggtt attttaaaat atattctaag cacacgccta ttaatttagt  22200
gcgtgatctc cctcagggtt tttcggcttt agaaccattg gtagatttgc caataggtat  22260
taacatcact aggtttcaaa ctttacttgc tttacataga agttatttga ctcctggtga  22320
ttcttcttca ggttggacag ctggtgctgc agcttattat gtgggttatc ttcaacctag  22380
gacttttcta ttaaaatata atgaaaatgg aaccattaca gatgctgtag actgtgcact  22440
tgaccctctc tcagaaacaa agtgtacgtt gaaatccttc actgtagaaa aaggaatcta  22500
tcaaacttct aactttagag tccaaccaac agaatctatt gttagatttc ctaatattac  22560
aaacttgtgc ccttttggtg aagtttttaa cgccaccaga tttgcatctg tttatgcttg  22620
gaacaggaag agaatcagca actgtgttgc tgattattct gtcctatata attccgcatc  22680
attttccact tttaagtgtt atggagtgtc tcctactaaa ttaaatgatc tctgctttac  22740
taatgtctat gcagattcat ttgtaattag aggtgatgaa gtcagacaaa tcgctccagg  22800
gcaaactgga aagattgctg attataatta taaattacca gatgatttta caggctgcgt  22860
tatagcttgg aattctaaca atcttgattc taaggttggt ggtaattata attacctgta  22920
tagattgttt aggaagtcta atctcaaacc ttttgagaga gatatttcaa ctgaaatcta  22980
tcaggccggt agcacacctt gtaatggtgt tgaaggtttt aattgttact ttcctttaca  23040
atcatatggt ttccaaccca ctaatggtgt tggttaccaa ccatacagag tagtagtact  23100
ttcttttgaa cttctacatg caccagcaac tgtttgtgga cctaaaaagt ctactaattt  23160
ggttaaaaac aaatgtgtca atttcaactt caatggttta acaggcacag gtgttcttac  23220
```

tgagtctaac aaaaagtttc tgcctttcca acaatttggc agagacattg ctgacactac 23280
tgatgctgtc cgtgatccac agacacttga gattcttgac attacaccat gttcttttgg 23340
tggtgtcagt gttataacac caggaacaaa tacttctaac caggttgctg ttctttatca 23400
ggatgttaac tgcacagaag tccctgttgc tattcatgca gatcaactta ctcctacttg 23460
gcgtgtttat tctacaggtt ctaatgtttt tcaaacacgt gcaggctgtt taatagggc 23520 tgaacatgtc aacaactcat atgagtgtga catacccatt ggtgcaggta tatgcgctag 23580
ttatcagact cagactaatt ctcctcggcg ggcacgtagt gtagctagtc aatccatcat 23640
tgcctacact atgtcacttg gtgcagaaaa ttcagttgct tactctaata actctattgc 23700
catacccaca aattttacta ttagtgttac cacagaaatt ctaccagtgt ctatgaccaa 23760
gacatcagta gattgtacaa tgtacatttg tggtgattca actgaatgca gcaatctttt 23820
gttgcaatat ggcagttttt gtacacaatt aaaccgtgct ttaactggaa tagctgttga 23880
acaagacaaa aacacccaag aagtttttgc acaagtcaaa caaatttaca aaacaccacc 23940
aattaaagat tttggtggtt ttaatttttc acaaatatta ccagatccat caaaaccaag 24000
caagaggtca tttattgaag atctactttt caacaaagtg acacttgcag atgctggctt 24060
catcaaacaa tatggtgatt gccttggtga tattgctgct agagacctca tttgtgcaca 24120
aaagtttaac ggccttactg ttttgccacc tttgctcaca gatgaaatga ttgctcaata 24180
cacttctgca ctgttagcgg gtacaatcac ttctggttgg acctttggtg caggtgctgc 24240
attacaaata ccatttgcta tgcaaatggc ttataggttt aatggtattg gagttacaca 24300
gaatgttctc tatgagaacc aaaaattgat tgccaaccaa tttaatagtg ctattggcaa 24360
aattcaagac tcactttctt ccacagcaag tgcacttgga aaacttcaag atgtggtcaa 24420
ccaaaatgca caagctttaa acacgcttgt taaacaactt agctccaatt ttggtgcaat 24480
ttcaagtgtt ttaaatgata tcctttcacg tcttgacaaa gttgaggctg aagtgcaaat 24540
tgataggttg atcacaggca gacttcaaag tttgcagaca tatgtgactc aacaattaat 24600
tagagctgca gaaatcagag cttctgctaa tcttgctgct actaaaatgt cagagtgtgt 24660
acttggacaa tcaaaaagag ttgatttttg tggaaagggc tatcatctta tgtccttccc 24720
tcagtcagca cctcatggtg tagtcttctt gcatgtgact tatgtccctg cacaagaaaa 24780
gaacttcaca actgctcctg ccatttgtca tgatggaaaa gcacactttc ctcgtgaagg 24840
tgtctttgtt tcaaatggca cacactggtt tgtaacacaa aggaattttt atgaaccaca 24900
aatcattact acagacaaca catttgtgtc tggtaactgt gatgttgtaa taggaattgt 24960
caacaacaca gtttatgatc ctttgcaacc tgaattagac tcattcaagg aggagttaga 25020
taaatatttt aagaatcata catcaccaga tgttgattta ggtgacatct ctggcattaa 25080
tgcttcagtt gtaaacattc aaaaagaaat tgaccgcctc aatgaggttg ccaagaattt 25140
aaatgaatct ctcatcgatc tccaagaact tggaaagtat gagcagtata taaaatggcc 25200
atggtacatt tggctaggtt ttatagctgg cttgattgcc atagtaatgg tgacaattat 25260
gctttgctgt atgaccagtt gctgtagttg tctcaagggc tgttgttctt gtggatcctg 25320
ctgcaaattt gatgaagacg actctgagcc agtgctcaaa ggagtcaaat tacattacac 25380
ataaacgaac ttatggattt gtttatgaga atcttcacaa ttggaactgt aactttgaag 25440
caaggtgaaa tcaaggatgc tactccttca gattttgttc gcgctactgc aacgataccg 25500
atacaagcct cactcccttt cggatggctt attgttggcg ttgcacttct tgctgttttt 25560
cagagcgctt ccaaaatcat aaccctcaaa aagagatggc aactagcact ctccaagggt 25620

```
gttcactttg tttgcaactt gctgttgttg tttgtaacag tttactcaca ccttttgctc  25680
gttgctgctg gccttgaagc cccttttctc tatctttatg ctttagtcta cttcttgcag  25740
agtataaact ttgtaagaat aataatgagg ctttggcttt gctggaaatg ccgttccaaa  25800
aacccattac tttatgatgc caactatttt ctttgctggc atactaattg ttacgactat  25860
tgtatacctt acaatagtgt aacttcttca attgtcatta cttcaggtga tggcacaaca  25920
agtcctattt ctgaacatga ctaccagatt ggtggttata ctgaaaaatg ggaatctgga  25980
gtaaaagact gtgttgtatt acacagttac ttcacttcag actattacca gctgtactca  26040
actcaattga gtacagacac tggtgttgaa catgttacct tcttcatcta caataaaatt  26100
gttgatgagc ctgaagaaca tgtccaaatt cacacaatcg acggttcatc cggagttgtt  26160
aatccagtaa tggaaccaat ttatgatgaa ccgacgacga ctactagcgt gcctttgtaa  26220
gcacaagctg atgagtacga acttatgtac tcattcgttt cggaagagac aggtacgtta  26280
atagttaata gcgtacttct ttttcttgct ttcgtggtat tcttgctagt tacactagcc  26340
atccttactg cgcttcgatt gtgtgcgtac tgctgcaata ttgttaacgt gagtcttgta  26400
aaaccttctt tttacgttta ctctcgtgtt aaaaatctga attcttctag agttcctgat  26460
cttctggtct aaacgaacta aatattatat tagtttttct gtttggaact ttaattttag  26520
ccatggcaga ttccaacggt actattaccg ttgaagagct taaaaagctc cttgaacaat  26580
ggaacctagt aataggtttc ctattcctta catggatttg tcttctacaa tttgcctatg  26640
ccaacaggaa taggtttttg tatataatta agttaatttt cctctggctg ttatggccag  26700
taactttagc ttgttttgtg cttgctgctg tttacagaat aaattggatc accggtggaa  26760
ttgctatcgc aatggcttgt cttgtaggct tgatgtggct cagctacttc attgcttctt  26820
tcagactgtt tgcgcgtacg cgttccatgt ggtcattcaa tccagaaact aacattcttc  26880
tcaacgtgcc actccatggc actattctga ccagaccgct tctagaaagt gaactcgtaa  26940
tcggagctgt gatccttcgt ggacatcttc gtattgctgg acaccatcta ggacgctgtg  27000
acatcaagga cctgcctaaa gaaatcactg ttgctacatc acgaacgctt tcttattaca  27060
aattgggagc ttcgcagcgt gtagcaggtg actcaggttt tgctgcatac agtcgctaca  27120
ggattggcaa ctataaatta aacacagacc attccagtag cagtgacaat attgctttgc  27180
ttgtacagta agtgacaaca gatgtttcat ctcgttgact ttcaggttac tatagcagag  27240
atattactaa ttattatgag gacttttaaa gtttccattt ggaatcttga ttacatcata  27300
aacctcataa ttaaaaattt atctaagtca ctaactgaga ataaatattc tcaattagat  27360
gaagagcaac caatggagat tgattaaacg aacatgaaaa ttattctttt cttggcactg  27420
ataacactcg ctacttgtga gctttatcac taccaagagt gtgttagagg tacaacagta  27480
cttttaaaag aaccttgctc ttctggaaca tacgagggca attcaccatt tcatcctcta  27540
gctgataaca aatttgcact gacttgcttt agcactcaat ttgcttttgc ttgtcctgac  27600
ggcgtaaaac acgtctatca gttacgtgcc agatcagttt cacctaaact gttcatcaga  27660
caagaggaag ttcaagaact ttactctcca atttttctta ttgttgcggc aatagtgttt  27720
ataacacttt gcttcacact caaaagaaag acagaatgat tgaactttca ttaattgact  27780
tctatttgtg ctttttagcc tttctgctat tccttgtttt aattatgctt attatctttt  27840
ggttctcact tgaactgcaa gatcataatg aaacttgtca cgcctaaacg aacatgaaat  27900
ttcttgtttt cttaggaatc atcacaactg tagctgcatt tcaccaagaa tgtagtttac  27960
```

-continued agtcatgtac tcaacatcaa ccatatgtag ttgatgaccc gtgtcctatt cacttctatt 28020
ctaaatggta tattagagta ggagctagaa aatcagcacc tttaattgaa ttgtgcgtgg 28080
atgaggctgg ttctaaatca cccattcagt acatcgatat cggtaattat acagtttcct 28140
gttcaccttt tacaattaat tgccaggaac ctaaattggg tagtcttgta gtgcgttgtt 28200
cgttctatga agacttttta gagtatcatg acgttcgtgt tgttttagat ttcatctaaa 28260
cgaacaaact aaaatgtctg ataatggacc ccaaaatcag cgaaatgcac cccgcattac 28320
gtttggtgga ccctcagatt caactggcag taaccagaat ggagaacgca gtggggcgcg 28380
atcaaaacaa cgtcggcccc aaggtttacc caataatact gcgtcttggt tcaccgctct 28440
cactcaacat ggcaaggaag accttaaatt ccctcgagga caaggcgttc caattaacac 28500
caatagcagt ccagatgacc aaattggcta ctaccgaaga gctaccagac gaattcgtgg 28560
tggtgacggt aaaatgaaag atctcagtcc aagatggtat ttctactacc taggaactgg 28620
gccagaagct ggacttccct atggtgctaa caaagacggc atcatatggg ttgcaactga 28680
gggagccttg aatacaccaa aagatcacat tggcacccgc aatcctgcta acaatgctgc 28740
aatcgtgcta caacttcctc aaggaacaac attgccaaaa ggcttctacg cagaagggag 28800
cagaggcggc agtcaagcct cttctcgttc ctcatcacgt agtcgcaaca gttcaagaaa 28860
ttcaactcca ggcagcagta ggggaacttc tcctgctaga atggctggca atggcggtga 28920
tgctgctctt gctttgctgc tgcttgacag attgaaccag cttgagagca aaatgtctgg 28980
taaaggccaa caacaacaag gccaaactgt cactaagaaa tctgctgctg aggcttctaa 29040
gaagcctcgg caaaaacgta ctgccactaa agcatacaat gtaacacaag cttttggcag 29100
acgtggtcca gaacaaaccc aaggaaattt tggggaccag gaactaatca gacaaggaac 29160
tgattacaaa cattggccgc aaattgcaca atttgccccc agcgcttcag cgttcttcgg 29220
aatgtcgcgc attggcatgg aagtcacacc ttcgggaacg tggttgacct acacaggtgc 29280
catcaaattg gatgacaaag atccaaattt caaagatcaa gtcattttgc tgaataagca 29340
tattgacgca tacaaaacat tcccaccaac agagcctaaa aaggacaaaa agaagaaggc 29400
tgatgaaact caagccttac cgcagagaca gaagaaacag caaactgtga ctcttcttcc 29460
tgctgcagat ttggatgatt tctccaaaca attgcaacaa tccatgagca gtgctgactc 29520
aactcaggcc taaactcatg cagaccacac aaggcagatg ggctatataa acgttttcgc 29580
ttttccgttt acgatatata gtctactctt gtgcagaatg aattctcgta actacatagc 29640
acaagtagat gtagttaact ttaatctcac atagcaatct ttaatcagtg tgtaacatta 29700
gggaggactt gaaagagcca ccacattttc accgaggcca cgcggagtac gatcgagtgt 29760
acagtgaaca atgctaggga gagctgccta tatggaagag ccctaatgtg taaaattaat 29820
tttagtagtg ctatccccat gtgattttaa tagcttctta ggagaatgac aaaaaaaaaa 29880
aaaaaaaaaa a 29891

<210> SEQ ID NO 6
<211> LENGTH: 29727
<212> TYPE: DNA
<213> ORGANISM: SARS coronavirus Urbani
<300> PUBLICATION INFORMATION:
<308> DATABASE ACCESSION NUMBER: GENBANK / AY278741
<309> DATABASE ENTRY DATE: 2016-07-25
<313> RELEVANT RESIDUES IN SEQ ID NO: (1)..(29727)

<400> SEQUENCE: 6

```
atattaggtt tttacctacc caggaaaagc caaccaacct cgatctcttg tagatctgtt     60
ctctaaacga actttaaaat ctgtgtagct gtcgctcggc tgcatgccta gtgcacctac    120
gcagtataaa caataataaa ttttactgtc gttgacaaga aacgagtaac tcgtccctct    180
tctgcagact gcttacggtt tcgtccgtgt tgcagtcgat catcagcata cctaggtttc    240
gtccgggtgt gaccgaaagg taagatggag agccttgttc ttggtgtcaa cgagaaaaca    300
cacgtccaac tcagtttgcc tgtccttcag gttagagacg tgctagtgcg tggcttcggg    360
gactctgtgg aagaggccct atcggaggca cgtgaacacc tcaaaaatgg cacttgtggt    420
ctagtagagc tggaaaaagg cgtactgccc cagcttgaac agccctatgt gttcattaaa    480
cgttctgatg ccttaagcac caatcacggc cacaaggtcg ttgagctggt tgcagaaatg    540
gacggcattc agtacggtcg tagcggtata acactgggag tactcgtgcc acatgtgggc    600
gaaaccccaa ttgcataccg caatgttctt cttcgtaaga acggtaataa gggagccggt    660
ggtcatagct atggcatcga tctaaagtct tatgacttag gtgacgagct tggcactgat    720
cccattgaag attatgaaca aaactggaac actaagcatg gcagtggtgc actccgtgaa    780
ctcactcgtg agctcaatgg aggtgcagtc actcgctatg tcgacaacaa tttctgtggc    840
ccagatgggt accctcttga ttgcatcaaa gattttctcg cacgcgcggg caagtcaatg    900
tgcactcttt ccgaacaact tgattacatc gagtcgaaga gaggtgtcta ctgctgccgt    960
gaccatgagc atgaaattgc ctggttcact gagcgctctg ataagagcta cgagcaccag   1020
acacccttcg aaattaagag tgccaagaaa tttgacactt tcaaagggga atgcccaaag   1080
tttgtgtttc ctcttaactc aaaagtcaaa gtcattcaac cacgtgttga aaagaaaaag   1140
actgagggtt tcatggggcg tatacgctct gtgtaccctg ttgcatctcc acaggagtgt   1200
aacaatatgc acttgtctac cttgatgaaa tgtaatcatt gcgatgaagt ttcatggcag   1260
acgtgcgact ttctgaaagc cacttgtgaa cattgtggca ctgaaaattt agttattgaa   1320
ggacctacta catgtgggta cctacctact aatgctgtag tgaaaatgcc atgtcctgcc   1380
tgtcaagacc cagagattgg acctgagcat agtgttgcag attatcacaa ccactcaaac   1440
attgaaactc gactccgcaa gggaggtagg actagatgtt ttggaggctg tgtgtttgcc   1500
tatgttggct gctataataa gcgtgcctac tgggttcctc gtgctagtgc tgatattggc   1560
tcaggccata ctggcattac tggtgacaat gtggagacct tgaatgagga tctccttgag   1620
atactgagtc gtgaacgtgt taacattaac attgttggcg attttcattt gaatgaagag   1680
gttgccatca ttttggcatc tttctctgct tctacaagtg cctttattga cactataaag   1740
agtcttgatt acaagtcttt caaaaccatt gttgagtcct gcggtaacta taaagttacc   1800
aagggaaagc ccgtaaaagg tgcttggaac attggacaac agagatcagt tttaacacca   1860
ctgtgtggtt ttccctcaca ggctgctggt gttatcagat caatttttgc gcgcacactt   1920
gatgcagcaa accactcaat tcctgatttg caaagagcag ctgtcaccat acttgatggt   1980
atttctgaac agtcattacg tcttgtcgac gccatggttt atacttcaga cctgctcacc   2040
aacagtgtca ttattatggc atatgtaact ggtggtcttg tacaacagac ttctcagtgg   2100
ttgtctaatc ttttgggcac tactgttgaa aaactcaggc ctatctttga atggattgag   2160
gcgaaactta gtgcaggagt tgaatttctc aaggatgctt gggagattct caaatttctc   2220
attacaggtg tttttgacat cgtcaagggt caaatacagg ttgcttcaga taacatcaag   2280
```

-continued

```
gattgtgtaa aatgcttcat tgatgttgtt aacaaggcac tcgaaatgtg cattgatcaa   2340
gtcactatcg ctggcgcaaa gttgcgatca ctcaacttag gtgaagtctt catcgctcaa   2400
agcaagggac tttaccgtca gtgtatacgt ggcaaggagc agctgcaact actcatgcct   2460
cttaaggcac caaaagaagt aacctttctt gaaggtgatt cacatgacac agtacttacc   2520
tctgaggagg ttgttctcaa gaacggtgaa ctcgaagcac tcgagacgcc cgttgatagc   2580
ttcacaaatg gagctatcgt tggcacacca gtctgtgtaa atggcctcat gctcttagag   2640
attaaggaca aagaacaata ctgcgcattg tctcctggtt tactggctac aaacaatgtc   2700
tttcgcttaa aagggggtgc accaattaaa ggtgtaacct ttggagaaga tactgtttgg   2760
gaagttcaag gttacaagaa tgtgagaatc acatttgagc ttgatgaacg tgttgacaaa   2820
gtgcttaatg aaaagtgctc tgtctacact gttgaatccg gtaccgaagt tactgagttt   2880
gcatgtgttg tagcagaggc tgttgtgaag actttacaac cagtttctga tctccttacc   2940
aacatgggta ttgatcttga tgagtggagt gtagctacat tctacttatt tgatgatgct   3000
ggtgaagaaa acttttcatc acgtatgtat tgttcctttt accctccaga tgaggaagaa   3060
gaggacgatg cagagtgtga ggaagaagaa attgatgaaa cctgtgaaca tgagtacggt   3120
acagaggatg attatcaagg tctccctctg gaatttggtg cctcagctga aacagttcga   3180
gttgaggaag aagaagagga agactggctg gatgatacta ctgagcaatc agagattgag   3240
ccagaaccag aacctacacc tgaagaacca gttaatcagt ttactggtta tttaaaactt   3300
actgacaatg ttgccattaa atgtgttgac atcgttaagg aggcacaaag tgctaatcct   3360
atggtgattg taaatgctgc taacatacac ctgaaacatg gtggtggtgt agcaggtgca   3420
ctcaacaagg caaccaatgg tgccatgcaa aaggagagtg atgattacat taagctaaat   3480
ggccctctta cagtaggagg gtcttgtttg ctttctggac ataatcttgc taagaagtgt   3540
ctgcatgttg ttggacctaa cctaaatgca ggtgaggaca tccagcttct taaggcagca   3600
tatgaaaatt tcaattcaca ggacatctta cttgcaccat tgttgtcagc aggcatattt   3660
ggtgctaaac cacttcagtc tttacaagtg tgcgtgcaga cggttcgtac acaggtttat   3720
attgcagtca atgacaaagc tctttatgag caggttgtca tggattatct tgataacctg   3780
aagcctagag tggaagcacc taaacaagag gagccaccaa acacagaaga ttccaaaact   3840
gaggagaaat ctgtcgtaca gaagcctgtc gatgtgaagc caaaaattaa ggcctgcatt   3900
gatgaggtta ccacaacact ggaagaaact aagtttctta ccaataagtt actcttgttt   3960
gctgatatca atggtaagct ttaccatgat tctcagaaca tgcttagagg tgaagatatg   4020
tctttccttg agaaggatgc accttacatg gtaggtgatg ttatcactag tggtgatatc   4080
acttgtgttg taataccctc caaaaaggct ggtggcacta ctgagatgct ctcaagagct   4140
ttgaagaaag tgccagttga tgagtatata accacgtacc ctggacaagg atgtgctggt   4200
tatacacttg aggaagctaa gactgctctt aagaaatgca aatctgcatt ttatgtacta   4260
ccttcagaag cacctaatgc taaggaagag attctaggaa ctgtatcctg gaatttgaga   4320
gaaatgcttg ctcatgctga agagacaaga aaattaatgc ctatatgcat ggatgttaga   4380
gccataatgg caaccatcca acgtaagtat aaaggaatta aaattcaaga gggcatcgtt   4440
gactatggtg tccgattctt cttttatact agtaaagagc ctgtagcttc tattattacg   4500
aagctgaact ctctaaatga gccgcttgtc acaatgccaa ttggttatgt gacacatggt   4560
tttaatcttg aagaggctgc gcgctgtatg cgttctctta aagctcctgc cgtagtgtca   4620
gtatcatcac cagatgctgt tactacatat aatggatacc tcacttcgtc atcaaagaca   4680
```

-continued

```
tctgaggagc actttgtaga aacagtttct ttggctggct cttacagaga ttggtcctat   4740
tcaggacagc gtacagagtt aggtgttgaa tttcttaagc gtggtgacaa aattgtgtac   4800
cacactctgg agagccccgt cgagtttcat cttgacggtg aggttctttc acttgacaaa   4860
ctaaagagtc tcttatccct gcgggaggtt aagactataa aagtgttcac aactgtggac   4920
aacactaatc tccacacaca gcttgtggat atgtctatga catatggaca gcagtttggt   4980
ccaacatact tggatggtgc tgatgttaca aaaattaaac ctcatgtaaa tcatgagggt   5040
aagactttct ttgtactacc tagtgatgac acactacgta gtgaagcttt cgagtactac   5100
catactcttg atgagagttt tcttggtagg tacatgtctg ctttaaacca cacaaagaaa   5160
tggaaatttc ctcaagttgg tggtttaact tcaattaaat gggctgataa caattgttat   5220
ttgtctagtg ttttattagc acttcaacag cttgaagtca aattcaatgc accagcactt   5280
caagaggctt attatagagc ccgtgctggt gatgctgcta acttttgtgc actcatactc   5340
gcttacagta ataaaactgt tggcgagctt ggtgatgtca gagaaactat gacccatctt   5400
ctacagcatg ctaatttgga atctgcaaag cgagttctta atgtggtgtg taaacattgt   5460
ggtcagaaaa ctactacctt aacgggtgta gaagctgtga tgtatatggg tactctatct   5520
tatgataatc ttaagacagg tgtttccatt ccatgtgtgt gtggtcgtga tgctacacaa   5580
tatctagtac aacaagagtc ttcttttgtt atgatgtctg caccacctgc tgagtataaa   5640
ttacagcaag gtacattctt atgtgcgaat gagtacactg gtaactatca gtgtggtcat   5700
tacactcata taactgctaa ggagaccctc tatcgtattg acggagctca ccttacaaag   5760
atgtcagagt acaaaggacc agtgactgat gttttctaca aggaaacatc ttacactaca   5820
accatcaagc ctgtgtcgta taaactcgat ggagttactt acacagagat tgaaccaaaa   5880
ttggatgggt attataaaaa ggataatgct tactatacag agcagcctat agaccttgta   5940
ccaactcaac cattaccaaa tgcgagtttt gataatttca aactcacatg ttctaacaca   6000
aaatttgctg atgatttaaa tcaaatgaca ggcttcacaa agccagcttc acgagagcta   6060
tctgtcacat tcttcccaga cttgaatggc gatgtagtgg ctattgacta tagacactat   6120
tcagcgagtt tcaagaaagg tgctaaatta ctgcataagc caattgtttg gcacattaac   6180
caggctacaa ccaagacaac gttcaaacca aacacttggt gtttacgttg tctttggagt   6240
acaaagccag tagatacttc aaattcattt gaagttctgg cagtagaaga cacacaagga   6300
atggacaatc ttgcttgtga aagtcaacaa cccacctctg aagaagtagt ggaaaatcct   6360
accatacaga aggaagtcat agagtgtgac gtgaaaacta ccgaagttgt aggcaatgtc   6420
atacttaaac catcagatga aggtgttaaa gtaacacaag agttaggtca tgaggatctt   6480
atggctgctt atgtggaaaa cacaagcatt accattaaga aacctaatga gctttcacta   6540
gccttaggtt taaaaacaat tgccactcat ggtattgctg caattaatag tgttccttgg   6600
agtaaaattt tggcttatgt caaaccattc ttaggacaag cagcaattac aacatcaaat   6660
tgcgctaaga gattagcaca acgtgtgttt aacaattata tgccttatgt gtttacatta   6720
ttgttccaat tgtgtacttt tactaaaagt accaattcta gaattagagc ttcactacct   6780
acaactattg ctaaaaatag tgttaagagt gttgctaaat tatgtttgga tgccggcatt   6840
aattatgtga agtcacccaa attttctaaa ttgttcacaa tcgctatgtg gctattgttg   6900
ttaagtattt gcttaggttc tctaatctgt gtaactgctg cttttggtgt actcttatct   6960
aattttggtg ctccttctta ttgtaatggc gttagagaat tgtatcttaa ttcgtctaac   7020
```

-continued

```
gttactacta tggatttctg tgaaggttct tttccttgca gcatttgttt aagtggatta   7080
gactcccttg attcttatcc agctcttgaa accattcagg tgacgatttc atcgtacaag   7140
ctagacttga caattttagg tctggccgct gagtgggttt tggcatatat gttgttcaca   7200
aaattctttt atttattagg tctttcagct ataatgcagg tgttctttgg ctattttgct   7260
agtcatttca tcagcaattc ttggctcatg tggtttatca ttagtattgt acaaatggca   7320
cccgtttctg caatggttag gatgtacatc ttctttgctt ctttctacta catatggaag   7380
agctatgttc atatcatgga tggttgcacc tcttcgactt gcatgatgtg ctataagcgc   7440
aatcgtgcca cacgcgttga gtgtacaact attgttaatg gcatgaagag atctttctat   7500
gtctatgcaa atggaggccg tggcttctgc aagactcaca attggaattg tctcaattgt   7560
gacacatttt gcactggtag tacattcatt agtgatgaag ttgctcgtga tttgtcactc   7620
cagtttaaaa gaccaatcaa ccctactgac cagtcatcgt atattgttga tagtgttgct   7680
gtgaaaaatg gcgcgcttca cctctacttt gacaaggctg gtcaaaagac ctatgagaga   7740
catccgctct cccatttgt caatttagac aatttgagag ctaacaacac taaaggttca   7800
ctgcctatta atgtcatagt tttgatggc aagtccaaat gcgacgagtc tgcttctaag   7860
tctgcttctg tgtactacag tcagctgatg tgccaaccta ttctgttgct tgaccaagtt   7920
cttgtatcag acgttggaga tagtactgaa gtttccgtta agatgtttga tgcttatgtc   7980
gacacctttt cagcaacttt tagtgttcct atggaaaaac ttaaggcact tgttgctaca   8040
gctcacagcg agttagcaaa gggtgtagct ttagatggtg tcctttctac attcgtgtca   8100
gctgcccgac aaggtgttgt tgataccgat gttgacacaa aggatgttat tgaatgtctc   8160
aaactttcac atcactctga cttagaagtg acaggtgaca gttgtaacaa tttcatgctc   8220
acctataata aggttgaaaa catgacgccc agagatcttg gcgcatgtat tgactgtaat   8280
gcaaggcata tcaatgccca agtagcaaaa agtcacaatg tttcactcat ctggaatgta   8340
aaagactaca tgtctttatc tgaacagctg cgtaaacaaa ttcgtagtgc tgccaagaag   8400
aacaacatac cttttagact aacttgtgct acaactagac aggttgtcaa tgtcataact   8460
actaaaatct cactcaaggg tggtaagatt gttagtactt gttttaaact tatgcttaag   8520
gccacattat tgtgcgttct tgctgcattg gtttgttata tcgttatgcc agtacataca   8580
ttgtcaatcc atgatggtta cacaaatgaa atcattggtt acaaagccat tcaggatggt   8640
gtcactcgtg acatcatttc tactgatgat tgttttgcaa ataaacatgc tggttttgac   8700
gcatggttta gccagcgtgg tggttcatac aaaaatgaca aaagctgccc tgtagtagct   8760
gctatcatta caagagagat tggtttcata gtgcctggct taccgggtac tgtgctgaga   8820
gcaatcaatg gtgacttctt gcattttcta cctcgtgttt ttagtgctgt tggcaacatt   8880
tgctacacac cttccaaact cattgagtat agtgattttg ctacctctgc ttgcgttctt   8940
gctgctgagt gtacaatttt taaggatgct atgggcaaac ctgtgccata ttgttatgac   9000
actaatttgc tagagggttc tatttcttat agtgagcttc gtccagacac tcgttatgtg   9060
cttatggatg gttccatcat acagtttcct aacacttacc tggagggttc tgttagagta   9120
gtaacaactt ttgatgctga gtactgtaga catggtacat gcgaaaggtc agaagtaggt   9180
atttgcctat ctaccagtgg tagatgggtt cttaataatg agcattacag agctctatca   9240
ggagttttct gtggtgttga tgcgatgaat ctcatagcta acatctttac tcctcttgtg   9300
caacctgtgg gtgctttaga tgtgtctgct tcagtagtgg ctggtggtat tattgccata   9360
ttggtgactt gtgctgccta ctactttatg aaattcagac gtgtttttgg tgagtacaac   9420
```

```
catgttgttg ctgctaatgc acttttgttt ttgatgtctt tcactatact ctgtctggta   9480
ccagcttaca gctttctgcc gggagtctac tcagtctttt acttgtactt gacattctat   9540
ttcaccaatg atgtttcatt cttggctcac cttcaatggt ttgccatgtt ttctcctatt   9600
gtgccttttt ggataacagc aatctatgta ttctgtattt ctctgaagca ctgccattgg   9660
ttctttaaca actatcttag gaaaagagtc atgtttaatg gagttacatt tagtaccttc   9720
gaggaggctg ctttgtgtac ctttttgctc aacaaggaaa tgtacctaaa attgcgtagc   9780
gagacactgt tgccacttac acagtataac aggtatcttg ctctatataa caagtacaag   9840
tatttcagtg gagccttaga tactaccagc tatcgtgaag cagcttgctg ccacttagca   9900
aaggctctaa atgactttag caactcaggt gctgatgttc tctaccaacc accacagaca   9960
tcaatcactt ctgctgttct gcagagtggt tttaggaaaa tggcattccc gtcaggcaaa  10020
gttgaagggt gcatggtaca agtaacctgt ggaactacaa ctcttaatgg attgtggttg  10080
gatgacacag tatactgtcc aagacatgtc atttgcacag cagaagacat gcttaatcct  10140
aactatgaag atctgctcat tcgcaaatcc aaccatagct ttcttgttca ggctggcaat  10200
gttcaacttc gtgttattgg ccattctatg caaaattgtc tgcttaggct taaagttgat  10260
acttctaacc ctaagacacc caagtataaa tttgtccgta tccaacctgg tcaaacattt  10320
tcagttctag catgctacaa tggttcacca tctggtgttt atcagtgtgc catgagacct  10380
aatcatacca ttaaaggttc tttccttaat ggatcatgtg gtagtgttgg ttttaacatt  10440
gattatgatt gcgtgtcttt ctgctatatg catcatatgg agcttccaac aggagtacac  10500
gctggtactg acttagaagg taaattctat ggtccatttg ttgacagaca aactgcacag  10560
gctgcaggta cagacacaac cataacatta aatgttttgg catggctgta tgctgctgtt  10620
atcaatggtg ataggtggtt tcttaataga ttcaccacta ctttgaatga ctttaacctt  10680
gtggcaatga agtacaacta tgaacctttg acacaagatc atgttgacat attgggacct  10740
ctttctgctc aaacaggaat tgccgtctta gatatgtgtg ctgctttgaa agagctgctg  10800
cagaatggta tgaatggtcg tactatcctt ggtagcacta ttttagaaga tgagtttaca  10860
ccatttgatg ttgttagaca atgctctggt gttaccttcc aaggtaagtt caagaaaatt  10920
gttaagggca ctcatcattg gatgctttta actttcttga catcactatt gattcttgtt  10980
caaagtacac agtggtcact gtttttcttt gtttacgaga atgctttctt gccatttact  11040
cttggtatta tggcaattgc tgcatgtgct atgctgcttg ttaagcataa gcacgcattc  11100
ttgtgcttgt ttctgttacc ttctcttgca acagttgctt actttaatat ggtctacatg  11160
cctgctagct gggtgatgcg tatcatgaca tggcttgaat tggctgacac tagcttgtct  11220
ggttataggc ttaaggattg tgttatgtat gcttcagctt tagttttgct tattctcatg  11280
acagctcgca ctgtttatga tgatgctgct agacgtgttt ggacactgat gaatgtcatt  11340
acacttgttt acaaagtcta ctatggtaat gctttagatc aagctatttc catgtgggcc  11400
ttagttattt ctgtaacctc taactattct ggtgtcgtta cgactatcat gtttttagct  11460
agagctatag tgtttgtgtg tgttgagtat tacccattgt tatttattac tggcaacacc  11520
ttacagtgta tcatgcttgt ttattgtttc ttaggctatt gttgctgctg ctactttggc  11580
cttttctgtt tactcaaccg ttacttcagg cttactcttg gtgtttatga ctacttggtc  11640
tctacacaag aatttaggta tatgaactcc caggggcttt tgcctcctaa gagtagtatt  11700
gatgctttca agcttaacat taagttgttg ggtattggag gtaaaccatg tatcaaggtt  11760
```

-continued gctactgtac agtctaaaat gtctgacgta aagtgcacat ctgtggtact gctctcggtt 11820
cttcaacaac ttagagtaga gtcatcttct aaattgtggg cacaatgtgt acaactccac 11880
aatgatattc ttcttgcaaa agacacaact gaagctttcg agaagatggt ttctcttttg 11940
tctgttttgc tatccatgca gggtgctgta gacattaata ggttgtgcga ggaaatgctc 12000
gataaccgtg ctactcttca ggctattgct tcagaattta gttctttacc atcatatgcc 12060
gcttatgcca ctgcccagga ggcctatgag caggctgtag ctaatggtga ttctgaagtc 12120
gttctcaaaa agttaaagaa atctttgaat gtggctaaat ctgagtttga ccgtgatgct 12180
gccatgcaac gcaagttgga aaagatggca gatcaggcta tgacccaaat gtacaaacag 12240
gcaagatctg aggacaagag ggcaaaagta actagtgcta tgcaaacaat gctcttcact 12300
atgcttagga agcttgataa tgatgcactt aacaacatta tcaacaatgc gcgtgatggt 12360
tgtgttccac tcaacatcat accattgact acagcagcca aactcatggt tgttgtccct 12420
gattatggta cctacaagaa cacttgtgat ggtaacacct ttacatatgc atctgcactc 12480
tgggaaatcc agcaagttgt tgatgcggat agcaagattg ttcaacttag tgaaattaac 12540
atggacaatt caccaaattt ggcttggcct cttattgtta cagctctaag agccaactca 12600
gctgttaaac tacagaataa tgaactgagt ccagtagcac tacgacagat gtcctgtgcg 12660
gctggtacca cacaaacagc ttgtactgat gacaatgcac ttgcctacta taacaattcg 12720
aagggaggta ggtttgtgct ggcattacta tcagaccacc aagatctcaa atgggctaga 12780
ttccctaaga gtgatggtac aggtacaatt tacacagaac tggaaccacc ttgtaggttt 12840
gttacagaca caccaaaagg gcctaaagtg aaatacttgt acttcatcaa aggcttaaac 12900
aacctaaata gaggtatggt gctgggcagt ttagctgcta cagtacgtct tcaggctgga 12960
aatgctacag aagtacctgc caattcaact gtgctttcct tctgtgcttt tgcagtagac 13020
cctgctaaag catataagga ttacctagca agtggaggac aaccaatcac caactgtgtg 13080
aagatgttgt gtacacacac tggtacagga caggcaatta ctgtaacacc agaagctaac 13140
atggaccaag agtcctttgg tggtgcttca tgttgtctgt attgtagatg ccacattgac 13200
catccaaatc ctaaaggatt ctgtgacttg aaaggtaagt acgtccaaat acctaccact 13260
tgtgctaatg acccagtggg ttttacactt agaaacacag tctgtaccgt ctgcggaatg 13320
tggaaaggtt atggctgtag ttgtgaccaa ctccgcgaac ccttgatgca gtctgcggat 13380
gcatcaacgt tttaaacgg gtttgcggtg taagtgcagc ccgtcttaca ccgtgcggca 13440
caggcactag tactgatgtc gtctacaggg cttttgatat ttacaacgaa aaagttgctg 13500
gttttgcaaa gttcctaaaa actaattgct gtcgcttcca ggagaaggat gaggaaggca 13560
atttattaga ctcttacttt gtagttaaga ggcatactat gtctaactac caacatgaag 13620
agactattta taacttggtt aaagattgtc cagcggttgc tgtccatgac tttttcaagt 13680
ttagagtaga tggtgacatg gtaccacata tatcacgtca gcgtctaact aaatacacaa 13740
tggctgattt agtctatgct ctacgtcatt ttgatgaggg taattgtgat acattaaaag 13800
aaatactcgt cacatacaat tgctgtgatg atgattattt caataagaag gattggtatg 13860
acttcgtaga gaatcctgac atcttacgcg tatatgctaa cttaggtgag cgtgtacgcc 13920
aatcattatt aaagactgta caattctgcg atgctatgcg tgatgcaggc attgtaggcg 13980
tactgacatt agataatcag gatcttaatg ggaactggta cgatttcggt gatttcgtac 14040
aagtagcacc aggctgcgga gttcctattg tggattcata ttactcattg ctgatgccca 14100
tcctcacttt gactagggca ttggctgctg agtcccatat ggatgctgat ctcgcaaaac 14160

-continued

```
cacttattaa gtgggatttg ctgaaatatg attttacgga agagagactt tgtctcttcg  14220
accgttattt taaatattgg gaccagacat accatcccaa ttgtattaac tgtttggatg  14280
ataggtgtat ccttcattgt gcaaacttta atgtgttatt ttctactgtg tttccaccta  14340
caagttttgg accactagta agaaaaatat ttgtagatgg tgttcctttt gttgtttcaa  14400
ctggatacca ttttcgtgag ttaggagtcg tacataatca ggatgtaaac ttacatagct  14460
cgcgtctcag tttcaaggaa cttttagtgt atgctgctga tccagctatg catgcagctt  14520
ctggcaattt attgctagat aaacgcacta catgcttttc agtagctgca ctaacaaaca  14580
atgttgcttt tcaaactgtc aaacccggta attttaataa agacttttat gactttgctg  14640
tgtctaaagg tttctttaag gaaggaagtt ctgttgaact aaaacacttc ttctttgctc  14700
aggatggcaa cgctgctatc agtgattatg actattatcg ttataatctg ccaacaatgt  14760
gtgatatcag acaactccta ttcgtagttg aagttgttga taaatacttt gattgttacg  14820
atggtggctg tattaatgcc aaccaagtaa tcgttaacaa tctggataaa tcagctggtt  14880
tcccatttaa taaatggggt aaggctagac tttattatga ctcaatgagt tatgaggatc  14940
aagatgcact tttcgcgtat actaagcgta atgtcatccc tactataact caaatgaatc  15000
ttaagtatgc cattagtgca aagaatagag ctcgcaccgt agctggtgtc tctatctgta  15060
gtactatgac aaatagacag tttcatcaga aattattgaa gtcaatagcc gccactagag  15120
gagctactgt ggtaattgga acaagcaagt tttacggtgg ctggcataat atgttaaaaa  15180
ctgtttacag tgatgtagaa actccacacc ttatgggttg ggattatcca aaatgtgaca  15240
gagccatgcc taacatgctt aggataatgg cctctcttgt tcttgctcgc aaacataaca  15300
cttgctgtaa cttatcacac cgtttctaca ggttagctaa cgagtgtgcg caagtattaa  15360
gtgagatggt catgtgtggc ggctcactat atgttaaacc aggtggaaca tcatccggtg  15420
atgctacaac tgcttatgct aatagtgtct ttaacatttg tcaagctgtt acagccaatg  15480
taaatgcact tctttcaact gatggtaata agatagctga caagtatgtc cgcaatctac  15540
aacacaggct ctatgagtgt ctctatagaa atagggatgt tgatcatgaa ttcgtggatg  15600
agttttacgc ttacctgcgt aaacatttct ccatgatgat tctttctgat gatgccgttg  15660
tgtgctataa cagtaactat gcggctcaag gtttagtagc tagcattaag aactttaagg  15720
cagttcttta ttatcaaaat aatgtgttca tgtctgaggc aaaatgttgg actgagactg  15780
accttactaa aggacctcac gaattttgct cacagcatac aatgctagtt aaacaaggag  15840
atgattacgt gtacctgcct tacccagatc catcaagaat attaggcgca ggctgttttg  15900
tcgatgatat tgtcaaaaca gatggtacac ttatgattga aaggttcgtg tcactggcta  15960
ttgatgctta cccacttaca aaacatccta atcaggagta tgctgatgtc tttcacttgt  16020
atttacaata cattagaaag ttacatgatg agcttactgg ccacatgttg gacatgtatt  16080
ccgtaatgct aactaatgat aacacctcac ggtactggga acctgagttt tatgaggcta  16140
tgtacacacc acatacagtc ttgcaggctg taggtgcttg tgtattgtgc aattcacaga  16200
cttcacttcg ttgcggtgcc tgtattagga gaccattcct atgttgcaag tgctgctatg  16260
accatgtcat ttcaacatca cacaaattag tgttgtctgt taatccctat gtttgcaatg  16320
ccccaggttg tgatgtcact gatgtgacac aactgtatct aggaggtatg agctattatt  16380
gcaagtcaca taagcctccc attagttttc cattatgtgc taatggtcag gtttttggtt  16440
tatacaaaaa cacatgtgta ggcagtgaca atgtcactga cttcaatgcg atagcaacat  16500
```

-continued

```
gtgattggac taatgctggc gattacatac ttgccaacac ttgtactgag agactcaagc  16560
ttttcgcagc agaaacgctc aaagccactg aggaaacatt taagctgtca tatggtattg  16620
ctactgtacg cgaagtactc tctgacagag aattgcatct ttcatgggag gttggaaaac  16680
ctagaccacc attgaacaga aactatgtct ttactggtta ccgtgtaact aaaaatagta  16740
aagtacagat tggagagtac acctttgaaa aaggtgacta tggtgatgct gttgtgtaca  16800
gaggtactac gacatacaag ttgaatgttg gtgattactt tgtgttgaca tctcacactg  16860
taatgccact tagtgcacct actctagtgc cacaagagca ctatgtgaga attactggct  16920
tgtacccaac actcaacatc tcagatgagt tttctagcaa tgttgcaaat tatcaaaagg  16980
tcggcatgca aaagtactct acactccaag gaccacctgg tactggtaag agtcattttg  17040
ccatcggact tgctctctat tacccatctg ctcgcatagt gtatacggca tgctctcatg  17100
cagctgttga tgccctatgt gaaaaggcat taaaatattt gcccatagat aaatgtagta  17160
gaatcatacc tgcgcgtgcg cgcgtagagt gttttgataa attcaaagtg aattcaacac  17220
tagaacagta tgtttttctgc actgtaaatg cattgccaga aacaactgct gacattgtag  17280
tctttgatga aatctctatg gctactaatt atgacttgag tgttgtcaat gctagacttc  17340
gtgcaaaaca ctacgtctat attggcgatc ctgctcaatt accagccccc cgcacattgc  17400
tgactaaagg cacactagaa ccagaatatt ttaattcagt gtgcagactt atgaaaacaa  17460
taggtccaga catgttcctt ggaacttgtc gccgttgtcc tgctgaaatt gttgacactg  17520
tgagtgcttt agtttatgac aataagctaa aagcacacaa ggataagtca gctcaatgct  17580
tcaaaatgtt ctacaaaggt gttattacac atgatgtttc atctgcaatc aacagacctc  17640
aaataggcgt tgtaagagaa tttcttacac gcaatcctgc ttggagaaaa gctgttttta  17700
tctcacctta taattcacag aacgctgtag cttcaaaaat cttaggattg cctacgcaga  17760
ctgttgattc atcacagggt tctgaatatg actatgtcat attcacacaa actactgaaa  17820
cagcacactc ttgtaatgtc aaccgcttca atgtggctat cacaagggca aaaattggca  17880
ttttgtgcat aatgtctgat agagatcttt atgacaaact gcaatttaca agtctagaaa  17940
taccacgtcg caatgtggct acattacaag cagaaaatgt aactggactt tttaaggact  18000
gtagtaagat cattactggt cttcatccta cacaggcacc tacacacctc agcgttgata  18060
taaagttcaa gactgaagga ttatgtgttg acataccagg cataccaaag gacatgacct  18120
accgtagact catctctatg atgggtttca aaatgaatta ccaagtcaat ggttacccta  18180
atatgtttat cacccgcgaa gaagctattc gtcacgttcg tgcgtggatt ggctttgatg  18240
tagagggctg tcatgcaact agagatgctg tgggtactaa cctacctctc cagctaggat  18300
tttctacagg tgttaactta gtagctgtac cgactggtta tgttgacact gaaaataaca  18360
cagaattcac cagagttaat gcaaaacctc caccaggtga ccagtttaaa catcttatac  18420
cactcatgta taaaggcttg ccctggaatg tagtgcgtat taagatagta caaatgctca  18480
gtgatacact gaaaggattg tcagacagag tcgtgttcgt cctttgggcg catggctttg  18540
agcttacatc aatgaagtac tttgtcaaga ttggacctga aagaacgtgt tgtctgtgtg  18600
acaaacgtgc aacttgcttt tctacttcat cagatactta tgcctgctgg aatcattctg  18660
tgggttttga ctatgtctat aacccattta tgattgatgt tcagcagtgg ggctttacgg  18720
gtaaccttca gagtaaccat gaccaacatt gccaggtaca tggaaatgca catgtggcta  18780
gttgtgatgc tatcatgact agatgtttag cagtccatga gtgctttgtt aagcgcgttg  18840
attggtctgt tgaataccct attataggag atgaactgag ggttaattct gcttgcagaa  18900
```

-continued

```
aagtacaaca catggttgtg aagtctgcat tgcttgctga taagtttcca gttcttcatg  18960
acattggaaa tccaaaggct atcaagtgtg tgcctcaggc tgaagtagaa tggaagttct  19020
acgatgctca gccatgtagt gacaaagctt acaaaataga ggagctcttc tattcttatg  19080
ctacacatca cgataaattc actgatggtg tttgtttgtt ttggaattgt aacgttgatc  19140
gttacccagc caatgcaatt gtgtgtaggt ttgacacaag agtcttgtca aacttgaact  19200
taccaggctg tgatggtggt agtttgtatg tgaataagca tgcattccac actccagctt  19260
tcgataaaag tgcatttact aatttaaagc aattgccttt cttttactat tctgatagtc  19320
cttgtgagtc tcatggcaaa caagtagtgt cggatattga ttatgttcca ctcaaatctg  19380
ctacgtgtat tacacgatgc aatttaggtg gtgctgtttg cagacaccat gcaaatgagt  19440
accgacagta cttggatgca tataatatga tgatttctgc tggatttagc ctatggattt  19500
acaaacaatt tgatacttat aacctgtgga atacatttac caggttacag agtttagaaa  19560
atgtggctta taatgttgtt aataaaggac actttgatgg acacgccggc gaagcacctg  19620
tttccatcat taataatgct gtttacacaa aggtagatgg tattgatgtg gagatctttg  19680
aaaataagac aacacttcct gttaatgttg catttgagct ttgggctaag cgtaacatta  19740
aaccagtgcc agagattaag atactcaata atttgggtgt tgatatcgct gctaatactg  19800
taatctggga ctacaaaaga gaagccccag cacatgtatc tacaataggt gtctgcacaa  19860
tgactgacat tgccaagaaa cctactgaga gtgcttgttc ttcacttact gtcttgtttg  19920
atggtagagt ggaaggacag gtagaccttt ttagaaacgc ccgtaatggt gttttaataa  19980
cagaaggttc agtcaaaggt ctaacacctt caaagggacc agcacaagct agcgtcaatg  20040
gagtcacatt aattggagaa tcagtaaaaa cacagtttaa ctactttaag aaagtagacg  20100
gcattattca acagttgcct gaaacctact ttactcagag cagagactta gaggatttta  20160
agcccagatc acaaatggaa actgactttc tcgagctcgc tatggatgaa ttcatacagc  20220
gatataagct cgagggctat gccttcgaac acatcgttta tggagatttc agtcatggac  20280
aacttggcgg tcttcattta atgataggct tagccaagcg ctcacaagat tcaccactta  20340
aattagagga ttttatccct atggacagca cagtgaaaaa ttacttcata acagatgcgc  20400
aaacaggttc atcaaaatgt gtgtgttctg tgattgatct tttacttgat gactttgtcg  20460
agataataaa gtcacaagat ttgtcagtga tttcaaaagt ggtcaaggtt acaattgact  20520
atgctgaaat ttcattcatg ctttggtgta aggatggaca tgttgaaacc ttctacccaa  20580
aactacaagc aagtcaagcg tggcaaccag gtgttgcgat gcctaacttg tacaagatgc  20640
aaagaatgct tcttgaaaag tgtgaccttc agaattatgg tgaaaatgct gttataccaa  20700
aaggaataat gatgaatgtc gcaaagtata ctcaactgtg tcaatactta aatacactta  20760
ctttagctgt accctacaac atgagagtta ttcactttgg tgctggctct gataaaggag  20820
ttgcaccagg tacagctgtg ctcagacaat ggttgccaac tggcacacta cttgtcgatt  20880
cagatcttaa tgacttcgtc tccgacgcag attctacttt aattggagac tgtgcaacag  20940
tacatacggc taataaatgg gaccttatta ttagcgatat gtatgaccct aggaccaaac  21000
atgtgacaaa agagaatgac tctaaagaag ggtttttcac ttatctgtgt ggatttataa  21060
agcaaaaact agccctgggt ggttctatag ctgtaaagat aacagagcat tcttggaatg  21120
ctgaccttta caagcttatg ggccatttct catggtggac agcttttgtt acaaatgtaa  21180
atgcatcatc atcggaagca tttttaattg ggctaacta tcttggcaag ccgaaggaac  21240
```

-continued aaattgatgg ctataccatg catgctaact acattttctg gaggaacaca aatcctatcc 21300
agttgtcttc ctattcactc tttgacatga gcaaatttcc tcttaaatta agaggaactg 21360
ctgtaatgtc tcttaaggag aatcaaatca atgatatgat ttattctctt ctggaaaaag 21420
gtaggcttat cattagagaa aacaacagag ttgtggtttc aagtgatatt cttgttaaca 21480
actaaacgaa catgtttatt ttcttattat ttcttactct cactagtggt agtgaccttg 21540
accggtgcac cacttttgat gatgttcaag ctcctaatta cactcaacat acttcatcta 21600
tgaggggggt ttactatcct gatgaaattt ttagatcaga cactctttat ttaactcagg 21660
atttatttct tccattttat tctaatgtta cagggtttca tactattaat catacgtttg 21720
gcaaccctgt catacctttt aaggatggta tttattttgc tgccacagag aaatcaaatg 21780
ttgtccgtgg ttgggttttt ggttctacca tgaacaacaa gtcacagtcg gtgattatta 21840
ttaacaattc tactaatgtt gttatacgag catgtaactt tgaattgtgt gacaaccctt 21900
tctttgctgt ttctaaaccc atgggtacac agacacatac tatgatattc gataatgcat 21960
ttaattgcac tttcgagtac atatctgatg ccttttcgct tgatgtttca gaaaagtcag 22020
gtaattttaa acacttacga gagtttgtgt ttaaaaataa agatgggttt ctctatgttt 22080
ataagggcta tcaacctata gatgtagttc gtgatctacc ttctggtttt aacactttga 22140
aacctatttt taagttgcct cttggtatta acattacaaa ttttagagcc attcttacag 22200
ccttttcacc tgctcaagac atttggggca cgtcagctgc agcctatttt gttggctatt 22260
taaagccaac tacatttatg ctcaagtatg atgaaaatgg tacaatcaca gatgctgttg 22320
attgttctca aaatccactt gctgaactca aatgctctgt taagagcttt gagattgaca 22380
aaggaattta ccagacctct aatttcaggg ttgttccctc aggagatgtt gtgagattcc 22440
ctaatattac aaacttgtgt ccttttggag aggtttttaa tgctactaaa ttcccttctg 22500
tctatgcatg ggagagaaaa aaaatttcta attgtgttgc tgattactct gtgctctaca 22560
actcaacatt tttttcaacc tttaagtgct atggcgtttc tgccactaag ttgaatgatc 22620
tttgcttctc caatgtctat gcagattctt ttgtagtcaa gggagatgat gtaagacaaa 22680
tagcgccagg acaaactggt gttattgctg attataatta taaattgcca gatgatttca 22740
tgggttgtgt ccttgcttgg aatactagga acattgatgc tacttcaact ggtaattata 22800
attataaata taggtatctt agacatggca agcttaggcc ctttgagaga gacatatcta 22860
atgtgccttt ctcccctgat ggcaaacctt gcaccccacc tgctcttaat tgttattggc 22920
cattaaatga ttatggtttt tacaccacta ctggcattgg ctaccaacct tacagagttg 22980
tagtactttc ttttgaactt ttaaatgcac cggccacggt ttgtggacca aaattatcca 23040
ctgaccttat taagaaccag tgtgtcaatt ttaattttaa tggactcact ggtactggtg 23100
tgttaactcc ttcttcaaag agatttcaac catttcaaca atttggccgt gatgtttctg 23160
atttcactga ttccgttcga gatcctaaaa catctgaaat attagacatt tcaccttgct 23220
cttttggggg tgtaagtgta attacacctg gaacaaatgc ttcatctgaa gttgctgttc 23280
tatatcaaga tgttaactgc actgatgttt ctacagcaat tcatgcagat caactcacac 23340
cagcttggcg catatattct actggaaaca atgtattcca gactcaagca ggctgtctta 23400
taggagctga gcatgtcgac acttcttatg agtgcgacat tcctattgga gctggcattt 23460
gtgctagtta ccatacagtt tctttattac gtagtactag ccaaaaatct attgtggctt 23520
atactatgtc tttaggtgct gatagttcaa ttgcttactc taataacacc attgctatac 23580
ctactaactt ttcaattagc attactacag aagtaatgcc tgtttctatg gctaaaacct 23640

```
ccgtagattg taatatgtac atctgcggag attctactga atgtgctaat ttgcttctcc  23700
aatatggtag cttttgcaca caactaaatc gtgcactctc aggtattgct gctgaacagg  23760
atcgcaacac acgtgaagtg ttcgctcaag tcaaacaaat gtacaaaacc ccaactttga  23820
aatattttgg tggttttaat tttcacaaa tattacctga ccctctaaag ccaactaaga  23880
ggtcttttat tgaggacttg ctctttaata aggtgacact cgctgatgct ggcttcatga  23940
agcaatatgg cgaatgccta ggtgatatta atgctagaga tctcatttgt gcgcagaagt  24000
tcaatggact tacagtgttg ccacctctgc tcactgatga tatgattgct gcctacactg  24060
ctgctctagt tagtggtact gccactgctg gatggacatt tggtgctggc gctgctcttc  24120
aaataccttt tgctatgcaa atggcatata ggttcaatgg cattggagtt acccaaaatg  24180
ttctctatga gaaccaaaaa caaatcgcca accaatttaa caaggcgatt agtcaaattc  24240
aagaatcact tacaacaaca tcaactgcat tgggcaagct gcaagacgtt gttaaccaga  24300
atgctcaagc attaaacaca cttgttaaac aacttagctc taattttggt gcaatttcaa  24360
gtgtgctaaa tgatatcctt tcgcgacttg ataaagtcga ggcggaggta caaattgaca  24420
ggttaattac aggcagactt caaagccttc aaacctatgt aacacaacaa ctaatcaggg  24480
ctgctgaaat cagggcttct gctaatcttg ctgctactaa aatgtctgag tgtgttcttg  24540
gacaatcaaa aagagttgac ttttgtggaa agggctacca ccttatgtcc ttcccacaag  24600
cagccccgca tggtgttgtc ttcctacatg tcacgtatgt gccatcccag gagaggaact  24660
tcaccacagc gccagcaatt tgtcatgaag gcaaagcata cttccctcgt gaaggtgttt  24720
ttgtgtttaa tggcacttct tggtttatta cacagaggaa cttcttttct ccacaaataa  24780
ttactacaga caatacattt gtctcaggaa attgtgatgt cgttattggc atcattaaca  24840
acacagttta tgatcctctg caacctgagc tcgactcatt caaagaagag ctggacaagt  24900
acttcaaaaa tcatacatca ccagatgttg atcttggcga catttcaggc attaacgctt  24960
ctgtcgtcaa cattcaaaaa gaaattgacc gcctcaatga ggtcgctaaa aatttaaatg  25020
aatcactcat tgaccttcaa gaattgggaa aatatgagca atatattaaa tggccttggt  25080
atgtttggct cggcttcatt gctggactaa ttgccatcgt catggttaca atcttgcttt  25140
gttgcatgac tagttgttgc agttgcctca agggtgcatg ctcttgtggt tcttgctgca  25200
agtttgatga ggatgactct gagccagttc tcaagggtgt caaattacat tacacataaa  25260
cgaacttatg gatttgttta tgagattttt tactcttgga tcaattactg cacagccagt  25320
aaaaattgac aatgcttctc ctgcaagtac tgttcatgct acagcaacga taccgctaca  25380
agcctcactc cctttcggat ggcttgttat tggcgttgca tttcttgctg tttttcagag  25440
cgctaccaaa ataattgcgc tcaataaaag atggcagcta gccctttata agggcttcca  25500
gttcatttgc aatttactgc tgctatttgt taccatctat tcacatcttt tgcttgtcgc  25560
tgcaggtatg gaggcgcaat ttttgtacct ctatgccttg atatattttc tacaatgcat  25620
caacgcatgt agaattatta tgagatgttg gctttgttgg aagtgcaaat ccaagaaccc  25680
attactttat gatgccaact actttgtttg ctggcacaca cataactatg actactgtat  25740
accatataac agtgtcacag atacaattgt cgttactgaa ggtgacggca tttcaacacc  25800
aaaactcaaa gaagactacc aaattggtgg ttattctgag gataggcact caggtgttaa  25860
agactatgtc gttgtacatg gctatttcac cgaagtttac taccagcttg agtctacaca  25920
aattactaca gacactggta ttgaaaatgc tacattcttc atctttaaca agcttgttaa  25980
```

agacccaccg aatgtgcaaa tacacacaat cgacggctct tcaggagttg ctaatccagc 26040
aatggatcca atttatgatg agccgacgac gactactagc gtgcctttgt aagcacaaga 26100
aagtgagtac gaacttatgt actcattcgt ttcggaagaa acaggtacgt taatagttaa 26160
tagcgtactt ctttttcttg ctttcgtggt attcttgcta gtcacactag ccatccttac 26220
tgcgcttcga ttgtgtgcgt actgctgcaa tattgttaac gtgagtttag taaaaccaac 26280
ggtttacgtc tactcgcgtg ttaaaaatct gaactcttct gaaggagttc ctgatcttct 26340
ggtctaaacg aactaactat tattattatt ctgtttggaa ctttaacatt gcttatcatg 26400
gcagacaacg gtactattac cgttgaggag cttaaacaac tcctggaaca atggaaccta 26460
gtaataggtt tcctattcct agcctggatt atgttactac aatttgccta ttctaatcgg 26520
aacaggtttt tgtacataat aaagcttgtt ttcctctggc tcttgtggcc agtaacactt 26580
gcttgttttg tgcttgctgc tgtctacaga attaattggg tgactggcgg gattgcgatt 26640
gcaatggctt gtattgtagg cttgatgtgg cttagctact tcgttgcttc cttcaggctg 26700
tttgctcgta cccgctcaat gtggtcattc aacccagaaa caaacattct tctcaatgtg 26760
cctctccggg ggacaattgt gaccagaccg ctcatggaaa gtgaacttgt cattggtgct 26820
gtgatcattc gtggtcactt gcgaatggcc ggacaccccc tagggcgctg tgacattaag 26880
gacctgccaa aagagatcac tgtggctaca tcacgaacgc tttcttatta caaattagga 26940
gcgtcgcagc gtgtaggcac tgattcaggt tttgctgcat acaaccgcta ccgtattgga 27000
aactataaat taaatacaga ccacgccggt agcaacgaca atattgcttt gctagtacag 27060
taagtgacaa cagatgtttc atcttgttga cttccaggtt acaatagcag agatattgat 27120
tatcattatg aggactttca ggattgctat ttggaatctt gacgttataa taagttcaat 27180
agtgagacaa ttatttaagc ctctaactaa gaagaattat tcggagttag atgatgaaga 27240
acctatggag ttagattatc cataaaacga acatgaaaat tattctcttc ctgacattga 27300
ttgtatttac atcttgcgag ctatatcact atcaggagtg tgttagaggt acgactgtac 27360
tactaaaaga accttgccca tcaggaacat acgagggcaa ttcaccattt caccctcttg 27420
ctgacaataa atttgcacta acttgcacta gcacacactt tgcttttgct tgtgctgacg 27480
gtactcgaca tacctatcag ctgcgtgcaa gatcagtttc accaaaactt ttcatcagac 27540
aagaggaggt tcaacaagag ctctactcgc cactttttct cattgttgct gctctagtat 27600
ttttaatact ttgcttcacc attaagagaa agacagaatg aatgagctca ctttaattga 27660
cttctatttg tgctttttag cctttctgct attccttgtt ttaataatgc ttattatatt 27720
ttggttttca ctcgaaatcc aggatctaga agaaccttgt accaaagtct aaacgaacat 27780
gaaacttctc attgttttga cttgtatttc tctatgcagt tgcatatgca ctgtagtaca 27840
gcgctgtgca tctaataaac ctcatgtgct tgaagatcct tgtaaggtac aacactaggg 27900
gtaatactta tagcactgct tggctttgtg ctctaggaaa ggttttacct tttcatagat 27960
ggcacactat ggttcaaaca tgcacaccta atgttactat caactgtcaa gatccagctg 28020
gtggtgcgct tatagctagg tgttggtacc ttcatgaagg tcaccaaact gctgcattta 28080
gagacgtact tgttgtttta aataaacgaa caaattaaaa tgtctgataa tggaccccaa 28140
tcaaaccaac gtagtgcccc ccgcattaca tttggtggac ccacagattc aactgacaat 28200
aaccagaatg gaggacgcaa tggggcaagg ccaaaacagc gccgaccccaa aggtttaccc 28260 aataatactg cgtcttggtt cacagctctc actcagcatg gcaaggagga acttagattc 28320
cctcgaggcc agggcgttcc aatcaacacc aatagtggtc cagatgacca aattggctac 28380
taccgaagag ctacccgacg agttcgtggt ggtgacggca aaatgaaaga gctcagcccc 28440
agatggtact tctattacct aggaactggc ccagaagctt cacttcccta cggcgctaac 28500
aaagaaggca tcgtatgggt tgcaactgag ggagccttga atacacccaa agaccacatt 28560
ggcacccgca atcctaataa caatgctgcc accgtgctac aacttcctca aggaacaaca 28620
ttgccaaaag gcttctacgc agagggaagc agaggcggca gtcaagcctc ttctcgctcc 28680
tcatcacgta gtcgcggtaa ttcaagaaat tcaactcctg gcagcagtag gggaaattct 28740
cctgctcgaa tggctagcgg aggtggtgaa actgccctcg cgctattgct gctagacaga 28800
ttgaaccagc ttgagagcaa agtttctggt aaaggccaac aacaacaagg ccaaactgtc 28860
actaagaaat ctgctgctga ggcatctaaa aagcctcgcc aaaaacgtac tgccacaaaa 28920
cagtacaacg tcactcaagc atttgggaga cgtggtccag aacaaaccca aggaaatttc 28980
ggggaccaag acctaatcag acaaggaact gattacaaac attggccgca aattgcacaa 29040
tttgctccaa gtgcctctgc attctttgga atgtcacgca ttggcatgga agtcacacct 29100
tcgggaacat ggctgactta tcatggagcc attaaattgg atgacaaaga tccacaattc 29160
aaagacaacg tcatactgct gaacaagcac attgacgcat acaaaacatt cccaccaaca 29220
gagcctaaaa aggacaaaaa gaaaaagact gatgaagctc agcctttgcc gcagagacaa 29280
aagaagcagc ccactgtgac tcttcttcct gcggctgaca tggatgattt ctccagacaa 29340
cttcaaaatt ccatgagtgg agcttctgct gattcaactc aggcataaac actcatgatg 29400
accacacaag gcagatgggc tatgtaaacg ttttcgcaat tccgtttacg atacatagtc 29460
tactcttgtg cagaatgaat tctcgtaact aaacagcaca agtaggttta gttaacttta 29520
atctcacata gcaatcttta atcaatgtgt aacattaggg aggacttgaa agagccacca 29580
cattttcatc gaggccacgc ggagtacgat cgagggtaca gtgaataatg ctagggagag 29640
ctgcctatat ggaagagccc taatgtgtaa aattaatttt agtagtgcta tccccatgtg 29700
attttaatag cttcttagga gaatgac 29727

<210> SEQ ID NO 7
<211> LENGTH: 29732
<212> TYPE: DNA
<213> ORGANISM: Bat SARS-like coronavirus
<300> PUBLICATION INFORMATION:
<308> DATABASE ACCESSION NUMBER: GENBANK / MG772934
<309> DATABASE ENTRY DATE: 2020-09-29
<313> RELEVANT RESIDUES IN SEQ ID NO: (1)..(29732)

<400> SEQUENCE: 7
atattaggtt tttaccttcc caggtaacaa accaactaac tctcgatctc ttgtagatct 60
gttctctaaa cgaactttaa aatctgtgtg actgtcactt agctgcatgc ttagtgcact 120
cacgcagttt aattataatt aattactgtc gttgacagga cacgagtaac tcgtctatct 180
tctgcaggtt gcttacggtt tcgtccgtgt tgcagccgat catcagcata ccttggtttc 240
gtccgggtgt gaccgagagg taagatggag agccttgtcc ctggtttcaa cgagaaaaca 300
cacgtccaac tcagtttgcc tgttttacag gtttgtgacg tgcttgtacg tggctttgga 360
gactccgtag aggaggcttt atcagaggca cgtcaacatc ttaaagatgg cacttgtggc 420
ttagtagaag ttgaaaaagg tgttttacct caacttgaac agccctatgt gttcatcaaa 480
cgttctgatg cccgaactgc acatcatggc catgttatgg tcgaattagt agcagaactc 540
gatggcattc agtacggtcg tagtggtgag acacttggtg ttcttgtccc tcatgtggga 600

-continued

```
gaggtaccag ttgcttaccg taaagttctt cttcgtaaga acggtaataa aggagctggt    660
ggccatagtt acggcgccga tctaaagtct tttgacttag gcgacgagct tggtactgat    720
cctattgaag attttcaaga aaattggaac actaaacatg gcagtggtgt tacccgtgaa    780
ctcaagcgtg agcttaacgg gggtgcatac actcgctatg tagacaacaa cttttgtggc    840
ccagatggct accctcttga gtgcattaaa aactttttag ctcgtgctgg taaggcttca    900
tgcactttat ctgaacaact ggattttatt gacactaaaa gaggtgtata ctgctgccgt    960
gaacatgagc atgaaattgc ttggtacacg gaacgctccg aaaagagcta tgaatcgcag   1020
acaccttttg aaattaagtt ggcaaagaaa tttgacacct tcaatggaga atgtccaaat   1080
tttgtatttc ctctaaattc aacaatcaag accattcaac caagggttga aaagaaaaag   1140
cttgatggtt tcatgggtag aattcgatct gtctatcctg ttgcttcacc aaatgaatgc   1200
aaccaaatgt gcctctcaac tctcatgaag tgtgaccatt gtggtgaaac ttcatggcag   1260
acgggtgatt ttgttagagc cacttgcgaa ttctgtggta ctgaaaattt gactaaagaa   1320
ggcgccacaa cttgtggtta cttacctcaa aatgctgttg taaaaattta ttgtccagca   1380
tgtcataatc cagaagtggg acctgagcat agtcttgctg aatatcataa cgagtctggt   1440
ttgaaaaccg ttcttcgtaa gggtggtcgt accattgctt atgggggctg tgtgtttgct   1500
tatgttggtt gctacaacaa gtgtgcctat tgggttccac gtgctagtgc taacataggc   1560
tgtaatcaca caggtgttgt tggagaaggt tctgaaagtc taaacgacaa ccttcttgaa   1620
atattgcaaa aggagaaagt caacatcaat attgttggtg acttcaaact taatgaagag   1680
attgccatta ttttggcatc tttttctgct tctacaagtg cttttgtaga aactgtaaaa   1740
ggtttggatt acaaaacatt caaacaaatt gttgaatcct gtggtaactt taaagttact   1800
aaaggaaagg ctaagaaggg tgcctggaac attggggaac agaaatcaat actgagtcct   1860
ctttatgcat ttgcatcaga ggctgctcgt gttgtgcgct ccattttttc tcgtactctt   1920
gaaactgctc aatactctgt gcgtgtctta caacaggccg ccataacaat cttagatgga   1980
atttcacagt attccctgag actcattgat gctatgatgt tcacatctga cttggttact   2040
aacaatctag ttgtaatggc ttacattacg ggtggtgttg tacaaatgac ttcacagtgg   2100
ctaacaaata tctttggcac tgtttatgaa aaacttaaac cggttcttga ttggctcgaa   2160
gagaaattca aggaaggtgt agagtttctt agagacggtt gggaaattgt taaatttatc   2220
tctacttgtg cttgtgaaat tgtcggtgga caaattgtca cccgtgcaaa ggaagttaag   2280
gagagtgttc agacattctt taagcttgta aataaatttt tggctttgtg tgctgactcc   2340
atcattattg gtggagctaa acttaaagcc ttgaatttag gtgaaacatt tgtcacacac   2400
tcaaagggat tgtacagaaa gtgtgttaga tccagagaag aaactggctt actcttgcct   2460
ctgaaagccc caaaagaaat tattttctta gagggagaaa cacttcccac agaagtgtta   2520
acagaggaag ttgtcttgaa aactggtgtt ttacaaccat tagaacaacc tactaatgag   2580
gctgttgaag ccccattgat tggtacacca gtctgtatta acgggctcat gttgctcgaa   2640
attaaagaca cagaaaagta ctgtgccctt gcacctaata tgatggtaac aaataatacc   2700
tttacactta aaggcggtgc accaacaaaa gtcacttttg gtgatgacac tgtgattgaa   2760
gtgcagggtt acaagagtgt aaacatcact tttgaacttg atgaaaggat tgataaagta   2820
cttaatgaga agtgctctag ttatacagtt gaactcggta cagatgtaaa cgagttcgct   2880
tgtgttgttg ctgatgctgt cataaaaact ttacaaccag tatctgaact actcacacca   2940
ctgggcattg atttagacga gtggagtatg gctacatact acttgtttga tgagtccggt   3000
```

gaatttaaat tgtcttcaca tatgtactgt tctttttacc ctcctgaaga tgaaggggaa 3060
gatgattgtg aagaaggaca gtttgaacca tcaactcaat atgagtatgg tactgaggat 3120
gactaccaag gtaaaccttt ggagtttggt gctacttctt tttcttcttc ttcacaggaa 3180
gaagaacaag aagaggattg gttagaatct gatagtcagg acggccaaga gactgctgtt 3240
actaaaacta gtgaacaaaa taatttcaca ggttatttaa aattaactga caatgttttc 3300
attaaaaatg ctgacattgt agaagaagct aaaaaggtaa agcctacagt agttgttaat 3360
gcagctaata tttaccttaa acatggagga ggtgttgctg gagctttaaa taaagcaact 3420
aacaacgcca tgcagttgaa tctgattagt aacataacta ccaatgggcc actaattgtg 3480
ggtggtagtt gtgttttgag tggacataac cttgctaaaa attgtcttca tgttgttggc 3540
cctaatgtca atagaggtga agacattcaa ttgcttaaaa atgcttatga aaatttcaat 3600
caacatgaga ttttactcgc accattatta tcggctggta tttttggtgt tgatcctgta 3660
cattctttaa gagtttgtgt agaaactgtt cacacaaatg tctatctagt tgtctttgac 3720
aaaaatcttt atgacaaact tgtttcaagc tttttagaga tgaagagtgg aaaacaagta 3780
gaacaaaaag ttgctgaaaa tcctaaagag gaagttaagc catttttac tgaaaataaa 3840 ccttcagttg aacaaagaca acaagctgaa gagaagaaaa tcaaagctag tattgaagaa 3900
gttacaacta ctctagagga gaccaagttc cttacagaaa acttgttact ttatattgac 3960
atcaatggca atcttcaccc agattctgcc actcttgtta aagatattga catcactttc 4020
ttgaagaaag atgttcccta tatagtgggt gatgttatta aagaaggtgc tttaactgct 4080
gtagttatac ctactaaaaa ggctggtggc actactgaaa tgcttgctaa agctttaaga 4140
aaagtgccaa cagataatca cataaccacc taccctggtc agggtttaaa tggttacact 4200
gtagaagaag caaagacagt gcttaaaaag tgtaaaagtg ttttttacat tttaccatct 4260
attctcccta atgagaagca agaaattcta ggaactgttt cttggaactt gcgagagatg 4320
ctcgcacatg cagaagaaac acgtaagtta atgcctgttt gtatggagac taaagctata 4380
gtttcaacta tacaacgtaa gtacaaaggc attaaaatac aggagggtgt ggttgactat 4440
ggtgctagat tttactttta tactagtaaa actactgtag catcacttat taacacactt 4500
aacaatctaa atgagactct tgtcacaatg ccattaggat atgtgacgca cggtctaaat 4560
ttagaagaag ctgcgcggta catgaggtct ctcaaagtac cggctacagt ctctgtttct 4620
tcaccagatg ctgttacagc atataatggt tatcttactt cttcttcaaa aacacctgaa 4680
gaacacttta tcgaaaccgt ctcacttgct ggttcctata aagattggtc ttattctgga 4740
cagtctacag aactaggtat agaatttctt aagagaggtg ataagagtgt atattacacc 4800
agtaatccta tcacattcta tctagatggt gaagttatca cctttgataa tcttaagaca 4860
attctctctt tgagggaagt gaggtctatt aaagtgttta caacagtaga taacattaat 4920
ctccacactc aaattgtgga tatgtctatg acatatgggc aacagttcgg cccaacttat 4980
ttggatggag ctgatgttac taaaataaaa cctcataatt cacatgaagg taaaacattt 5040
tatgttttgc ctaatgatga cactttacgt gtggaggctt ttgagtacta ccatacaact 5100
gactctagtt ttcttggtag gtacatgtca gcattaaacc acactaaaaa gtggaaatac 5160
ccacaagtaa atggtttaac ttctataaga tgggcagaca acaattgtta tcttgctact 5220
gcattattaa cacttcaaca aatagagttg aaatttaatc caccagcttt acaagatgcc 5280
tattataggg caagagctgg tgaggctgct aatttttgtg cacttatcct agcctattgt 5340

-continued aataagacag taggtgagtt aggtgatgtc agagaaacaa tgaattattt gtttcaacat 5400
gccaatttag attcttgtaa aagagtcttg aatgtggtgt gtaaaacttg tggacaacag 5460
caaacaactc ttaagggtgt agaagctgtt atgtatatgg gcacactttc ttatgaacaa 5520
cttaagaagg gtgtgcagat accttgtatg tgtggtaaac aagctacaca atatctagta 5580
caacaagagt cacctttgt tatgatgtct gcaccacccg cccaatatga acttaagcat 5640
ggtacatttg tttgtgctag tgagtatact ggtaattacc agtgtggtca ctacaaacat 5700
ataacttcta aagaaacctt gtattgtata gatggtgctt tactcacaaa gtcctctgag 5760
tacaaaggtt ctattacaga tgttttctat aaggaaaaca gttatacaac aaccataaaa 5820
ccagttacat acaagttgga tggtgttgtt tgtacagaaa ttgatcctaa gttggatggt 5880
tattataaga aagacaattc ttatttcaca gagcaaccaa ttgatcttgt accaaaccaa 5940
ccttacccga atgcaagctt tgacaatttt aggtttgtat gtgataatat caaatttgcc 6000
gatgatttaa atcaattgtc tggttataag aaacctgctt tgagagagct taaggttaca 6060
ttctttcctg acttaaatgg tgatgtagtg gctattgatt ataagcacta cacaccttct 6120
tttaagaaag gagctaaatt gttgcataag ccaattgttt ggcatgttaa caatgcaact 6180
aacaaagcaa cgtataaacc aaatatttgg tgcatacgtt gtctttggag tacaaaaccg 6240
gttgaaacat caaattcttt tgatgcactg aaattagggg acacacaggg aatggataat 6300
cttgcctgtg aagttctaaa accagtctct gaagaagtag tggaaaatcc taccatacag 6360
aaagacattc ttgagtgtaa tgtgaaaact accgaagttg taggagacat tatacttaaa 6420
ccggcaattg atggtctaaa aattacagaa gaggttggtc atacagacct aatggctgct 6480
tatgttgaca attcaagtct tactattaag aaacctagtg aattatccag agtattaggt 6540
ttgaaaactt tagccactca tggcttggct gctattaata gtgttccttg ggacactata 6600
gctaattatg ctaagccttt ccttaataag gttgttagca caactactaa catagtcaca 6660
cggtgtctaa accgtgtttg tactaattat atgccttatt tgtttacttt attgctacaa 6720
ttgtgtactt ttactaaaag tacaacttct agaataagag catctatgcc aaccactata 6780
gcaaagaata ctgttaaaag tgttggtaaa ttttgtatag aggcttcatt taattatttg 6840
aagtcaccta atttttctaa attgataaat attgtaattt ggtttttatt attaagtgtt 6900
tgcctaggtt ctttaatcta ttcaactgct gctttaggtg tcttaatgtc taatttaggc 6960
atgccttctt attgtactgt ttacagagaa ggttacttga actctactaa cgtcactatt 7020
gcaacctact gcactggttc tataccttgt agtgtttgtc ttagtggttt agattctttg 7080
gatacttacc catccttaga aactatacaa attaccattt cgtcttttaa atgggattta 7140
actgcttttg gtctagttgc agagtggttt ttggcatata ttcttttac taggttcttt 7200 tatgtacttg gattggctgc aatcatgcaa ttgtttttca gctattttgc agtacatttt 7260
attagtaatt cttggcttat gtggttaata attaatcttg tacaaatggc cccaatttca 7320
gctatggtta gaatgtatat tttctttgca tcattttatt atgtatggaa aagttatgtg 7380
catgttgtag atggttgtac ttcatcaact tgtatgatgt gttataaacg taatagagca 7440
acaagagttg aatgtacaac tattgttaat ggtgttagaa ggtcctttta tgtctatgct 7500
aatggaggta aaggcttttg caaactacac aactggaatt gtatcaattg tgatacattc 7560
tgtgctggta gtacatttat tagtgacgaa gttgctagag acttatcact acagtttaaa 7620
agaccaataa atcctactga ccagtcttcc tatattgttg atagtgttac agtgaagaat 7680
ggttccatcc acctttactt tgataaggct ggtcaaaaga cttatgaaag acattctctc 7740

-continued

```
tctcattttg ttaacttaga caatctgaga gctaataaca ctaagggttc attgcctatt    7800
aatgttatag tttttgatgg taaatcaaaa tgtgaagaat catctgctaa atcagcgtct    7860
gtttattata gtcagcttat gtgccaacct atactgttac tggaccaggc attagtgtct    7920
gatgttggtg acagtgcaga agttgcagtt aagatgtttg atgcttatgt taatatattt    7980
tcatcaactt tcaatgttcc aatggaaaaa ctcaaagcat tagttgcgac tgcagaagct    8040
gaacttgcaa agaatgtgtc tttagacaac gtcttatcta cttttatttc agcagctcgc    8100
caagggtttg ttgattcaga tgtagaaacc aaagatgttg ttgaatgtct taaattgtca    8160
caccaatctg acatagaagt tacaggtgac agttgtaaca attacatgct cacttataac    8220
aaagttgaaa acatgacacc tcgggacctc ggtgcttgta ttgattgtag tgcacgtcat    8280
attaatgcac atgtggcaaa gagtcataac atagctttga tttggaatgt taaagatttc    8340
atgtcattgt ctgaacaact acgaaaacaa atacgcagtg ctgctaagaa gaataacttg    8400
ccttttagat tgacatgtgc aaccactaga caagttgtta atgttgttac aacaaaaata    8460
gcacttaggg gtggtaaaat tgttaacaac tggttgaagc agttgattaa ggttacactt    8520
gtgtttcttt tcatcactgt tatcttctat ttaataacac ctgctcatgt catgtttaag    8580
cacaatgact tttcaagtga aattatagga tacaaggcta ttgatggtgg tgtcactcgt    8640
gacatagcgc caacagatac ttgttttgct aacaaacatg ctgactttga ctcttggttt    8700
agtcagcgtg gtggtagcta tactaatgat aaagcttgcc cattgatagc agctgttatc    8760
acaagagaag ttggctttgt tgtgcccggt ttacctggca caatattacg cacaattaat    8820
ggtgacttct tacatttcct tcctagagtg tttagtgcgg taggtaacat ttgttacact    8880
ccttctaaac ttatagagta cactgacttt gcaacatcgg catgtgtttt agctgctgaa    8940
tgtaccatct ttaaagattc ttctggtaaa ccagtgcctt attgttatga cactaatgta    9000
ctagaaggtt ctgttgcgta tgaaagtctc cgccctgaca tacgctatgt gctcatggac    9060
ggttctataa ttcaattccc taacacctac cttgaaggtt ctgttagagt agtaacaact    9120
tttgattcag agtattgtag acatggtact tgcgaaagat cagaggctgg catttgtgta    9180
tctactagtg gtagatgggt acttaataat gattattaca gatccttgcc aggagttttt    9240
tgtggtgtag atgctgtgaa tttacttact aatatgttca cgccattaat tcaacctatt    9300
ggtgctttgg acatatctgc atctattgta gcaggtggtg ttgtagctat tatagtaact    9360
tgtctagcct actacttcat gaggtttaga agagcttttg gtgaatacag tcatgtagtt    9420
gcctttaaca ctctactatt ctttatgtca ttcactgtac tctgtttaac accagtctat    9480
tcattcttac ctggtgttta ttctgttatt tacttgtact tgacatttta tcttactaat    9540
gatgtttctt tcttagcaca tatccaatgg atggttatgt tcacaccctt agtgcctttc    9600
tggatgacaa ttgtttatgt catttgcatt tccacaaagc atttttattg gttctttagt    9660
aactacctaa agagacgtgt agtctttaat ggtgtttcct ttagtacatt tgaggaggct    9720
gcattatgta ccttttttgtt aaataaagaa atgtatctga aattgcgtag tgatgtactt    9780
ctacctctta cgcaatataa tagatattta gctctttata ataagtacaa gtattttagt    9840
ggggccatgg acactaccag ttatagagaa gcagcttgct gtcatctggc taaggctcta    9900
aatgatttca gtaattcagg ttctgatgtc ctctaccaac caccacaaac ttcaatcaca    9960
tcagcgattt tgcagagtgg ttttagaaaa atggcattcc catctggtaa agttgaaggt   10020
tgcatggtac aagttacttg tggtaccact acacttaatg gtctttggct tgatgatgta   10080
```

-continued

```
gtttactgtc cacgacatgt gatctgcact tctgaagaca tgctcaatcc taattatgaa  10140
gatttactta tacgtaaatc taaccataat tttttagttc aggctggtaa tgttcaactt  10200
agggttgttg gacattctat gcaaaattgt gttcttaagc ttaaagtaga tacagctaac  10260
cctaagacac ctaagtataa gtttgtgcgc attcaacccg gacagacttt ttcagtatta  10320
gcctgttaca atggttcacc atctggtgtt taccaatgtg ccatgagacc taattttact  10380
attaagggtt cattccttaa tggttcatgt ggtagtgttg gttttaatat agactatgac  10440
tgtgtctctt tttgttatat gcatcatatg gagttaccaa cgggagttca tgctggcaca  10500
gacttagaag gtaccttcta cggacctttt gttgacagac agacagcaca agcggctggt  10560
actgacacaa ctattacagt taatgttcta gcttggttgt atgcagctgt tataaacgga  10620
gatagatggt tccttaacag gtttaccacg actctaaacg attttaatct tgtggctatg  10680
aagtataatt atgaacctct aacacaagac catcttgaca tactaggacc tctttcagct  10740
caaactggaa ttgcagtcct agatatgtgt gcttcattaa aagaattatt acaaaatggt  10800
atgaatggac gtaccatatt gggtagtgct ttattagaag atgaatttac acctttcgat  10860
gttgttagac aatgttcagg tgtcaccttt caaagtgcag tgaaaaggac aatcaagggc  10920
acgcaccatt ggttgttgct tacagttttg acttcactct tagttttagt tcagagtact  10980
caatggtctt tgttcttctt tgtgtatgaa aatgccttta tgccttttgc tatgggtatt  11040
attgctatgt ctgcttttgc tatgatgttt gtcaaacata agcatgcatt cctctgtttg  11100
ttcctattac cttctcttgc tactgtagct tattttaata tggtctacat gcctgctagt  11160
tgggtgatgc gtattatgac atggttggat atagttgata ctagtttgtc tggtttcaag  11220
ctaaaggact gtgttatgta tgcatcagct gtagtgttat taatcctcat gacagcaaga  11280
actgtatatg atgatagtgc tagaagagtt tggacactta tgaatgtcct gacactcgtt  11340
tataaagttt attatggtaa tgctttagac caagctattt ccatgtgggc tcttataatc  11400
tctgttactt ctaactactc aggtgtagtt acaactgtca tgtttttggc cagaggtatt  11460
gtttttatgt gtgttgagta ttgtcctatc ttctttataa ctggcaatac actccagtgt  11520
ataatgctag tttattgttt cttaggttat ttctgtactt gttattttgg tctcttctgt  11580
ttactcaacc gctattttag gcttactctt ggtgtttatg actatttagt ctctacacaa  11640
gaatttaggt atatgaactc tcagggactt ctgcctccta agagtagtat tgatgctttc  11700
aagcttaata ttaaattatt gggtattgga ggtaagccat gcattaaggt tgctactgta  11760
cagtctaaaa tgtctgacgt aaagtgcaca tctgtggtac tgctctctgt acttcaacaa  11820
cttagagtag agtcatcttc taaattgtgg gcacagtgtg tacaactcca caatgatatc  11880
cttcttgcta aagacacaac tgaagctttt gaaaagatgg tttctcttct gtctgttttg  11940
ctatccatgc aaggtgctgt agaccttaac aagttgtgcg aggaaatgct cgacaaccgt  12000
gctactcttc aagctattgc ttcaaaattt agttctttac catcatatgc cgcttatgca  12060
acagcccaag aggcttatga gcaggctgta gttaatggtg attctgaagt tgttcttaaa  12120
aagttaaaga aatctttgaa tgtggctaaa tctgagtttg accgtgatgc tgccatgcaa  12180
cgcaagttgg aaaagatggc ggatcagact atgacccaaa tgtacaagca ggcaagatct  12240
gaagacaaga gggcaaaagt aactagtgca atgcaaacta tgcttttcac tatgcttaga  12300
aaacttgata atgatgcact taacaacatt atcaacaatg cacgtgatgg ttgtgtacca  12360
ctcaacatca taccactcac aacagcagcc aaactcatgg ttgttgtgcc tgactatgga  12420
acctacaaga atacttgtga tggtaacact tttacatatg catcagcact ctgggaaatc  12480
```

cagcaagttg ttgatgcaga tagtaaaatt gtgcagctta gtgaaatcaa catggacaac 12540
tcaccaaatt tggcttggcc tcttattgtc actgctttaa gagctaattc agctgtcaaa 12600
ctacagaaca atgagctgag tccagtagca ctacggcaga tgtcctgtgc ggctggtact 12660
acacagacag cttgtactga tgacaacgca cttgcctact ataacaattc taagggaggt 12720
aggtttgtgc tggcattact atcagaccat caagatctca aatggtctag atttcctaag 12780
agtgatggca caggtactat ttacacagag ctggaaccac cttgtaggtt tgttacagac 12840
acaccaaaag gacctaaagt gaagtacttg tactttatta agggtcttaa caacctaaat 12900
agaggtatgg tactgggtag tttagctgct acagtacgtc ttcaggctgg taatgcgaca 12960
gaagtgcctg ccaactcaac tgtgctttct ttctgtgcct tcgctgttga cccagctaag 13020
gcctacaaag attacttggc aagtggtgga caaccaatca cgaattgtgt gaagatgttg 13080
tgtacacaca ctggtactgg acaggcaatt acggtgacac cagaagccaa tatggaccag 13140
gagtcctttg gtggtgcttc gtgctgtctg tattgtagat gccacattga tcacccaaat 13200
cctaagggat tctgtgattt gaaaggtaag tatgttcaaa tacctaccac ttgtgctaat 13260
gaccctgtgg gttttacact tagaaacaca gtctgtaccg tctgtggaat gtggaaaggt 13320
tatggctgta gttgtgatca actccgcgaa cccatgatgc agtctgcgga cgcgtcaacg 13380
tttttaaacg ggtttgcggt gtaagtgcag cccgtcttac accgtgcggc tcaggcatta 13440
gcactgatgt cgtttacagg gcttttgata tttacaacga gaaagttgct ggttttgcaa 13500
agttcctaaa aactaattgc tgccgcttcc aggaaaagga tgaggaaggc aatttattag 13560
actcttattt cgtagttaag aggcacacaa tgtccaacta ccaacatgaa gagaatattt 13620
ataacttggt caaggagtgt ccagctgttg ctgttcatga ctttttcaag tttagagtag 13680
atggtgacat ggtaccacat atatcacgtc agcgtttaac taagtacaca atggctgatt 13740
tagtctatgc tctacgtcat tttgatgagg gcaattgtga cacattaaaa gaaatacttg 13800
tcacatacaa ttgttgtgat ggtgattatt tcaataagaa ggattggtac gacttcgtag 13860
agaatcctga catcttacgc gtatacgcta acctaggtga gcgtgtacgt caagcattat 13920
taaagactgt acaattctgc gatgctatgc gcgatgcggg cattgtaggt gtactcacac 13980
tagataatca ggatcttaat gggaactggt acgatttcgg tgatttcgta caagtagcgc 14040
caggttgcgg agttcctatt gttgactcgt attattcatt gttgatgccc attcttactc 14100
tgacaagggc attagctgct gagtcccata tggatgctga tcttgcaaaa ccacttatta 14160
agtgggattt gttgaaatat gattttacgg aagagagact ttgtctcttc gaccgttatt 14220
ttaaatattg ggatcagaca taccatccca attgtattaa ctgtttggat gataggtgta 14280
tccttcattg tgcaaacttt aatgtcttat tttctactgt gtttccgcct acaagttttg 14340
gaccactagt tagaaagata tttgtagatg gtgtaccttt tgttgtttca acgggatacc 14400
attttcgtga gctaggggtt gtacataatc aggatgtaaa cctacatagc tcgcgcctca 14460
gttttaagga acttttagtg tacgctgctg atccagctat gcatgctgcc tctggtaatt 14520
tgttgttaga taaacgcact acatgctttt cagtagctgc actaacaaat aatgttgctt 14580
ttcaaactgt caaacccggt aattttaata aagactttta tgactttgct gtgtctaaag 14640
gcttctttaa ggaaggaagt tctgttgaat taaaacactt cttctttgct caggatggca 14700
atgctgctat cagtgattat gactattacc gttataatct gccaacaatg tgtgatatta 14760
cacaactcct attcgtaatt gaggttgtcg ataaatactt tgattgttac gatggtggct 14820

-continued

```
gtatcaatgc caaccaagtt atcgttaaca atctagacaa atcagccggt ttcccattca  14880
acaaatgggg taaggctaga ctttattatg attcaatgag ttatgaggac caagatgcac  14940
tgttcgcata cactaagcgt aacgtcatcc ctacaataac tcaaatgaac cttaagtatg  15000
ccattagtgc aaagaataga gctcgcaccg ttgctggtgt ctctatctgt agtactatga  15060
ccaatagaca gtttcaccag aaattattaa agtcaatagc cgccactaga ggagctactg  15120
tagtaattgg aacaagtaaa ttttatggtg gctggcataa catgttaaaa actgtttaca  15180
gtgatgtaga aagtcctcac cttatgggtt gggactaccc aaaatgtgac agagccatgc  15240
ctaatatgct tagaatcatg gcttccctcg ttcttgctcg caaacatagc acttgttgta  15300
acttgtcaca ccgtttttat agattagcta atgagtgtgc acaagtatta agtgagatgg  15360
tcatgtgtgg cggctcatta tatgtgaaac caagtggaac gtcatccggt gatgccacaa  15420
ctgcttatgc taatagtgtg tttaacatct gtcaagcagt aacagctaat gtgaatgcac  15480
ttctctcaac tgatggtaat aagattgctg ataagtacgt ccgcaacctt caacacagac  15540
tttatgagtg tctctataga aatagagacg tggatcatga attcgtggat gaattttatg  15600
catatttgcg taaacatttc tccatgatga tactctcaga tgacgcagtc gtatgctata  15660
atagtaatta tgcggcacag ggtttagtag ctagcattaa gaactttaaa gcagttcttt  15720
actaccaaaa caatgtgttt atgtctgagg caaaatgctg gactgagact gatcttacta  15780
aaggacctca cgaattttgc tctcagcata cgatgctagt taaacaagga gatgattatg  15840
tgtacctgcc ttatccagat ccatctagaa tattaggcgc aggctgtttt gtcgatgaca  15900
tcgtcaagac agatggtaca cttatgattg aaaggtttgt gtcattagca attgacgcct  15960
acccacttac aaagcaccct aatcaagagt atgctgatgt tttccattta tacttacagt  16020
atattaggaa attacatgat gagcttaccg gtcacatgtt ggacatgtac tctgtaatgc  16080
taactaatga caacacctca aggtactggg aacctgagtt ttacgaagca atgtacacac  16140
cacacacggt ttacaagct gtgggtgcgt gtgtattatg taattcacag acttcacttc  16200
gttgcggtgc ttgcattagg agacctttcc tttgttgtaa gtgctgctat gatcatgtca  16260
tttcaacatc acataagtta gtgttgtctg ttaatcccta tgtttgcaac gcactaggtt  16320
gtgatgtcac agatgtgaca caactctact taggaggtat gagctattat tgcaagttac  16380
ataaaccacc cattagtttt cctttgtgtg ctaatggtca ggtctttggt ttgtataaaa  16440
acacatgtgt gggcagtgat aatgtaactg acttcaatgc aatagcgaca tgtgactgga  16500
ctaatgctgg cgattatata cttgccaaca cttgcacaga gagactcaaa ctttttgcag  16560
cggaaacgct caaagctact gaggaaacat ttaaactatc ttatggtata gccactgttc  16620
gtgaagtact gtcagataga gagctttatc tttcatggga ggttggaaaa cctagaccac  16680
cattgaatag aaactacgtc tttactggtt accgcgtgac caaaaatagt aaagtacaga  16740
ttggagagta tacctttgaa aaaggtgact atggtgatgc tgttgtgtac agaggtacta  16800
caacatacaa attgaatgtt ggcgattact ttgtgttaac atcacacaca gtaatgccac  16860
taagtgcacc aacactagtg ccacaagagc actatgtgcg aataactggc ttatacccta  16920
cacttaacat ctctgatgag ttttctagca atgttgcaaa ttaccaaaag gtcggtatgc  16980
agaagtactc cacactccaa ggaccacctg gtactggtaa gagtcacttt gctattggac  17040
ttgccctcta ctacccatct gctcgcatag tgtatacagc ttgctctcat gctgctgttg  17100
atgcgctatg tgaaaaggca ttaaaatatt tgcctataga taagtgtagt agaattatcc  17160
ctgcacgtgc gcgtgtagag tgttttgata aattcaaagt gaattcaacc ttagaacagt  17220
```

-continued atgttttctg cactgttaat gctctgcctg aaactactgc tgatatagtg gtctttgatg 17280
aaatttcaat ggccactaat tatgatttga gtgttgtcaa tgctagacta cgtgcaaaac 17340
actacgttta cattggcgat ccagctcaat tacctgcacc acgcacattg ctaacaaaag 17400
gcacacttga accagaatat ttcaattcag tgtgcagact tatgaaaaca ataggtccag 17460
acatgttcct tggaacttgt cgtcgttgtc ctgctgaaat tgttgacaca gtgagtgctt 17520
tagtttatga taataagcta aaagcacaca aagagaagtc agcgcaatgc tttaagatgt 17580
tttataaggg tgtgattacg catgatgtgt catccgcaat aaacagacca caaataggtg 17640
tagtaagaga atttcttaca cgcaaccctg cttggagaaa agctgtcttc atctcaccat 17700
ataattcaca gaacacagtg gcatcaaaga ttttagggtt gccaactcaa actgttgatt 17760
cttcacaggg ttctgaatat gactatgtca tattcacgca aaccactgag actgcacact 17820
cttgtaatgt aaaccgcttt aatgtggcca tcacaagagc aaaaattggc attttgtgca 17880
taatgtctga tagagacctt tatgacaagc tgcaatttac gagtctagaa gtaccgcgtc 17940
gtaatgtggc tactttacaa gcagaaaatg tgactggact ctttaaggac tgtagcaaga 18000
tcattactgg tcttcatcca acacaggcac ctacacatct tagtgttgat actaaattca 18060
aaactgaagg actttgtgtc gacataccag gaataccaaa agacatgacc tatcgtagac 18120
tcatctctat gatgggtttt aaaatgaatt accaagttaa tggttaccct aatatgttta 18180
tcacccgtga agaagctatc cgtcacgttc gtgcgtggat aggctttgat gttgagggtt 18240
gtcatgcgac tagagatgct gtaggaacaa atctaccact ccagttaggg ttttcaacag 18300
gtgttaacct agtgactgta ccaactggct atgttgacac tgagaatagc acagaattca 18360
ccagagttaa tgcaaaacct cctccaggtg atcaatttaa gcatcttata ccacttatgt 18420
acaaaggctt gccctggaac gtggtgcgta ttaagattgt tcaaatgctc agtgacacac 18480
tgaaaggatt atcagacaga gttgtgtttg tcctttgggc gcatggcttt gaactcacat 18540
cgatgaagta ctttgtcaag atcggaccag aaagaacgtg ttgtctgtgt gacaaacgcg 18600
cgacttgctt ctctacttca tctgatactt acgcctgttg gaatcactct gtgggctttg 18660
actatgtcta taacccattc atgattgatg tccagcagtg gggttttaca ggtaaccttc 18720
aaagtaacca tgaccagcac tgccaagtgc atggtaatgc tcatgtagct agttgtgatg 18780
ctatcatgac tagatgtctt gcagtccatg agtgctttgt taagcgtgtt gattggtctg 18840
ttgaataccc aattattgga gatgaactga agattaacgc cgcgtgcaga aaagtacagc 18900
atatggttgt taaatctgca ttgcttgctg ataaattccc agttcttcat gacataggaa 18960
acccaaaggc tattagatgt gtgccgcagg ctgaagtgga ctggaaattc tacgacgctc 19020
agccttgcag tgataaagct tataaaatag aagaactctt ctactcatat gccacacatc 19080
atgacaagtt cacagatggt gtctgcttgt tttggaactg taacgttgat cgttacccgg 19140
ctaatgctat tgtgtgtagg tttgatacta gagtgctttc taatttaaac ctaccaggtt 19200
gtgatggtgg tagtttgtat gttaataagc atgcattcca cactccagct tttgataaga 19260
gtgcatttac acatttgaaa caactgcctt tcttttatta ctctgacagt ccgtgtgagt 19320
ctcatggcaa acaggttgtg tcagatattg attatgtccc actaaagtct gctacgtgta 19380
ttacacgatg caacttaggt ggtgccgttt gtagacatca tgcaaacgag tatagacagt 19440
acttggatgc atataatatg atgatttctg ctggatttag cctttggatt tataaacaat 19500
ttgatactta caacttgtgg aacactttca ccaagttgca gagtttagaa aatgtggctt 19560

```
ataatgttat taacaaggga cactttgatg gacagagtgg tgaagcacct gtgtctatca  19620
ttaataatgc tgtttacact aaggtagatg gtattgatgt ggagatcttt gaaaataaga  19680
caacacttcc tgttaatgtt gcatttgagc tttgggctaa acgtaacatt aaacctgtgc  19740
cagagattaa aatactcaat aatttgggtg ttgatatcgc tgctaatact gttatatggg  19800
accacaagag agaagctcca gcgcatgttt ctacaatagg tgtctgtaca atgactgaca  19860
ttgcagagaa acctactgag aatgcttgtt catcactcac tgtcttattt gatggtagag  19920
ttgagggaca ggcgaacctt tttagaaacg ctcgtaatgg tgttttaata acagaaggtt  19980
cagttaaggg cttaacacct tcgaaaggac ctgcacaggc tagtgtcaac ggggtcacat  20040
taattggaga atcagtaaaa acacagttca attactttaa gaaagtggat ggcattattc  20100
agcaattgcc agaaacttac tttactcaaa gcagagactt agaggatttc aagcccagat  20160
cacaaatgga aactgatttc cttgagctcg ctatggatga attcatagaa cgatataagc  20220
tagacggcta tgctttcgag cacatcgttt atggagattt tagtcatgga caattaggcg  20280
gacttcattt attgatagga ctagccaaaa ggtcacagga ctcactgtta aagctagagg  20340
attttattcc tatggatagc acagtgaaaa actacttcat aacagatgcg caaacgggtt  20400
catctaagtg tgtatgctct gttatcgatc ttttacttga tgactttgtt gaaataataa  20460
agtcacaaga tctttcagtg gtttcaaaag tagtcaaagt tacgattgat tatacagaaa  20520
tttcatttat gctttggtgt aaagatgggc atgtggaaac tttttaccca aaattacaat  20580
ctagccacgc atggcaacca ggtgttgcta tgcctaatct ttataaaatg cagagaatgt  20640
tactggaaaa gtgtgacctt caaaattatg gtgatagtgc tacattgcct aaaggcataa  20700
tgatgaacgt cgcaaagtat actcaactgt gtcagtattt aaatacactt actttagctg  20760
tgccctacaa tatgagagtt atacactttg gcgcaggctc tgataaagga gtagcacctg  20820
gcacagctgt tcttagacaa tggttgccaa ctggtacact acttgtcgat tctgatttaa  20880
atgattttgt ttctgatgca gattcaacat taattggtga ttgtgcaacc gtacatacgg  20940
ctaataaatg ggatctcatt attagcgata tgtatgatcc taagactaaa aatgttacaa  21000
aagagaatga ttccaaagaa ggatttttca cttacatttg tggatttata cagcaaaaat  21060
tagccctcgg aggttccgta gctgtaaaga taacagaaca ttcctggaat gccgatcttt  21120
ataagctcat gggatacttc gcatggtgga cagcttttgt tactaatgtt aatgcttcat  21180
cctcagaggc tttcttaatt ggttgtaatt accttggcaa accacgtgag cagatagatg  21240
gttatgtcat gcatgcaaat tacatatttt ggaggaacac aaatccaata caattgtctt  21300
cctactcatt atttgacatg agtaagtttc ctcttaaatt aagaggtact gctgttatgt  21360
cattaaaaga tggacaaatc aatgatatga ttttgtctct tcttagtaaa ggcagactta  21420
ttgttagaga gaataataga gttattatct ctagtgatgt tcttgttaac aactaaacga  21480
acatgttgtt tttcttgttt cttcagttcg ccttagtaaa ctcccagtgt gatttgacag  21540
gtagaactcc actcaatccc aattatacta attcttcaca aagaggtgtt tattaccctg  21600
acacaattta tagatctgac acactagtgc ttagtcaggg ttattttctt ccattttatt  21660
ccaatgttag ctggtattat tcattaacaa ccaacaatgc tgccacaaag aggactgaca  21720
accctatatt agatttcaag gacggcatat attttgctgc cactgaacac tcaaatattg  21780
tcaggggctg gatctttgga acaactcttg acaacacttc tcaatctctc ttgatagtta  21840
acaatgcaac gaatgttatt atcaaggttt gtaattttga cttttgttac gatccctacc  21900
ttagtggtta ctatcataac aacaaaacct ggagcatcag agaatttgct gtctattcct  21960
```

```
tttatgctaa ttgtactttt gagtatgtct caaaatcctt tatgttgaac atttctggta  22020
atggtggtct gttcaacact ctcagagagt ttgtttttag aaatgtcgat gggcatttca  22080
agatttactc aaaatttaca ccagtaaact taaatcgtgg cttacctact ggtctttcag  22140
tacttcaacc gttggttgaa ttaccagtta gcataaatat tactaaattt agaacactcc  22200
tcactattca tagaggagac cctatgtcta ataatggctg gactgctttt tcagctgctt  22260
atttcgtggg ctatcttaaa ccacgtacct ttatgctgaa atataatgag aatggcacca  22320
ttactgatgc tgttgattgt gcacttgacc ctctttcgga gacaaagtgt acgttaaaat  22380
ctcttagtgt tcaaaagggt atctatcaga cttctaactt tcgagtgcaa cccactcagt  22440
ctatagttag atttcctaat attaccaatg tgtgtccatt tcacaaggtt tttaatgcca  22500
caaggtttcc ttctgtttac gcgtgggaaa gaactaaaat ttctgattgc attgcagact  22560
acactgtttt ctacaattca acttcttttt ctactttcaa atgttatggt gtttcaccct  22620
ctaaattgat tgatttgtgt tttacgagtg tgtatgctga tacatttctc ataagatttt  22680
cagaggtcag acaagtggca ccaggacaga ctggtgttat tgctgactac aattataaat  22740
tacctgatga ttttacaggt tgtgtcatag cctggaacac agcaaaacag gacacaggtc  22800
attatttcta taggtctcat cgctctacca aattaaaacc atttgaaaga gacctttctt  22860
cagatgagaa tggtgtccgt acacttagta cttatgactt taaccctaat gtaccgcttg  22920
aatatcaagc tacaagggtt gttgtcttgt catttgagct tctaaatgca ccagctacag  22980
tttgtggacc aaaattatcc acacaactag taaaaaatca gtgcgttaat ttcaatttta  23040
acggactcaa gggcactggt gtcttgactg attcttctaa gaggtttcag tcattccaac  23100
aatttggtaa agatgcgtct gactttattg attcagtacg tgatcctcaa acacttgaga  23160
tacttgacat tacaccttgc tcttttggtg gtgtcagtgt tataacacca ggaacaaaca  23220
cttcttcaga ggtggctgtt ctttaccaag atgttaactg cactgatgta ccaactacta  23280
tacatgcaga ccaattaaca cctgcttggc gcatttatgc tattggcact agtgtgtttc  23340
aaactcaagc aggctgtctt ataggagctg aacatgtcaa tgcttcttat gagtgtgaca  23400
tcccaattgg tgctggtatt tgtgctagct accatacggc ttctatatta cgtagtacag  23460
gccagaaagc tattgtggct tatactatgt cccttggtgc tgagaactct attgcttatg  23520
ctaacaattc tatagccata cctacaaatt tttcaatcag tgtcaccact gaagttatgc  23580
ctgtatcaat ggctaaaact tctgtagatt gcactatgta tatctgcggt gactctatag  23640
agtgtagcaa cttgttgtta caatatggca gtttttgcac acaactaaat cgtgctttaa  23700
gtggaattgc tattgaacaa gacaagaaca ctcaagaggt ttttgctcaa gtcaagcaaa  23760
tctataaaac accacctatt aaggattttg gtggtttcaa tttttcacag atattacccg  23820
atccttctaa acccagcaag aggtcgttta ttgaagattt actcttcaat aaagtcactc  23880
ttgctgatgc tggttttata aaacagtacg gtgattgttt gggtgatatt tctgctagag  23940
atttgatttg tgctcaaaag ttcaatggac tcactgtctt accaccattg ctcacagatg  24000
aaatgatcgc tgcttataca gctgcattaa ttagcggcac tgccactgct ggatggacct  24060
ttggtgctgg tgctgctctt caaataccat ttgccatgca aatggcttat agatttaatg  24120
gaattggagt tactcagaat gttctctatg agaatcagaa attaatagcc aatcagttta  24180
atagtgctat tggaaaaatc caagagtctt tgacatctac agctagtgca cttggaaaat  24240
tgcaggatgt tgttaaccaa aatgcacaag ctttaaacac gcttgttaaa caacttagtt  24300
```

-continued

```
ccaattttgg tgcaatttca agcgtgttga atgatattct ttcacgcctt gacaaagtcg  24360
aggctgaggt tcagattgat aggttgatca caggtagact tcagagttta cagacgtatg  24420
tgactcaaca attaatcaga gctgcagaaa tcagagcttc tgctaatctt gctgcgacta  24480
aaatgtccga gtgtgtacta ggacaatcta aaagagttga tttttgtgga aaaggttatc  24540
acctaatgtc ttttccccag tcagcgcctc atggtgttgt tttcttacat gtgacttaca  24600
ttccttcgca agaaaagaac ttcacaacag ctcctgccat ttgtcatgaa ggtaaagcac  24660
acttcccacg tgaaggtgtt ttcgtttcga atggcacaca ctggtttgta acacaaagga  24720
acttttacga accccaaatt ataaccactg acaatacatt tgtctccggt aactgtgatg  24780
ttgtaattgg aattatcaat aacacagttt atgatccttt acaaccagaa cttgattcat  24840
ttaaggagga gttagataaa tattttaaaa atcatacatc acctgatatt gatcttggtg  24900
atatttctgg cattaatgct tctgttgtca atattcaaaa ggaaattgac cgcctcaatg  24960
aggttgccag aaatttaaat gaatcactca ttgatctcca agaacttgga aaatatgagc  25020
actatatcaa atggccatgg tatgtttggc tcggcttcat tgctggactc attgctatag  25080
tcatggttac aatcctgctt tgttgcatga caagttgttg cagttgtctc aagggctgtt  25140
gttcttgcgg attttgctgt aaatttgatg aagatgactc tgagcctgtg ctcaaaggag  25200
tcaaattaca ttacacgtaa acgaacttat ggatttgttt atgagaattt tcacacttgg  25260
aactgtaagt ctgaaacaag gtgaaattaa ggatgctact ccttcagatt ctattcgcgc  25320
tactgcaaca ataccgatac aagccacact ccctttcgga tggcttgttg ttggcgttgc  25380
aattcttgct gtttttcaaa gcgcttcaaa aataattaca ctcaaaaaga gatggcagtt  25440
agccctctct aaaggtgtcc actttgtttg caacttgctt ctgctgtttt taacagttta  25500
ctcacaccta ttgcttgttg ctggtggctt agaagccact tttctttttc tttatgcatt  25560
agcttattgc ttgcaaactg taaattttgt gagaataata atgcgattct ggttgtgctg  25620
gaagtgccgc tccaagaatc ctgtacttta tgatgccaac tactttcttt gttggcatac  25680
taattgttat gactattgta taccatacaa tagtgtaacc tcttcaatcg tcatcacatg  25740
tggtgatggt actacgaatc ccatttctga ggatgactac caaattggtg gttacacgga  25800
aaagtgggag tctggtgtta aggactgtgt tgtattacat agttatttca cctcagacta  25860
ctaccagctg tactcaacac aattgagcac agacactggt gttgaacatg ttactttctt  25920
catctacaat aaaattgttg atgagcctga agaacatgtc caaattcaca caatcgacgg  25980
tacatctgga gttgttaatc cagcaatgga accaatttat gatgaaccga cgacgactac  26040
tagcgtgcct ttgtaagcac aagctgatga gtacgaactt atgtactcat tcgtttcgga  26100
agagacaggt acgttaatag ttaatagcgt acttcttttt cttgcttttg tggtattctt  26160
gctagtcaca ctagccatcc ttactgcgct tcgattgtgt gcgtactgct gcaatattgt  26220
taacgtgagt cttgtaaaac cttcttttta cgtttactct cgtgttaaaa atctgaattc  26280
ttctagagtt cctgatcttt tggtctaaac gaactaaata ttatattagt ctttctgttt  26340
ggaactttaa ttttagccat gtcaggtgac aacggtacca ttaccgttga agagcttaaa  26400
aagctcttag aacaatggaa cctagtaata ggattcttgt ttcttacatg gatttgtttg  26460
ttacaatttg cctatgccaa caggaatagg tttttgtaca taattaagtt aattttcctc  26520
tggctgcttt ggccagtaac tttagcttgc tttgtgcttg ctgctgttta cagaataaac  26580
tggatcactg gtggaattgc cattgcaatg gcctgtcttg taggcttgat gtggcttagc  26640
tacttcattg cttctttcag gctgtttgct cgtacgcgtt ccatgtggtc atttaaccca  26700
```

-continued

```
gaaactaaca ttcttttgaa cgtgcctctt catggcacaa ttctgaccag gccgcttcta  26760
gagagtgaac tcgtaattgg agctgtgatc cttcgtggac atcttcgtat tgcaggacac  26820
catctgggac gctgtgacat caaggacctg cccaaagaaa tcactgtagc tacatcacga  26880
acgctttctt attacaaatt gggagcttcg cagcgtgtag caggtgactc aggttttgct  26940
gcatacagtc gctacaggat tggtaattac aaattaaata cagaccattc cagtagcagt  27000
gacaatattg ctttgcttgt acagtaagtg acaacagatg tttcatctcg ttgactttca  27060
ggttactata gcagagatat tattaattat tatgaggact tttaaagttt ccatttggaa  27120
tcttgattat atcataaatc tcataattaa aaatctatct aagcctccaa ctgagaataa  27180
ctgttctcaa ttagatgaag agcaaccaat ggagattgat taaacgaaca tgaaaattat  27240
tttcttcttg gtactgataa cacttgttac tggcgagctt taccactacc aagagtgtat  27300
aaaaggtaca actgtacttt taaaagaacc ttgctcttca ggaacatatg aaggcaattc  27360
accatttcat cctctagctg ataataaatt tgcactgact tgctttagca ctcaatttgc  27420
ttttgcttgt cctgacggtg ttagacacac ctttcagtta cgtgcgagat cagtttcacc  27480
caaactgttt accagacaag aggaagttca agaattatac tcacctgttt tccttatcgt  27540
tgcagctata gtgttcataa tactttgctt cacattcaaa agaaaaatag aatgagtgaa  27600
ttttcattaa ttgacttcta tttgtgcttc ttagcctttc tgctattcct tgttttaatt  27660
atgctcatta tcttttggtt ctcactagaa ctgcaagatc ataatgaaac ttctcacgcc  27720
taaacgaata tgaaatttct tgttttctta ggaattctta caacagtagc tgcattccat  27780
caggaatgta gtttacagtc atgtgctcaa catcaaccct atgtagttga tgacccttgt  27840
ccaattcact tctactcacg atggtatatc agagtgggag ctagaaaatc agcacctttg  27900
attgaattgt gtgttgacga ggtaggctct aagtcaccca ttcaatacat tgacattggt  27960
aattacacag tttcctgttc tcctttttaca attaattgcc aggaacctaa attaggtagt  28020
ctcgtagtac ggtgttcgta ttatgaagac tttctagagt accatgacat tcgtgttgtc  28080
ttagatttca tctaaacgaa ctaactaaaa tgtctgataa tggaccccaa aaccagagta  28140
gtgcaccccg cattacattt ggtggaccct cagattcaag tgacaatagc caaaacggag  28200
agcgcaatgg tgcacgacct aaacaacgtc gaccccaagg cttacccaat aatactgcat  28260
cttggttcac cgctctcact caacatggca aggaaaacct tacgttccct cgagggcaag  28320
gtgttccaat taacaccaat agctctaaag atgaccaaat tggctactac cgtagagcta  28380
ccagacgaat tcgtggcggt gacggtaaaa tgaaagagct cagccccaga tggtattttt  28440
actatctggg aactggacca gaagctggac ttccctatgg tgctaacaaa gaaggcatca  28500
tatgggttgc aactgaggga gccttaaaca caccaaaaga ccacattggc acccgcaatc  28560
ctgctaacaa tgctgcaatc gtgctacaac ttcctcaagg aacaacattg ccaaaaggct  28620
tctacgcaga agggagcaga ggcggcagtc aagcttcttc acgctcctca tcacgtagtc  28680
gcaacagttc aagaaactca actccaggca gcagtagggg aacttctcct gctagaatgg  28740
ctggcaatgg cggtgacact gctcttgctt tgctgctgct agataggttg aaccagcttg  28800
agaacaagat atctggcaaa ggccaacaac aacaaggcca aactgtcact aagaaatctg  28860
ctgctgaggc atctaaaaag cctcgccaaa aacgtactgc cacaaaacag tacaacgtca  28920
ctcaagcatt tgggagacgt ggtccagaac aaacccaagg aaatttcggg gaccaagaat  28980
taatcagaca aggaactgat tacaaacatt ggccgcaaat tgcacaattt gctccaagtg  29040
```

-continued

| | |
|---|---|
| cctctgcatt ctttggaatg tctcgcattg gcatggaagt cacaccttcg ggaacatggc | 29100 |
| tgacttatca tggagccatt aaattggatg acaaagatcc acaattcaaa gacaacgtca | 29160 |
| tactgctgaa taagcacatt gacgcataca aaacattccc accaacagag cctaaaaagg | 29220 |
| acaaaaagaa aaaggctgat gaacttcagg ctttaccgca gagacagaag aagcaacaaa | 29280 |
| ctgtgactct tcttcctgct gcagatttgg atgaattctc caaacagttg caacaatcca | 29340 |
| tgagtggtac tgattcaacc caggcttaaa ctcatgcaga ccacacaagg cagatgggct | 29400 |
| atataaacgt tttcgctttc cgtttacgat atatagtcta ctcttgtgca gaatgaattc | 29460 |
| tcgtaactac atagcacaag tagatgtagt taactttaat ctcacatagc aatctttaat | 29520 |
| caatgtgtaa cattagggag gatttgaaag agccaccacg ttctcaccga ggccacgcgg | 29580 |
| agtacgatcg agggtacagt gaataatgtt agggagagca gcctatatgg aagagcccta | 29640 |
| atgtgtaaaa ttaattttag tagtgctatc cccatgtgat tttaatagct tcaaccactc | 29700 |
| gacaagaaaa aaaaaaaaaa aaaaaaaaaa aa | 29732 |

ANTIVIRAL AGENTS FOR TREATMENT OF CORONAVIRUSES

CROSS-REFERENCE TO RELATED APPLICATIONS

This application claims the benefit of U.S. Provisional Patent Application No. 63/017,603, filed Apr. 29, 2020, which is incorporated by reference herein in its entirety.

INCORPORATION-BY-REFERENCE OF SEQUENCE LISTING

The material in the accompanying sequence listing is hereby incorporated by reference in its entirety into this application. The accompanying file, named Sequences_212149-401055_V2.txt, was created on Jul. 21, 2021, and electronically submitted via EFS-Web on Sep. 21, 2021, and is 115 KB.

BACKGROUND

A. Field of the Disclosure

The present disclosure relates generally to medicine, specifically to antiviral agents, and particularly antiviral agents for the treatment of coronaviruses, such as SARS-CoV-2. Such agents, methods of use, and kits for use therefor are provided.

B. Background

Severe acute respiratory syndrome coronavirus 2 (i.e., "SARS-CoV-2") is a strain of virus that causes coronavirus disease 2019 (i.e., COVID-19). SARS-CoV-2 is a novel coronavirus that is highly transmissible and pathogenic for humans (and potentially other animals) and can cause life-threatening illness (particularly respiratory disease), especially in individuals with underlying comorbidities or are otherwise in a sensitive group (e.g., immunocompromised or immunosuppressed). Because of the effects of SARS-CoV-2 on an infected individual's respiratory system, a percentage of those infected require breathing support, such as by oxygen infusion and/or a mechanical ventilator. On Mar. 11, 2020, the Worldwide Health Organization ("WHO") declared COVID-19 to be a pandemic—the first time a pandemic had been declared by WHO since H1N1 (the virus that causes the disease known as "swine flu") in 2009. This declaration tracked the global spread of the virus, with national and local governments worldwide enacting various social distance measures to limit the spread of COVID-19 in an effort to avoid overwhelming medical capacity and resources (such as available hospital beds and ventilators).

Coronaviruses (CoVs) are positive-sense, single-stranded, enveloped, RNA viruses that belong to the subfamily Coronavirinae, family Coronavirdiae, order Nidovrales and are classified into four genera of CoVs: namely, Alphacoronavirus (αCoV), Betacoronavirus (βCoV), Deltacoronavirus (δCoV), and Gammacoronavirus (γCoV). To date, seven human coronaviruses (HCoVs) have been identified, including two α-CoVs (HCoV-229E and HCoVNL63) and five β-CoVs (HCoV-OC43, HCoV-HKU1, severe acute respiratory syndrome CoV (SARS-CoV), Middle East respiratory syndrome CoV(MERS-CoV), and most recently β-CoV SARS-CoV-2 (COVID-19). WHO has classified COVID-19 as a βCoV of group 2B. CoVs cause respiratory, enteric, hepatic, and neurological diseases in humans among other different animal species, including camels, cattle, cats, and bats. The βCoV lineage HCoV-OC43 and HCoV-HKU1 are typically associated with self-limiting upper respiratory infections in immunocompetent hosts and occasionally lower respiratory tract infections in immunocompromised hosts and the elderly. Coronaviruses possess the largest genomes of all RNA viruses, consisting of about 30 kb.

SARS-CoV-2 belongs to the βCoV genera and has 89% nucleotide identity with bat SARS-like-CoVZXC21 and 82% with that of human SARS-CoV. Examinations of the viral evolution show that bats and rodent are gene sources for most αCovs and βCoVs while avian species are the proposed gene sources of most δCoVs and γCoVs. CoVs often cross species barriers to infect humans and have emerged to cause significant morbidity and mortality in the general population. The most recent examples are severe acute respiratory syndrome CoV (SARS-CoV) that emerged in China in 2002 with 8000 infections and 800 deaths (generally known as the SARS epidemic) and the and Middle East Respiratory Syndrome CoV (MERS-CoV) that emerged in the Arabian Peninsula since 2012. Developing an antiviral for COVID-19 requires consideration of its genetic complexities as well as the potential to mutate in humans or a zoonotic intermediate host.

Currently, there are no FDA approved treatments for COVID-19, particularly treatments that are effective against SARS-CoV-2. Moreover, there is no current vaccine to prevent COVID-19. This represents an urgent unmet medical need for efficacious therapeutics for COVID-19. Even if a vaccine were to be developed, there is an acute and short to medium-term need in the meantime for therapeutic interventions to treat COVID-19 and/or prevent or reduce transmission. Moreover, a treatment effective against SARS-CoV-2 is needed for other animal hosts, whether to eliminate zoonotic host-mediated infection or to reduce the risk of mutation in a zoonotic intermediate host to a novel strain of coronavirus.

SUMMARY

The problems expounded above, as well as others, are addressed by the invention of an antiviral agent that effectively prevents the replication of strains of coronaviruses, including SARS-CoV-2 (although it is to be understood that not all such problems will be addressed by every such embodiment).

In a first aspect, an antiviral agent is provided, the antiviral agent comprising a phosphorodiamidate morpholino oligomer comprising an antisense sequence to a portion of a genome of a strain of a coronavirus (such as a strain of SARS-CoV-2).

In a second aspect, a pharmaceutical composition for the treatment or prevention of a disease mediated by a coronavirus (such as SARS-CoV-2) is provided, the composition comprising: the antiviral agent above and a pharmaceutically acceptable carrier.

In a third aspect, a method of treatment or prevention of a disease mediated by a strain of a coronavirus (such as SARS-CoV-2) in a subject in need thereof is provided, the method comprising administering to the subject a therapeutically effective amount of the antiviral agent or the pharmaceutical composition above.

In a fourth aspect, a method of reducing or preventing the replication of a strain of a coronavirus (such as SARS-CoV-2) in a host cell is provided, the method comprising contacting the host cell with the antiviral agent above.

In a fifth aspect, a method of controlling the spread of a strain of a coronavirus (such as SARS-CoV-2) in donated tissue is provided, the method comprising exposing the donated tissue to an effective amount of the agent above.

In a sixth aspect, a treated donated tissue sample is provided, comprising a sample of donated tissue and the agent above.

In a seventh aspect, a use of the agent above in the manufacture of a medicament for the treatment or prevention of a disease mediated by a strain of a coronavirus (such as SARS-CoV-2) is provided.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

DETAILED DESCRIPTION

A. Definitions

Figure 1:
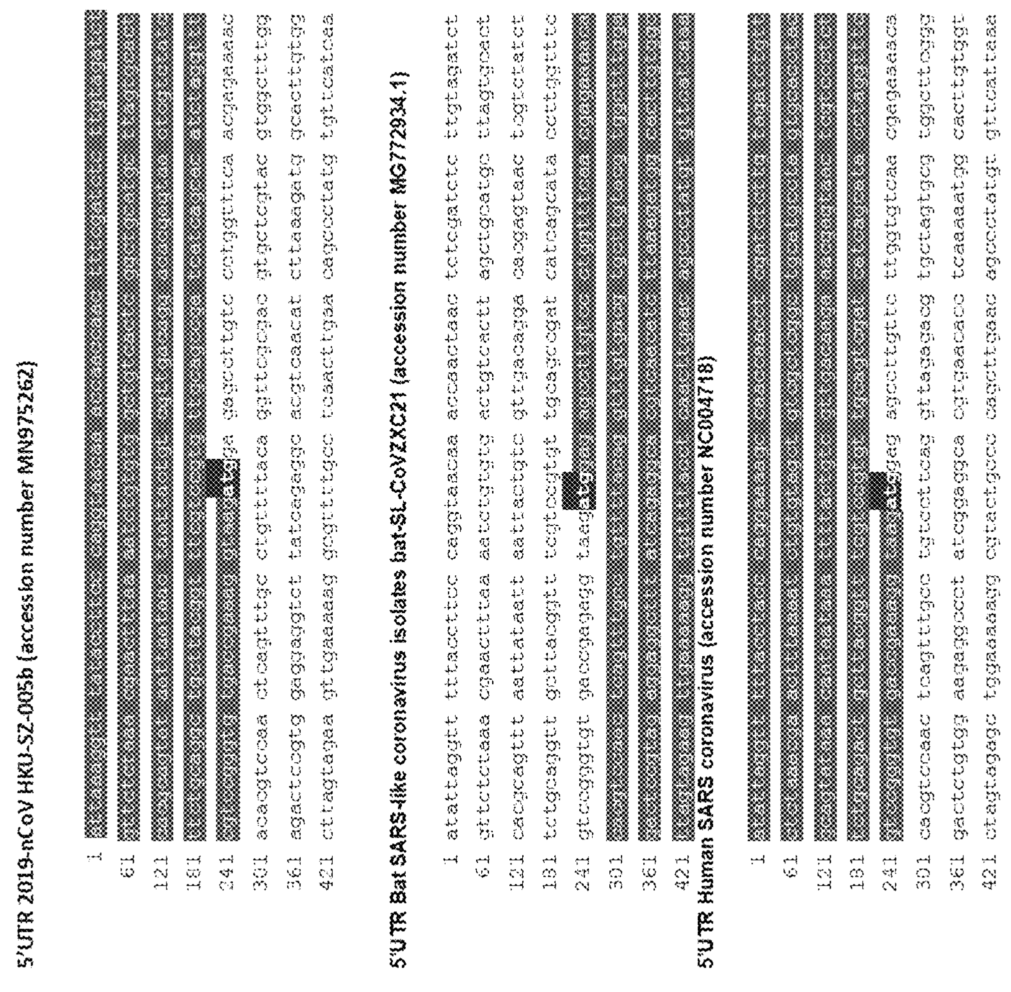
FIG. 1: Sequences of the 5'UTR for SARS-CoV-2, the bat SARS-like-CoVZXC21, and SARS-CoV are depicted, with the start site for pp1a (atg) shown in highlighting with white text.

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense unless expressly so defined herein. Well-known functions or constructions may not be described in detail for brevity or clarity.

The terminology used herein is for the purpose of describing particular embodiments only and is not intended to be limiting. As used herein, the singular forms "a," "an," and "the" are intended to include the plural forms as well, unless the context clearly indicates otherwise.

The terms "first," "second," and the like are used herein to describe various features or elements, but these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present disclosure.

The term "consisting essentially of" means that, in addition to the recited elements, what is claimed may also contain other elements (steps, structures, ingredients, components, etc.) that do not adversely affect the operability of what is claimed for its intended purpose as stated in this disclosure. This term excludes such other elements that adversely affect the operability of what is claimed for its intended purpose as stated in this disclosure, even if such other elements might enhance the operability of what is claimed for some other purpose.

The terms about and "approximately" shall generally mean an acceptable degree of error or variation for the quantity measured given the nature or precision of the measurements. Typically, exemplary degrees of error or variation are within 20 percent (%), preferably within 10%, and more preferably within 5% of a given value or range of values. For biological systems, the term "about" refers to an acceptable standard deviation of error, preferably not more than 2-fold of a given value. Numerical quantities given herein are approximate unless stated otherwise, meaning that the term 'about' or "approximately" can be inferred when not expressly stated.

The terms "prevention," "prevent," "preventing," "suppression," "suppress," and "suppressing," as used herein, refer to a course of action (such as administering a pharmaceutical composition) initiated prior to the onset of a clinical manifestation of a disease state or condition so as to reduce its likelihood or severity. Such a reduction in likelihood or severity need not be absolute to be useful.

The terms "treatment," "treat," and "treating," as used herein, refer to a course of action (such as administering a pharmaceutical composition) initiated after the onset of a clinical manifestation of a disease state or condition so as to eliminate or reduce such clinical manifestation of the disease state or condition. Such treating need not be absolute to be useful.

The term "in need of treatment," as used herein, refers to a judgment made by a caregiver that a patient requires or will benefit from treatment. This judgment is made based on a variety of factors that are in the realm of a caregiver's expertise, but that judgment includes the knowledge that the patient is ill, or will be ill, as the result of a condition that is treatable by a method or device of the present disclosure.

The term "in need of prevention," as used herein, refers to a judgment made by a caregiver that a patient requires or will benefit from prevention. This judgment is made based on a variety of factors that are in the realm of a caregiver's expertise, but that judgment includes the knowledge that the patient will be ill or may become ill, as the result of a condition that is preventable by a method or device of the disclosure.

The terms "individual," "subject," or "patient," as used herein, refer to any animal, including mammals, such as mice, rats, other rodents, rabbits, dogs, cats, swine, cattle, sheep, horses, primates, and humans. The term may specify male or female or both, or exclude male or female.

The term "therapeutically effective amount" (or simply "effective amount"), as used herein, refers to an amount of an agent, either alone or as a part of a pharmaceutical composition, that is capable of having any detectable, positive effect on any symptom, aspect, or characteristics of a disease state or condition. Such an effect need not be absolute to be beneficial.

The term "pharmaceutically acceptable salts," as used herein, includes salts of the antiviral agents which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogen carbonic, phosphoric, monohydrogen phosphoric, dihydrogen phosphoric, sulfuric, monohydrogen sulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts," Journal of Pharmaceutical Science, 1977, 66, 1-19). Certain specific compounds of the present invention contain both basic and acidic functionalities that allow the compounds to be converted into either base or acid addition salts.

Nucleic acids are "complementary" to each other, as used herein, when a nucleotide sequence in one strand of a nucleic acid, due to orientation of its nucleotide hydrogen atoms, hydrogen bonds to another sequence on an opposing nucleic acid strand (of course, a strand of a nucleic acid may be self-complementary as well). The complementary bases typically are, in DNA, A with T, and C with G, and, in RNA, C with G, and U with A. Complementary can be perfect or substantial/sufficient. Perfect complementarity between two nucleic acids means that the two nucleic acids can form a duplex in which every base in the duplex is bonded to a complementary base by Watson-Crick pairing. "Substantial" or sufficient complementarity means that a sequence in one strand is not perfectly complementary to a sequence in an opposing strand, but that sufficient bonding occurs between bases on the two strands to form a stable hybrid complex at a given set of hybridization conditions (e.g., salt concentration and temperature). Such conditions can be predicted by using the sequences and standard models to predict the $T_m$ of hybridized strands, or by empirical determination of $T_m$ by using established methods. $T_m$ refers to the temperature at which a population of hybridization complexes formed between two nucleic acid strands are 50% denatured. At a temperature below the $T_m$, the formation of a hybridization complex is favored, whereas at a temperature above the $T_m$, melting or separation of the strands in the hybridization complex is favored. Such stringency is based on the melting temperature ($T_m$) of the nucleic acid binding complex, as taught in Berger and Kimmel (1987, Guide to Molecular Cloning Techniques, Methods in Enzymology, 152, Academic Press, San Diego CA.). The $T_m$ of an annealed duplex depends on the base composition of the duplex, the frequency of base mismatches, and the ionic strength of the reaction medium. The $T_m$ of a duplex can be calculated by those of ordinary skill in the art based on these two factors using accepted algorithms. Maximum stringency typically occurs at about 5° C. below $T_m$; high stringency at about 5-10° C. below $T_m$; intermediate stringency at about 10-20° C. below $T_m$; and low stringency at about 20-25° C. below $T_m$. As will be understood by those of skill in the art, a maximum stringency hybridization can be used to identify or detect identical nucleotide sequences while an intermediate (or low) stringency hybridization can be used to identify or detect similar or related sequences. Terms such as maximally stringent, highly stringent, and poorly stringent, refer to conditions of maximal stringency, high stringency, and low stringency respectively.

In the following discussion certain outside documents are referenced to enable the reader to make and use the subject matter described herein. Nothing contained herein is to be construed as an 'admission' of prior art. Applicant expressly reserves the right to demonstrate, where appropriate, that such documents referenced herein do not constitute prior art under the applicable statutory provisions.

B. Antiviral Agents

A phosphorodiamidate morpholino oligomer (PMO) is disclosed that suppresses viral replication in strains of coronaviruses, such as SARS-CoV-2. In the interest of clarity, not all features of an actual implementation are described in this specification. It will, of course, be appreciated that in the development of any such actual embodiment, numerous implementation-specific decisions must be made to achieve the worker's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

PMOs are nucleic acids having conventional nucleotide bases, but a backbone of methylenemorpholine rings and phosphorodiamidate linkages. PMO bind to RNA with high specificity. This gives PMOs the ability to block the translation of mRNA by binding to complementary sequences on the mRNA, which prevents binding of the mRNA to the ribosome. Translational blocking with PMOs is highly specific and does not result in blocking of non-target mRNA. PMOs are also much more stable than RNA and resistant to most exonucleases. An unmodified PMO has the following general structure, with each "B" being independently selected from adenine, cytosine, guanine, or thymine:

Form. 1

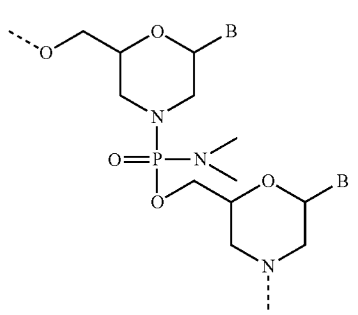

The PMO of the antiviral agent comprises a nucleotide sequence that is complementary to a sequence in a viral genome (the "target sequence"). Such a complementary sequence is referred to herein as the "antisense sequence," although as explained below, in some embodiments the sequence may deviate from an exact antisense sequence of the target. The genome may be, without limitation, the genome of a single-stranded positive sense RNA virus, such as a flavivirus or coronavirus. In a specific embodiment of the agent, the genome is a genome of a strain of a coronavirus, such as SARS-CoV-2. The sequence in the viral genome should be a sequence that must bind to the cellular ribosome for replication to occur. This may be a sequence in a structural gene (i.e., in an open reading frame), or it may be a non-translated sequence that facilitates the binding of the strand to the ribosome.

For purposes of illustration, the SARS-CoV-2 genome will be used as an example. The SARS-CoV-2 genome comprises an untranslated 5' region ("UTR") translation initiation complex that overlaps with the pp1a start site of translation. It is believed that this portion of the SARS-CoV-2 genome is higher conserved (i.e., shares a high degree of identity) among βCoV, including SARS-CoV, SARS-CoV-2, and bat SARS-like-CoVZXC21 (FIG. 1). The SARS-CoV-2 genome has been assigned GENBANK accession number MN975262, and is incorporated herein by reference in its entirety (SEQ ID NO: 5). The SARS-CoV genome has been assigned GENBANK accession number AY278741, and is incorporated herein by reference in its entirety (SEQ ID NO: 6). The bat SARS-like-CoVZXC21 genome has been assigned GENBANK accession number MG772934, and is incorporated herein by reference in its entirety (SEQ ID NO: 7). The ZIKV genome is flanked by a 5' untranslated region (UTR) and 3' UTR. Without wishing to be bound by any hypothetical model, the interaction between 5' and 3' UTRs are believed to be critical for viral RNA replication, with sequences across the UTRs being highly conserved across strains of coronaviruses and specifically βCoV.

In some embodiments of the agent, the target sequence is a sequence from the 5' region of a strain of coronavirus (such as SARS-CoV-2) genome, for example, the region encompassing the pp1a gene region and the 5' untranslated region (UTR). In a specific embodiment of the agent, the target sequence comprises 5'-AGG TAA GAT GGA GAG CCT TGT CCC T-3' (SEQ ID NO: 2) from the 5' UTR. In the same specific embodiment, the PMO comprises the sequence 5'-AGG GAC AAG GCT CTC CAT CTT ACC T-3' (SEQ ID NO: 1).

In a specific embodiment of the agent, the PMO comprises the sequence 5'-AAG AAC AAG GCT CTC CAT CTT ACC T-3' (SEQ ID NO: 3) the targets 5'-GCT GGG AAA GAC CAG AGA CTC CAT G-3' (SEQ ID NO: 4). In some embodiments, the antisense sequence will bind with high stringency to the target sequence under physiological (intracellular) conditions. Such conditions are understood by those of ordinary skill in the art but will vary by cell type. For example, intracellular pH and sodium concentration vary in a narrow range by cell type. Physiological conditions for human subjects are generally at 37° C. (98.6° F.). Typically, this means that the antisense sequence will have at least 80% identity with an exact complement of the target sequence. In various embodiments of the agent the antisense sequence will have at least 70%, 85%, 90%, 95%, 96%, 97%, 98%, or 99% identity with an exact complement of the target sequence. In a specific embodiment, the antisense sequence is an exact complement of the target sequence.

Figure 2A:
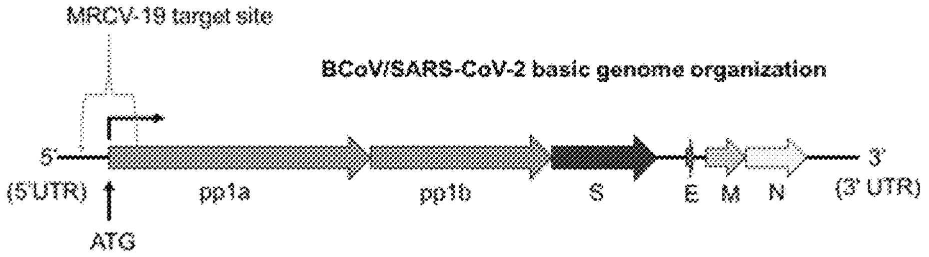
FIG. 2A: A genome organization of βCoV is illustrated.
Figure 2B:
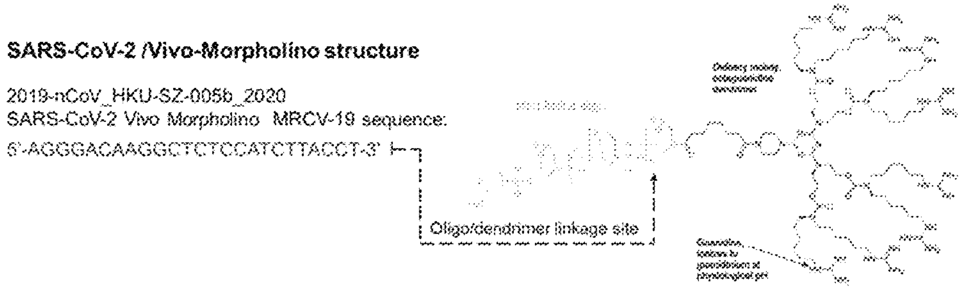
FIG. 2B: A schematic structure of a vivo-morpholino composed of a 25-mer long morpholino oligonucleotide covalently linked to an octaguinidine dendrimer, which serves as a delivery moiety. A nucleotide sequence of SARS-CoV-2 (2019-nCoV_KHU-SZ-005b_2020 vivo-morpholino (i.e., MRCV-19) that is complementary to SARS-CoV-2 target sequence is also shown.

The antisense sequence will generally be about 25 bases long or exactly 25 bases long. In some embodiments, the length of the antisense sequence can vary somewhat, in the range of about 10-30 bases. Specific embodiments of the antisense sequence can be any length from 10-30 bases. More specific embodiments are 15-25 bases. A particular embodiment of antisense sequence is exactly 25 bases long. The PMO may comprise additional nucleotides on the 5'end or 3' end (or both) of the target recognition sequence. In a specific embodiment, the antisense sequence is the entire nucleotide sequence of the PMO, and there are no additional nucleotides on the 5' end or the 3' end of the antisense sequence. Advantageously, it has been discovered that portions of 5' UTR sequences among different coronaviruses, and in particular βCoV, are highly conserved and share a high degree of identity. Referring to FIGS. 1-2B, the sequences representing the 5'UTR for SARS-CoV-2, the bat SARS-like-CoVZXC21, and SARS-CoV are shown (FIG. 1). The start site for pp1a (atg) is shown in highlighting with white text (FIG. 1). A complementary sequence that overlaps the 5'UTR and the regions immediately downstream of the ATG start site was identified as the target to engage the SARS-CoV-2 virus upon entry into permissive cells in vitro and in vivo based on its genome structure (FIG. 2A). The structure of the in vivo morpholino and the complementary sequence targeting SARS-CoV-2 genome are shown in FIG. 2B.

The PMO may have other various desirable characteristics. These may include without limitation: a base sequence that has very little self-complementarity; a high enough GC-content (guanine-cytosine content) (e.g. 40-60%) so that it has a high target affinity; and no stretches of four or more contiguous G to preserve water solubility.

The PMO may have modified 3' or 5' ends to add various additional functionalities. Such modifications can include 3' conjugation with any of: a fluorophore, a quencher, carboxyfluorescein, lissamine, dabcyl, biotin, amine, amine with biotin, disulfide amine, pyridyl dithio, azide, and alkyne. Such modifications may include 5' conjugation with any of: a primary amine, dabcyl, azide, and alkyne. In a specific embodiment of the agent, the PMO is modified for intracellular delivery.

Modifications for cellular delivery may include endocytosis-stimulating peptides, such as weak-base amphiphilic peptides taught in U.S. Pat. No. 7,084,248 and commercially available under the tradename ENDO PORTER from Gene Tools, LLC (Philomath, OR, USA). In another example, the PMO is conjugated to an octa-guanidine dendrimer. A specific embodiment of the octa-guanidine dendrimer has the following structure:

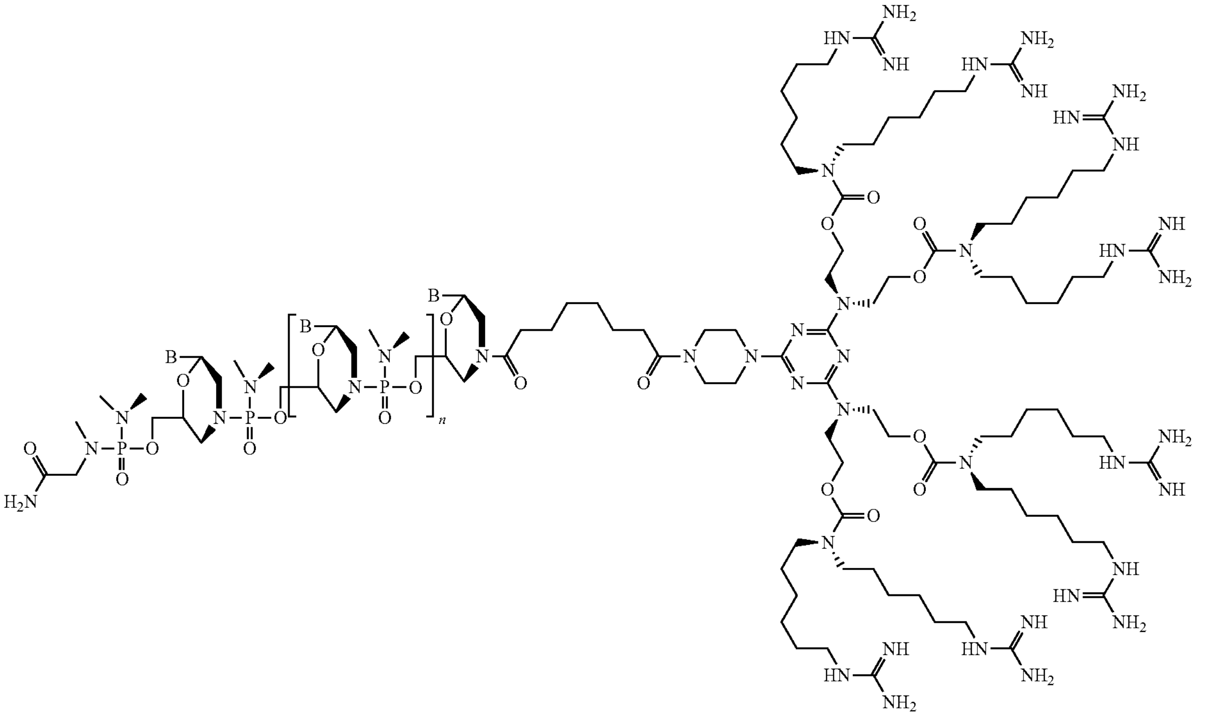

C. PHARMACEUTICAL COMPOSITIONS

A pharmaceutical composition for treating or preventing a disease mediated by a strain of a coronavirus (such as SARS-CoV-2) is provided, the composition comprising any of the antiviral agents provided above. The compositions disclosed may comprise one or more of such antiviral agents, in combination with a pharmaceutically acceptable carrier. Examples of such carriers and methods of formulation may be found in Remington: The Science and Practice of Pharmacy (20th Ed., Lippincott, Williams & Wilkins, Daniel Limmer, editor), and are generally well understood by those skilled in the art. To form a pharmaceutically acceptable composition suitable for administration, such compositions will contain a therapeutically effective amount of an antiviral agent.

The pharmaceutical compositions of the disclosure may be used in the treatment and prevention methods of the present disclosure. Such compositions are administered to a subject in amounts sufficient to deliver a therapeutically effective amount of the antiviral agent so as to be effective in the treatment and prevention methods disclosed herein. The therapeutically effective amount may vary according to a variety of factors such as the subject's condition, weight, sex, and age. For example, some embodiments of the composition comprise up to the median lethal dose ($LD_{50}$) of the antiviral agent. The $LD_{50}$ can be ascertained using standard toxicological methods, or by reference to past studies. Alternatively, the pharmaceutical composition may be formulated to achieve a desired concentration of the antiviral agent at the site of the infection.

The toxicities of PMOs are generally very low. In some embodiments of the pharmaceutical composition, the PMO is administered to the subject in an amount of up to 0.05, 0.1, 0.15, 0.2, 0.3, 0.5, 1, 1.5, 2, 3, 5, 10, 15, 20, 30, 50, 100, 200, and 500 mg/kg, about any of the foregoing values, and a range between any of the foregoing values. The PMO may be administered to the subject, such as in a pharmaceutical composition, to provide the PMO at a dosage/body mass concentration of up to an amount selected from: 1. 0.05, 0.1, 0.15, 0.2, 0.3, 0.5, 1, 1.5, 2, 3, 5, 10, 15, 20, 30, 50, 100, 200, and 500 mg/kg, about any of the foregoing values, and a range between any of the foregoing values.mg/kg, about any of the foregoing values, and a range between any of the foregoing values.

Other factors include the mode and site of administration. The pharmaceutical compositions may be formulated to be provided to the subject in any method known in the art. Exemplary dosage forms include ocular, subcutaneous, intravenous, topical, epicutaneous, oral, intraosseous, intramuscular, intranasal, and pulmonary. The compositions of the present disclosure may be formulated to be administered only once to the subject or more than once to the subject. Furthermore, when the compositions are administered to the subject more than once, they may be formulated for a variety of regimens, such as once per day, once per week, once per month, or once per year. The compositions may also be formulated to be administered to the subject more than one time per day. The therapeutically effective amount of the antiviral agent and appropriate dosing regimens may be identified by testing in order to obtain optimal activity while minimizing any potential side effects. In addition, a formulation for co-administration or sequential administration of other agents may be desirable.

The compositions of the present disclosure may be formulated to be administered systemically, such as by intravenous administration, or locally such as by subcutaneous injection or by application of a gel, fiber, paste, or cream.

The compositions of the present disclosure may further comprise agents which improve the solubility, half-life, absorption, etc. of the antiviral agent. Furthermore, the compositions of the present disclosure may further comprise agents that attenuate undesirable side effects and/or decrease the toxicity of the antiviral agent. Examples of such agents are described in a variety of texts, such as Remington: The Science and Practice of Pharmacy (20th Ed., Lippincott, Williams & Wilkins, Daniel Limmer, editor).

The compositions of the present disclosure can be formulated in a wide variety of dosage forms for administration. For example, the compositions can be in the form of tablets, capsules, sachets, lozenges, troches, pills, powders, granules, elixirs, tinctures, solutions, suspensions, syrups, ointments, creams, pastes, emulsions, or solutions for intravenous administration or injection. Other dosage forms include for administration transdermally, via patch mechanism or ointment. Further dosage forms include formulations suitable for delivery by nebulizers or metered-dose inhalers. Any of the foregoing may be modified to provide for timed-release and/or sustained-release formulations.

In the present disclosure, the pharmaceutical compositions may further comprise a pharmaceutically acceptable carrier. Such carriers may include vehicles, adjuvants, surfactants, suspending agents, emulsifying agents, inert fillers, diluents, excipients, wetting agents, binders, lubricants, buffering agents, disintegrating agents, accessory agents, coloring agents, and flavoring agents (collectively referred to herein as a carrier). Typically, the pharmaceutically acceptable carrier is chemically inert to the antiviral agents and has no detrimental side effects or toxicity under the conditions of use. The pharmaceutically acceptable carriers can include polymers and polymer matrices. The nature of the pharmaceutically acceptable carrier may differ depending on the particular dosage form employed and other characteristics of the composition.

For instance, in compositions for oral administration in solid forms, such as tablets, capsules, sachets, lozenges, troches, pills, powders, or granules, the antiviral agent may be combined with an oral, non-toxic pharmaceutically acceptable inert carrier, such as inert fillers, suitable binders, lubricants, disintegrating agents, and accessory agents. Suitable binders include, without limitation, starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include, without limitation, sodium oleate, sodium stearate, magnesium stearate, sodium benzoate, sodium acetate, and the like. Disintegrators include, without limitation, starch, methyl cellulose, agar, bentonite, xanthan gum, and the like. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, as well as the other carriers described herein. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, and gels containing, in addition to the active ingredient, such carriers as are known in the art.

The composition may also be in oral liquid forms, such as a tincture, solution, suspension, elixir, and syrup; and the antiviral agents of the present disclosure can be dissolved in diluents, such as water, saline, or alcohols. Furthermore, the oral liquid forms may comprise suitably flavored suspending or dispersing agents such as synthetic and natural gums, for example, tragacanth, acacia, methylcellulose, and the like. Moreover, when desired or necessary, suitable coloring agents or other accessory agents can also be incorporated into the mixture. Other dispersing agents that may be employed include glycerin and the like.

Formulations suitable for parenteral administration include aqueous and non-aqueous, isotonic sterile injection solutions, which can contain anti-oxidants, buffers, bacteriostats, and solutes that render the formulation isotonic with the blood of the patient, and aqueous and non-aqueous sterile suspensions that can include suspending agents, solubilizers, thickening agents, stabilizers, and preservatives. The composition may comprise a physiologically acceptable diluent, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap, an oil or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include polyethylene sorbitan fatty acid esters, such as sorbitan monooleate and the high molecular weight adducts of ethylene oxide with a hydrophobic base, formed by the condensation of propylene oxide with propylene glycol, oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include: (a) cationic detergents such as, for example, dimethyldialkylammonium halides, and alkylpyridinium halides; (b) anionic detergents such as, for example, alkyl, aryl, and olefin sulfonates, alkyl, olefin, ether, and monoglyceride sulfates, and sulfosuccinates; (c) nonionic detergents such as, for example, fatty amine oxides, fatty acid alkanolamides, and polyoxyethylene polypropylene copolymers; (d) amphoteric detergents such as, for example, alkylbeta-aminopropionates, and 2-alkylimidazoline quaternary ammonium salts; and (e) mixtures thereof.

Suitable preservatives and buffers can be used in such formulations. In order to minimize or eliminate irritation at the site of injection, such compositions may contain one or more nonionic surfactants having a hydrophile-lipophile balance (HLB) of from about 12 to about 17.

Topical dosage forms, such as ointments, creams, pastes, and emulsions, containing the antiviral agent, can be admixed with a variety of carrier materials well known in the art, such as, e.g., alcohols, aloe vera gel, allantoin, glycerine, vitamin A and E oils, mineral oil, PPG2 myristyl propionate, and the like, to form alcoholic solutions, topical cleansers, cleansing creams, skin gels, skin lotions, and shampoos in cream or gel formulations. Inclusion of a skin exfoliant or dermal abrasive preparation may also be used. Such topical preparations may be applied to a patch, bandage, or dressing for transdermal delivery, or may be applied to a bandage or dressing for delivery directly to the site of a wound or cutaneous injury.

The antiviral agents of the present disclosure can also be formulated to be administered in the form of liposome delivery systems, such as small unilamellar vesicles, large unilamellar vesicles, and antiemetics. Liposomes can be formed from a variety of phospholipids, such as cholesterol, stearylamine, or phosphatidylcholines. Such liposomes may also contain monoclonal antibodies to direct delivery of the liposome to a particular cell type or group of cell types.

The antiviral agents of the present disclosure may also be coupled with soluble polymers as targetable drug carriers. Such polymers can include polyvinyl-pyrrolidone, pyran copolymer, polyhydroxypropylmethacryl-amidephenol, polyhydroxyethylaspartamidephenol, or polyethyl-eneoxidepolylysine substituted with palmitoyl residues. Furthermore, the antiviral agents of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates, and cross-linked or amphipathic block copolymers of hydrogels.

D. Methods of Use

By way of non-limiting example only, methods of using the antiviral agents and pharmaceutical compositions disclosed above are provided.

A method of treatment or prevention of a disease mediated by a coronavirus, such as SARS-CoV-2, in a subject in need thereof is provided, the method comprising administering to the subject a therapeutically effective amount of any of the pharmaceutical compositions or antiviral agents disclosed above. The disease may be any that is caused, complicated, or exacerbated by a coronavirus infection, which in the case of SARS-CoV-2 infection, includes COVID-19. The coronavirus infection need not be in the subject him or herself; for example, the method could be used for the prevention of microcephaly in a fetus by the administration to the mother.

The method of treatment and/or prevention comprises administering to the subject the antiviral agent or the pharmaceutical composition in an amount sufficient to treat or prevent the coronavirus-mediated disease (i.e., a therapeutically effective amount). The method will often further comprise identifying a subject in need of such treatment or prevention. Too small of an amount of the antiviral agent would fail to provide the therapeutic effect. On the other hand, an excessive amount of antiviral agent could lead to undesired side effects.

The therapeutically effective amount may vary according to a variety of factors such as the subject's condition, weight, sex, and age. For example, some embodiments of the method comprise the administration of up to the median lethal dose ($LD_{50}$) of the antiviral agent. The $LD_{50}$ can be ascertained using standard toxicological methods, or by reference to past studies. Alternatively, the method may comprise delivering a desired concentration of the antiviral agent to a tissue, organ, or cell type that hosts the coronavirus (such as SARS-CoV-2) in the subject.

If, after the administration of the antiviral agent, the subject still has the coronavirus-mediated disease, or is at risk for the same, then an optional step of the method is to continue the administration of the antiviral agent or pharmaceutical composition.

In one embodiment, the method comprises delivering the antiviral agent to a tissue, organ, or cell type of the subject that hosts a strain of coronavirus (e.g., SARS-CoV-2). Such tissues and organs include the lungs, respiratory epithelial cells, endothelial cells, circulatory system organs or cells, respiratory system organs or cells, cardiac system pulmonary system organs or cells, renal system organs or cells, gastrointestainl system organs or cells, lung cells, brain cells, skin cells, podocytes, monocytes, T lymphocytes, macrophases carbomyocytes, eyes, retinal tissue, retinal endothelial cells, retinal microvascular endothelial cells, retinal pigmented epithelial cells, retinal pericytes, kidney, glomerular tissue, glomerular podocytes, renal glomerular endothelial cells, mesangial cells, cytotrophoblasts, syncytiotrophoblast, human brain microvascular endothelial cells, human neural stem cells, astrocytes, neuroblastoma cells, neural progenitor cells, placental endothelial cells, placental fibroblasts, Hofbauer cells, amniotic epithelial cells, chorionic villi cells, keratinocytes, dermal fibroblasts, dendritic cells, umbilical vein endothelial cells, aortic endothelial cells, coronary artery endothelial cells, saphenous vein endothelial cells, glial cells, primary spermatocytes, Sertoli cells, retinal bipolar cells, retinal ganglion cells, optic nerve cells, and Vero cells, and any combination of the foregoing. It is desirable to deliver the antiviral agent to such targets because they are the sites of infection and replication. Targeted delivery could also prevent unwanted effects on other tissues or organs. In an alternate embodiment, the method comprises administering the antiviral agent locally, such as to the subjects respiratory system (e.g., nasally).

A method of reducing or preventing the replication of a strain of a coronavirus (e.g., SARS-CoV-2) in a host cell is provided, the method comprising contacting the host cell with an effective concentration any of the antiviral agents described above. In a specific embodiment of the method, the effective concentration is at least about 10, 12, 15, 20, 30, 50, 100, 250, or 500 μM. In a further specific embodiment of the method, the effective concentration is about 10, 12, 15, 20, 30, 50, 100, 250, or 500 μM, or any subrange thereof. The host cell may be situated in vivo or ex vivo and may be any cell type known to be permissive to coronaviruses, including any of those listed above.

A method of controlling the spread of coronaviruses in donated tissue is provided, the method comprising exposing the donated tissue to an effective amount of any embodiment of the antiviral agent or pharmaceutical composition disclosed above. The donated tissue may be in the form of a donated organ. The organ or tissue may be exposed to the antiviral agent by perfusing the organ or tissue with a solution containing the effective concentration of the antiviral agent. In a specific embodiment of the method, the effective concentration is at least about 10, 12, 15, 20, 30, 50, 100, 250, or 500 μM. In a further specific embodiment of the method, the effective concentration is about 10, 12, 15, 20, 30, 50, 100, 250, or 500 μM, or any subrange thereof. The antiviral agent may be part of an organ preservation composition, such as the University of Wisconsin cold storage solution (available from Bridge to Life Ltd., Columbia, South Carolina) or any other organ preservation solution known in the art. Another aspect of the disclosed work is a treated donated organ or tissue, comprising an organ preservation composition that includes an effective amount of any of the antiviral agents listed above.

E. Prophetic Example 1

The use of PMO based technology targeting the nucleotide translation initiation complex site of ZIKV for antiviral development will be explored.

The 5'UTR sequences of SARS-CoV-2 are similar to those of other SARS-like-βCoVs with nucleotide identities of >83.6% [1]. The approach of targeting highly conserved sequences among βCoVs in both human and animal viruses with specific morpholinos should provide broad protection against phylogenetically similar family member βCoVs. The initial approach is to design a morpholino that will anneal to 5'UTR to accomplish translation arrest post-infection to inhibit the production of all viral proteins downstream including the pp1a protease that is required for viral replication and thereby producing no viral progeny and no viral proteins. The synthesis of the morpholino will be performed by Gene Tools. In vitro toxicity will be examined in lung adenocarcinoma cell line A549 and the lung epithelial cell line Calu-3. In collaboration with Ann Eakin, Ph.D. Senior Scientific Officer, Concept Acceleration Program Office of Biodefense, Research Resources & Translational Research/DMID/NIAID/NIH, SARS-CoV-2 will be cultivated in HCT-8 [HRT-18] ATCCβ CCL-244 cells according to the manufacturer's recommendations. SARS-CoV-2 infection of permissive cells and controls will be performed in triplicate in 6 well dishes pretreated with 0.1 uM-10 uM of the antiviral agent (referred to as "MRCV-19" in these prophetic examples) reconstituted in purified water to determine the effect and effective dose for MRCV-19 on SARS-CoV-2 replication. qRT-PCR and western blot analysis will be performed to determine the effects of MRCV-19 treatment on mRNA and total protein expression of SARS-CoV-2 envelope and spike glycoproteins. The effects MRCV-19 on SARS-CoV-2 induction proinflammatory cytokines will also be determined [2]. It will also be determined whether MRCV-19 can prevent SARS-CoV-2-induced death in newborn mice. It is expected that significant suppression of SARS-CoV-2 mRNA, protein expression, and induction of proinflammatory cytokines will occur. It is also expected that a significant increase in survival of newborn C57BL/6 mice pups inoculated intracerebrally [3] with SARS-CoV-2 after treatment with MRCV-19 compared to controls will occur. MRCV-19 effectiveness to inhibit COVID-19 replication and gene expression in culture and in a mouse infection model will be done via the DMID/NIAID/NIH collaboration.

Selecting a 5' UTR target sequence based on conserved sequences among SARS-CoV, SARS-CoV-2 (COVID-19), and the bat SARS-like-CoVZXC21 that represent both human and animal sequences that are most similar to the SARS-CoV-2 virus that causes COVID-19. The sequences represent the 5'UTR for SARS-CoV-2, the bat SARS-like-CoVZXC21 and SARS-CoV [4-6]. The start site for pp1a (ATG) is shown in highlighting with white text (FIG. 1). A complementary sequence that overlaps the 5'UTR and the regions immediately downstream of the ATG start site was identified as the target to engage the SARS-CoV-2 virus upon entry into permissive cells in vitro and in vivo based on its genome structure (FIG. 2A). The structure of the in vivo morpholino and the complementary sequence targeting SARS-CoV-2 genome are shown in FIG. 2B.

The SARS-CoV-2-targeted phosphoramidate dendrimer MRCV-19 will be designed to be complementary to the 25-mer nucleotide sequence within the 5'UTR of the pp1a gene sequence that includes the pp1a ATG start site designated as MRCV-19 start site (FIG. 2A). The control dendrimer reagent used in this study will be a standard control oligo that targets a human beta-globin intron mutation that causes beta-thalassemia. Controls cause little change in phenotype in any known test system except human beta-thalassemia hematopoietic cells and are appropriate negative control for custom phosphoramidate dendrimer.

REFERENCES

1. Chan J F, To K K, Tse H, et al. Interspecies transmission and emergence of novel viruses: lessons from bats and birds. Trends Microbiol. 2013; 10:544-555.
2. Ye Q, Wang B, Mao J. The pathogenesis and treatment of the 'Cytokine Storm' in COVID-19. JInfect. 2020 Apr. 10:S0163-4453(20)30165-1. doi: 10.1016/j.jinf.2020.03.037.
3. Antiviral Activity of Chloroquine against Human Coronavirus OC43 Infection in Newborn Mice June 2009 Antimicrobial Agents and Chemotherapy 53(8):3416-21.
4. Chan J F, Yuan S, Kok K H, To K K, Chu H, Yang J, Xing F, Liu J, Yip C C, Poon R W, Tsoi H W, Lo S K, Chan K H, Poon V K, Chan W M, Ip J D, Cai J P, Cheng V C, Chen H, Hui C K, Yuen K Y. A familial cluster of pneumonia associated with the 2019 novel coronavirus indicating person-to-person transmission: a study of a family duster. Lancet. 2020 Feb. 15; 395(10223):514-523. doi: 10.1016/S0140-6736(20)30154-9. Epub 2020 Jan. 24.
5. Hu D, Zhu C, Ai L, He T, Wang Y, Ye F, Yang L, Ding C, Zhu X, Lv R, Zhu J, Hassan B, Feng Y, Tan W, Wang C. Genomic characterization and infectivity of a novel SARS-like coronavirus in Chinese bats. Emerg Microbes Infect. 2018 Sep. 12; 7(1):154. doi: 10.1038/s41426-018-0155-5.
6. Marra M A, Jones S J, Astell C R, Holt R A, Brooks-Wilson A, Butterfield Y S, Khattra J, Asano J K, Barber S A, Chan S Y, Cloutier A, Coughlin S M, Freeman D, Gim N, Griffith O L, Leach S R, Mayo M, McDonald H, Montgomery S B, Pandoh P K, Petrescu A S, Robertson A G, Schein J E, Siddiqui A, Smailus D E, Stott J M, Yang G S, Plummer F, Andonov A. Artsob H. Bastien N. Bemard K, Booth T F, Bowness D, Czub M, Drebot M, Fernando L, Flick R, Garbutt M, Gray M, Grolla A, Jones S, Feldmann H, Meyers A, Kabani A, Li Y, Normand S, Stroher U, Tipples G A, Tyler S, Vogrig R, Ward D, Watson B, Brunham R C, Krajden M, Petric M, Skowronski D M, Upton C, Roper R L. The Genome sequence of the SARS-associated coronavirus. Science. 2003 May 30; 300(5624):1399-404. doi: 10.1126/science.1085953.

F. Prophetic Example 2—Effective Amounts of "MRCV-19"

A549 cell toxicity assays will be used to test a range of concentrations from 0.1 μM to 10 μM. To determine an effective concentration of MRCV-19 that inhibits SARS-CoV-2 replication, A549 cells, will be pretreated for 24 h with various concentrations of MRCV-19 ranging from 0.1 to 10 μM, rinsed and mock-infected or infected with SARS-CoV-2 at a multiplicity of infection (MOI) of 0.1 in the absence of MRCV-19. Seventy-two hours after infection, the cells will be collected and total protein and intracellular SARS-CoV-2 RNA accumulation will be determined by qRT-PCR and western blot analysis. Anticipated results. MRCV-19 will reduce intracellular SARS-CoV-2 mRNA accumulation in a dose-dependent manner by >95%. Immunoblot analysis will demonstrate a strong inhibition of SARS-CoV-2 protein expression by MRCV-19.

G. Prophetic Example 3—Preclinical Studies

Animal toxicity studies. MRCV-19 toxicity studies will be performed in CD-1 mice as a fee for service by Pacific Biolab, Hercules CA. Analysis that includes daily animal monitoring of morbidity and mortality 96 hours after subcutaneous injection will be performed. Harvesting of mouse lung tissue from MRCV-19 treated and untreated animals will be done to determine the virus burden, or load, before and after treatment.

Demonstrate MRCV-19 inhibition of SARS-CoV-2 replication in cell culture and in a mouse model. It will be demonstrated that MRCV-19 inhibition of SARS-CoV-2 replication and protein expression occurs in human lung and respiratory epithelial and endothelial cells and cell lines human cerebral organoid model in lieu of Phase I trials. Suppression of SARS-CoV-2 infection with a mouse infection model will be examined. Viral titers post-infection will be examined in lung and respiratory tissue that will be formalin-fixed and paraffin-embedded and analyzed by immunohistochemistry (IHC). In addition, the viral burden will be quantitated using total mRNA extracted from fresh frozen mouse brain tissue by qRT-PCR.

H. Conclusions

It is to be understood that any of the given elements of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

What is claimed is:

1. An antiviral agent that restricts the replication of a coronavirus in a cell, the agent comprising a phosphorodiamidate morpholino oligomer (PMO) comprising an antisense sequence of 25 nucleotides in length, wherein the antisense sequence is 5'-AGG GAC AAG GCT CTC CAT CTT ACC T-3' (SEQ ID NO: 1), or 5'-AAG AAC AAG GCT CTC CAT CTT ACC T-3' (SEQ ID NO: 3).

2. The antiviral agent of claim 1, wherein the agent comprises a moiety for intracellular delivery.

3. The antiviral agent of claim 1, wherein the agent comprises an octaguanidine dendrimer delivery moiety.

4. The antiviral agent of claim 1, wherein the agent comprises an octaguanidine dendrimer of the following structure:

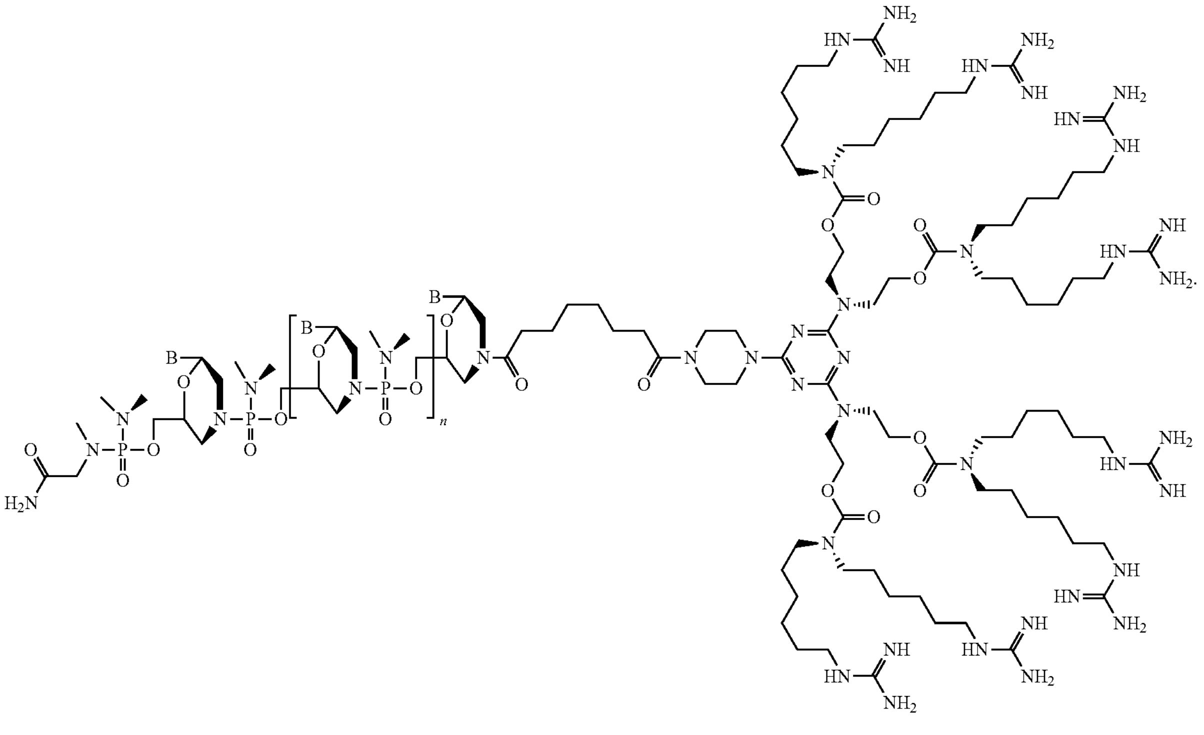

5. The antiviral agent of claim 1, wherein the coronavirus is selected from the group consisting of SARS-CoV-2, SARS-CoV, and bat SARS-like-CoVZXC21.

6. The antiviral agent of claim 1, wherein the coronavirus is a βCoV.

7. A composition for restricting the replication of a coronavirus in a cell in vitro, the composition comprising: the antiviral agent of claim 1 and a carrier.

8. The composition of claim 7, wherein the carrier is selected from the group consisting of a vehicle, an adjuvant, a surfactant, a suspending agent, an emulsifying agent, an inert filler, a diluent, an excipient, a wetting agent, a binder, a lubricant, a buffering agent, a disintegrating agent, an accessory agent, a coloring agent, and a flavoring agent.

9. The composition of claim 7, wherein the antiviral agent is present at a concentration of at least 10 micromolar.

10. The composition of claim 7, wherein the coronavirus is SARS-CoV-2.

11. A method of reducing or preventing the replication of a coronavirus in a host cell in vitro, the method comprising contacting the host cell in vitro with an effective amount of the antiviral agent of claim 1.

12. The method of claim 11, wherein the coronavirus is SARS-CoV-2 .

13. The method of claim 11, wherein the host cell is selected from the group consisting of a respiratory epithelial cell, an endothelial cell, a retinal endothelial cell, a retinal microvascular endothelial cell, a retinal pigmented epithelial cell, a retinal pericyte, a kidney cell, a gomerular podocyte, a renal glomerular endothelial cell, mesangial call, cytotrophoblasts, syncytiotrophoblast, human brain microvascular endothelial cells, human neural stem cells, astrocytes, neuroblastoma cells, neural progenitor cells, placental endothelial cells, placental fibroblasts, Hofbauer cells, amniotic epithelial cells, chorionic villi cells, keratinocytes, dermal fibroblasts, dendritic cells, umbilical vein endothelial cells, aortic endothelial cells, coronary artery endothelial cells, saphenous vein endothelial cells, glial cells, primary spermatocytes, Sertoli cells, retinal bipolar cells, retinal ganglion cells, optic nerve cells, Vero cells, and combinations thereof.

14. The method of claim 11, wherein the host cell is selected from the group consisting of: a respiratory epithelial cell, an endothelial cell, and a combination thereof.

* * * * *